US009994998B2

(12) United States Patent
Chen et al.

(10) Patent No.: US 9,994,998 B2
(45) Date of Patent: Jun. 12, 2018

(54) KEY GENE REGULATING PLANT CELL WALL RECALCITRANCE

(71) Applicant: UT-Battelle, LLC, Oak Ridge, TN (US)

(72) Inventors: Jay Chen, Oak Ridge, TN (US); Lee E. Gunter, Oak Ridge, TN (US); Sara Jawdy, Oak Ridge, TN (US); Wellington Muchero, Oak Ridge, TN (US); Gerald Tuskan, Oak Ridge, TN (US); Jianjun Guo, Sunnyvale, CA (US); Priya Ranjan, Knoxville, TN (US); Stephen P. DiFazio, Morgantown, VA (US); Anthony C. Bryan, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 210 days.

(21) Appl. No.: 14/638,838

(22) Filed: Mar. 4, 2015

(65) Prior Publication Data
US 2016/0053275 A1 Feb. 25, 2016

Related U.S. Application Data

(60) Provisional application No. 61/948,291, filed on Mar. 5, 2014.

(51) Int. Cl.
| | |
|---|---|
| *C12N 15/82* | (2006.01) |
| *D21H 11/12* | (2006.01) |
| *D21C 3/00* | (2006.01) |
| *D21H 11/00* | (2006.01) |
| *D21H 11/20* | (2006.01) |

(52) U.S. Cl.
CPC ......... *D21H 11/12* (2013.01); *C12N 15/8255* (2013.01); *C12N 15/8271* (2013.01); *D21C 3/00* (2013.01); *D21H 11/00* (2013.01); *D21H 11/20* (2013.01)

(58) Field of Classification Search
None
See application file for complete search history.

(56) References Cited

PUBLICATIONS

Atanesyan, et al., "Polyglutamine Tracts as Modulators of Transcriptional Activation from Yeast to Animals"; Biol. Chem., vol. 393, pp. 63-70 (2012).
Crowell, et al., "Pausing of Golgi Bodies on Microtubules Regulates Secretion of Cellulose Synthase Complexes in Arabidopsis"; The Plant Cell, vol. 21:1141-1154, Apr. 2009.
Fu, et al., "Genetic Manipulation of Lignin Reduces Recalcitrance and Improves Ethanol Production from Switchgrass"; PNAS, vol. 108, No. 9, pp. 3803-3808 (Mar. 1, 2011).
Gachomo, et al., "The Cell Morphogenesis *Angustifolia* (AN) Gene, A Plant Homolog of CtBP/BARS, is Involved in Abiotic and Biotic Stress Response in Higher Plants"; BMC Plant Biology 12:79, 2013.
Geraldes, et al., "1 34K SNP Genotyping Array for Populus Trichocarpa: Design, Application to the Study of Natural Populations and Transferabililtyh to other Populus Species"; Molecular Ecology Resources 13, pp. 306-323 (2013).
Kalluri, et al., "Shotgun Proteome Profile of Populus Developing Xylem"; Proteomics 2009, 9, pp. 4871-4880.
Kim, et al., "The *Angustifolia* Gene of *Arabidopsis*, a Plant CtBP Gene, Regulates Leaf-Cell Expansion, the Arrangment of Cortical Microtubules in Leaf Cells and Expression of a Gene Involved in Cell-Wall Formation"; The EMB Journal, vol. 21, No. 6, pp. 1267-1279, 2002.
Novaes, et al., "Quantitative Genetic Analysis of Biomass and Wood Chemistry of Populus Under Different Nitrogen Levels"; New Phytologist (2009) 182: pp. 878-890.
Porth, et al., "Genome-Wide Association Mapping for Wood Characteristics in Populus Identifies an Array of Candidate Single Nucleotide Polymorphisms"; New Phytologist (2013) 200: pp: 710-726.
Porth, et al., "Populus Trichocarpa Cell Wall Chemistry and Ultrastructure Trait Variation, Genetic Control and Genetic Correlations"; New Phytologist (2013) 197: pp. 770-790.
Ranjan, et al., "Bioinformatics-Based Identification of Candidate Genes from QTLs Associated with Cell Wall Traits in Populus"; Bioenergy Research, Nov. 6, 2009, vol. 3, Issue 2, pp. 172-182.
Slavov, et al.; "Genome Resequencing Reveals Multiscale Geographic Structure and Extensive Linkage Disequilibrium in the Forest Tree Populus Trichocarpa"; New Phytologist (2012) 196: pp. 713-725.
Studer, et al., "Lignin Content in Natural Populus Variants Affects Sugar Release"; PNAS, Apr. 12, 2011, vol. 108, No. 15, pp. 6300-6305.
Vermerris, et al., "Molecular Breeding to Enhance Ethanol Production from Corn and Sorghum Stover"; International Plant Breeding Symposium, Dec. 2007; Published in Crop Sci. 47(S3) S142-S153 (2007).

(Continued)

*Primary Examiner* — Brent T Page
(74) *Attorney, Agent, or Firm* — Scully Scott Murphy & Presser

(57) ABSTRACT

This disclosure provides plants having desirable levels of lignin synthesis, sugar release, S/G ratio, and resistance to stress and pathogens; methods of selecting plants with such desirable levels of lignin synthesis, sugar release, S/G ratio, and resistance to stress and pathogens; methods of genetically modifying plants to modulate lignin synthesis, sugar release, S/G ratio, and resistance to stress and pathogens; and uses of such plants. The inventors have determined that the expression and/or activity of POPTR_0014s08530, a gene encoding an *Angustifolia*/CtBP transcription factor, modulates lignin synthesis, sugar release, S/G ratio, and resistance to stress and pathogens in plants. Plants with lignin synthesis, sugar release, S/G ratio, and resistance to stress and pathogens, based on modulation of the expression or activity of the POPTR_0014s08530 gene, have divergent uses including pulp and paper production, and ethanol/biofuel production.

14 Claims, 18 Drawing Sheets

(56) References Cited

PUBLICATIONS

Yin, et al., "Differential Detection of Genetic Loci Underlying Stem and Root Lignin Content in Populus"; PloS ONE, vol. 5, Issue 11, Nov. 2010.

|  | | 20 | | 40 | |
|---|---|---|---|---|---|
| Potri.014G089400_A | MSATTTRSLA | TMSHRRNTNT | PPPPQQQQQQ | QQQQQQQQQR | LPLVVTLNCI | 50 |
| Potri.014G089400_B | MSATTTRSLA | TMSHRRNTNT | PPPPQQQQQQ | QQQQQQQ - - R | LPLVVTLNCI | 48 |
| Potri.002G163200 | MSATNRSST | TMSLHHLTTN | PPPPQQN - - - | - - - - - - - - - | LPLVVTLNCI | 37 |
| At1g01510 | MSKI - - RSSA | TMPHR - - - DQ | PSPAS - - - - - | - - - - - - - - - | - PHVVTLNCI | 29 |

| 60 | | 80 | | 100 | |
|---|---|---|---|---|---|
| Potri.014G089400_A | EDFAI EQDSL | SGVALI EHVP | LGRLSDGKIE | SAAAVLLHSL | AYLPRAAQRR | 100 |
| Potri.014G089400_B | EDFAI EQDSL | SGVALI EHVP | LGRLSDGKIE | SAAAVLLHSL | AYLPRAAQRR | 98 |
| Potri.002G163200 | EDCAI EQDSL | SGVASI EHVP | LSRLSGGKIE | SAAAVLLHSL | AYLPRAAQRR | 87 |
| At1g01510 | EDCALEQDSL | AGVAGVEYVP | LSRI ADGKIE | SATAVLLHSL | AYLPRAAQRR | 79 |

| 120 | | 140 | | | |
|---|---|---|---|---|---|
| Potri.014G089400_A | LRPYQLI LCL | GSADRAVDSA | LAADLGLRLV | HVDT SRAEEI | ADT VMALFLG | 150 |
| Potri.014G089400_B | LRPYQLI LCL | GSADRAVDSA | LAADLGLRLV | HVDT SRAEEI | ADT VMALFLG | 148 |
| Potri.002G163200 | LRPYQLI LCL | GSADRAVDSA | LAADLGLRLV | HVDNSRAEEI | ADT VMALFLG | 137 |
| At1g01510 | LRPHQLI LCL | GSADRAVDST | LAADLGLRLV | HVDT SRAEEI | ADT VMALI LG | 129 |

| 160 | | 180 | | 200 | |
|---|---|---|---|---|---|
| Potri.014G089400_A | LLRTHLLSR | HALSASGWLG | SLQP LCRGMR | RCRGL VLGIV | GRSASARS LA | 200 |
| Potri.014G089400_B | LLRRTHLLSR | HALSASGWLG | SLQP LCRGMR | RCRGL VLGIV | GRSASARS LA | 198 |
| Potri.002G163200 | LLRRTHLLSR | HT LSASGWLG | SVQP LCRGMR | RCRG LV LGI V | GRSASAKS LA | 187 |
| At1g01510 | LLRRTHLLSR | HALSASGWLG | SLQP LCRGMR | RCRGMV LGI V | GRSVSARY LA | 179 |

| 220 | | 240 | | | |
|---|---|---|---|---|---|
| Potri.014G089400_A | TRS LAFKMSV | LY FDVHEGPG | KL TRSSI T F P | LAARRMDT LN | DL LAASDLI S | 250 |
| Potri.014G089400_B | TRS LAFKMSV | LY FDVHEGPG | KL TRSSI T F P | LAARRMDT LN | DL LAASDLI S | 248 |
| Potri.002G163200 | TRS LAFKI SV | LY FDVHEGPG | I L SRSSI AF P | SAARRMDT LN | DL LAASDLI S | 237 |
| At1g01510 | SRS LAFKMSV | LY FDVPEGDE | ERI RPS - RF P | RAARRMDT LN | DL LAASDVI S | 228 |

| 260 | | 280 | | 300 | |
|---|---|---|---|---|---|
| Potri.014G089400_A | LHCALTNE T V | QI I NEECLQH | I KPGAF L VNT | GSSQL LDDCA | LKQL LI DGT L | 300 |
| Potri.014G089400_B | LHCALTNE T V | QI I NEECLQH | I KPGAF L VNT | GSSQL LDDCA | LKQL LI DGT L | 298 |
| Potri.002G163200 | LHCALTNE T V | QI I SAECLQH | I KPGAF L VNT | GSSQL LDDCA | LKQL LI DGT L | 287 |
| At1g01510 | LHCALTNDT V | QI LNAECLQH | I KPGAF L VNT | GSCQL LDDCA | VKQL LI DGT I | 278 |

| 320 | | 340 | | | |
|---|---|---|---|---|---|
| Potri.014G089400_A | AGCALDGAEG | PQWMEAWVKE | MPNV LI L PRS | ADYSEEVWME | I REKAI SI LQ | 350 |
| Potri.014G089400_B | AGCALDGAEG | PQWMEAWVKE | MPNV LI L PRS | ADYSEEVWME | I REKAI SI LQ | 348 |
| Potri.002G163200 | AGCALDGAEG | PQWMEAWVKE | MPNV LI L PRS | ADYSEEVWME | I RDKAI SI LQ | 337 |
| At1g01510 | AGCALDGAEG | PQWMEAWVKE | MPNV LI L PRS | ADYSEEVWME | I REKAI SI LH | 328 |

Fig. 1A

| | | 360 | | 380 | | 400 | |
|---|---|---|---|---|---|---|---|
| Potri.014G089400_A | SFFFDGIVPK | NAVSDEEGEE | SEIGDESEQF | HRQDKESTLQ | DSVGEQLTDD | 400 |
| Potri.014G089400_B | SFFFDGIVPK | NAVSDEEGEE | SEIGDESEQF | HRQDKESTLQ | DSVGEQLTDD | 398 |
| Potri.002G163200 | SFFLDGTVPK | NAVSDEEEEE | SEIGEESDQF | HRQDKESTLQ | DSVVEQLTDD | 387 |
| At1g01510 | SFFLDGVIPS | NTVSDEEVEE | SEASEEEQS | PSKHEKLAIV | ESTSRQQGES | 378 |

| | | 420 | | 440 | | | |
|---|---|---|---|---|---|---|---|
| Potri.014G089400_A | IQLTPETSRK | KVSGQSIEST | SQAQGSGMSQ | NTTTRSDERR | SRSGKKAKKR | 450 |
| Potri.014G089400_B | IQLTPETSRK | KVSGQSIEST | SQAQGSGMSQ | NTTTRSDERR | SRSGKKAKKR | 448 |
| Potri.002G163200 | VQVTLESYHK | KVISQSIEST | SKAQVSGMSQ | NMATRTEGRR | NRLGKKAKKR | 437 |
| At1g01510 | TLTSTEIVRR | EAS-ELKESL | SPGQ-QHVSQ | NTAVKPEGRR | RSGKKAKKR | 426 |

| | | 460 | | 480 | | 500 | |
|---|---|---|---|---|---|---|---|
| Potri.014G089400_A | HGRQKPRQKS | DNPSQLEKES | TSHQEDDTAM | SGSDQV--SS | SRFASPEDSR | 498 |
| Potri.014G089400_B | HGRQKPRQKS | DNPSQLEKES | TSHQEDDTAM | SGSDQV--SS | SRFASPEDSR | 496 |
| Potri.002G163200 | HGHQKSQQKS | DDPSQLEKEI | TSHQEDDIAM | SGTDQVLSSG | SRFASPEDSR | 487 |
| At1g01510 | HSQQKYMQKT | DGSSGLNEES | TSRR-DDIAM | SDTEEVLSSS | SRCASPEDSR | 475 |

| | | 520 | | 540 | | | |
|---|---|---|---|---|---|---|---|
| Potri.014G089400_A | SRKTPIELMQ | ESSSGQLSRS | GKRLSGKSDE | LLKDGHIIAL | YARDRPALHV | 548 |
| Potri.014G089400_B | SRKTPIELMQ | ESSSGQLSRS | GKRLSGKSDE | LLKDGHIIAL | YARDRPALHV | 546 |
| Potri.002G163200 | SRKTPIELTQ | DPTSGQLSRS | GKKLSGKSDK | LLKDGHIIAL | YARDHSALHV | 537 |
| At1g01510 | SRKTPLEVMQ | ESSPNQLVMS | SKKFIGKSSE | LLKDGYVVAL | YAKDLSGLHV | 525 |

| | | 560 | | 580 | | 600 | |
|---|---|---|---|---|---|---|---|
| Potri.014G089400_A | SRQRAKGGGW | FLDALSNVTK | RDPAAQFLVV | FRNKDTIGLR | SFAAGGKLLQ | 598 |
| Potri.014G089400_B | SRQRAKGGGW | FLDALSNVTK | RDPAAQFLVV | FRNKDTIGLR | SFAAGGKLLQ | 596 |
| Potri.002G163200 | SRQRVKGGGW | FLDAMSNVTK | RDPAAQFLVV | FRSKDTIGLR | SFAAGGKLLQ | 587 |
| At1g01510 | SRQRTKNGGW | FLDTLSNVSK | RDPAAQFIIA | YRNKDTVGLR | YAKDLSGLHV | 575 |

| | | 620 | | 640 | | | |
|---|---|---|---|---|---|---|---|
| Potri.014G089400_A | INRRMEFVFT | SHSFDVWESW | MLEGSLDECR | LVNCRNPLAI | LDARVEILAT | 648 |
| Potri.014G089400_B | INRRMEFVFT | SHSFDVWESW | MLEGSLDECR | LVNCRNPLAI | LDARVEILAA | 646 |
| Potri.002G163200 | INRRTEFVFA | SHSFDVWESW | MLEGSLEECR | LVNCRNPLAV | LEVRIEILAA | 637 |
| At1g01510 | INRRMEFVFA | SHSFDVWESW | SLEGSLDECR | LVNCRNSSAV | LDVRVEILAM | 625 |

| | | 660 | | | |
|---|---|---|---|---|---|
| Potri.014G089400_A | AEDDGVTRW | LD- | 660 |
| Potri.014G089400_B | IAEDDGVTRW | LD- | 658 |
| Potri.002G163200 | VGED-GVSRW | LD- | 648 |
| At1g01510 | VG-DDGITRW | ID* | 637 |

Fig. 1B

```
Potri.014G089400.1              ----------------------------------------------------
Potri.002G163200.1              ----------------------------------------------------
30174.m008658                   --------------------MNFQEQESNSYNLITSSATWLEIRLFYVRITPCV
cassava4.1_003595m              ----------------------------------------------------
Lus10007913                     ----------------------------------------------------
Lus10036393                     ----------------------------------------------------
TheclEG005268t1                 ----------------------------------------------------
Gorai.007G103000.1              ----------------------------------------------------
Gorai.004G159800.1              ----------------------------------------------------
evm.model.supercontig_184.28    ----------------------------------------------------
XP_002275405.2                  MDYEEGNSSIASAKSPNSRSNLYRIIDGHSSPPSVSLEIRLFYVRIAPCV
orange1.1g006758m               ----------------------------------------------------
Ciclev10019285m                 ----------------------------------------------------
Glyma09g39090.1                 ----------------------------------------------------
PGSC0003DMP400000412            ----------------------------------------------------
Eucgr.D02321.1                  ----------------------------------------------------
AT1G01510.1                     ----------------------------------------------------
LOC_Os10g38900.1                ----------------------------------------------------
Sobic.001G316200.1.p            ----------------------------------------------------
BAJ89523.1                      ----------------------------------------------------
GRMZM2G476107_T01               ----------------------------------------------------
BAA25287.1                      ----------------------------------------------------
AAC62822.1                      ----------------------------------------------------
NP_001185788.1                  ----------------------------------------------------
NP_001079151.1                  ----------------------------------------------------
                                1........10........20........30........40........50

Potri.014G089400.1              ----------------------------------------------------
Potri.002G163200.1              ----------------------------------------------------
30174.m008658                   IDSVPDHLTLRHLRREISTPLEINGSRIPAADSASVTLRRDRLNKESSEV
cassava4.1_003595m              ----------------------------------------------------
Lus10007913                     ----------------------------------------------------
Lus10036393                     ----------------------------------------------------
TheclEG005268t1                 ----------------------------------------------------
Gorai.007G103000.1              ----------------------------------------------------
Gorai.004G159800.1              ----------------------------------------------------
evm.model.supercontig_184.28    ----------------------------------------------------
XP_002275405.2                  IDSVPDHLTLCHIRRGIGVSLEINGARIPASETASLTLRRDRLDKESSEV
orange1.1g006758m               ----------------------------------------------------
Ciclev10019285m                 ----------------------------------------------------
Glyma09g39090.1                 ----------------------------------------------------
PGSC0003DMP400000412            ----------------------------------------------------
Eucgr.D02321.1                  ----------------------------------------------------
AT1G01510.1                     ----------------------------------------------------
LOC_Os10g38900.1                ----------------------------------------------------
Sobic.001G316200.1.p            ----------------------------------------------------
BAJ89523.1                      ----------------------------------------------------
GRMZM2G476107_T01               ----------------------------------------------------
BAA25287.1                      ----------------------------------------------------
AAC62822.1                      ----------------------------------------------------
NP_001185788.1                  ----------------------------------------------------
NP_001079151.1                  ----------------------------------------------------
                                ........60........70........80........90.......100
```

Fig. 2A

```
Potri.014G089400.1         ------------------------------------------------
Potri.002G163200.1         ------------------------------------------------
30174.m008658              TYVSTDSVRITGALEFEVIEENDLFLCGSLERIESITLWG------NDSKT
cassava4.1_003595m         ------------------------------------------------
Lus10007913                ------------------------------------------------
Lus10036393                ------------------------------------------------
Thecc1EG005268t1           ------------------------------------------------
Gorai.007G103000.1         ------------------------------------------------
Gorai.004G159800.1         ------------------------------------------------
evm.model.supercontig_184.28 ----------------------------------------------
XP_002275405.2             IYVSTDSVRVAGGVEFEVYEKEEMILCGSLERMESSWGNGSGGLENGSRT
orange1.1g006758m          ------------------------------------------------
Ciclev10019285m            ------------------------------------------------
Glyma09g39090.1            ------------------------------------------------
PGSC0003DMP400000412       ------------------------------------------------
Eucgr.D02321.1             ------------------------------------------------
AT1G01510.1                ------------------------------------------------
LOC_Os10g38900.1           ------------------------------------------------
Sobic.001G316200.1.p       ------------------------------------------------
BAJ89523.1                 ------------------------------------------------
GRMZM2G476107_T01          ------------------------------------------------
BAA25287.1                 ------------------------------------------------
AAC62822.1                 ------------------------------------------------
NP_001185788.1             ------------------------------------------------
NP_001079151.1             ------------------------------------------------
                                ......110.......120.......130.......140.......150

Potri.014G089400.1         ------------------------------------------------
Potri.002G163200.1         ------------------------------------------------
30174.m008658              GWSMECYMAASVGEGNSVFFQPKLGVSAPAIEVYIAGCCGGIPVILTKTI
cassava4.1_003595m         ------------------------------------------------
Lus10007913                ------------------------------------------------
Lus10036393                ------------------------------------------------
Thecc1EG005268t1           ------------------------------------------------
Gorai.007G103000.1         ------------------------------------------------
Gorai.004G159800.1         ------------------------------------------------
evm.model.supercontig_184.28 ----------------------------------------------
XP_002275405.2             GWDMDCYTAASVVAGSSAFFQPKLGVSSPSIEVYIAGCSSSMPVILTKTI
orange1.1g006758m          ------------------------------------------------
Ciclev10019285m            ------------------------------------------------
Glyma09g39090.1            ------------------------------------------------
PGSC0003DMP400000412       ------------------------------------------------
Eucgr.D02321.1             ------------------------------------------------
AT1G01510.1                ------------------------------------------------
LOC_Os10g38900.1           ------------------------------------------------
Sobic.001G316200.1.p       ------------------------------------------------
BAJ89523.1                 ------------------------------------------------
GRMZM2G476107_T01          ------------------------------------------------
BAA25287.1                 ------------------------------------------------
AAC62822.1                 ------------------------------------------------
NP_001185788.1             ------------------------------------------------
NP_001079151.1             ------------------------------------------------
                                ......160.......170.......180.......190.......200
```

Fig. 2B

```
Potri.014G089400.1              ------------------------------------------------
Potri.002G163200.1              ------------------------------------------------
30174.m008658                   LVSPRKKGSRHGMLDAIPEDEEMEK--EHNGDASLRLRKVQIIESEGDDSD
cassava4.1_003595m              ------------------------------------------------
Lus10007913                     ------------------------------------------------
Lus10036393                     ------------------------------------------------
Thecc1EG005268t1                ------------------------------------------------
Gorai.007G103000.1              ------------------------------------------------
Gorai.004G159800.1              ------------------------------------------------
evm.model.supercontig_184.28    ------------------------------------------------
XP_002275405.2                  QISPRQKASRHGMLDAIPEGEEIGKAQENSNGTVRQRKDMVMEFCHDDYE
orange1.1g006758m               ------------------------------------------------
Ciclev10019285m                 ------------------------------------------------
Glyma09g39090.1                 ------------------------------------------------
PGSC0003DMP400000412            ------------------------------------------------
Eucgr.D02321.1                  ------------------------------------------------
AT1G01510.1                     ------------------------------------------------
LOC_Os10g38900.1                ------------------------------------------------
Sobic.001G316200.1.p            ------------------------------------------------
BAJ89523.1                      ------------------------------------------------
GRMZM2G476107_T01               ------------------------------------------------
BAA25287.1                      ------------------------------------------------
AAC62822.1                      ------------------------------------------------
NP_001185788.1                  ------------------------------------------------
NP_001079151.1                  ------------------------------------------------

.....210.......220.......230.......240.......250

Potri.014G089400.1              ------------------------------------------------
Potri.002G163200.1              ------------------------------------------------
30174.m008658                   LEEKTGNRYYSDDMYYGEDGQLTWFNAGVRVGVGIGLGMCLGIGIGVGLL
cassava4.1_003595m              ------------------------------------------------
Lus10007913                     ------------------------------------------------
Lus10036393                     ------------------------------------------------
Thecc1EG005268t1                ------------------------------------------------
Gorai.007G103000.1              ------------------------------------------------
Gorai.004G159800.1              ------------------------------------------------
evm.model.supercontig_184.28    ------------------------------------------------
XP_002275405.2                  SDGKIGHGFHSEDMYSGEDGQLTWFNAGVRVGVGIGLGMCLGIGIGVGLL
orange1.1g006758m               ------------------------------------------------
Ciclev10019285m                 ------------------------------------------------
Glyma09g39090.1                 ------------------------------------------------
PGSC0003DMP400000412            ------------------------------------------------
Eucgr.D02321.1                  ------------------------------------------------
AT1G01510.1                     ------------------------------------------------
LOC_Os10g38900.1                ------------------------------------------------
Sobic.001G316200.1.p            ------------------------------------------------
BAJ89523.1                      ------------------------------------------------
GRMZM2G476107_T01               ------------------------------------------------
BAA25287.1                      ------------------------------------------------
AAC62822.1                      ------------------------------------------------
NP_001185788.1                  ------------------------------------------------
NP_001079151.1                  ------------------------------------------------

```
Potri.014G089400.1              HVSRQR--AKGGGWFLDA SNVTKRDPAAQFLV    KDTIGLRSFAAGGK
Potri.002G163200.1              HVSRQR--VKGGGWFLDAMSNVTKRDPAAQFLV  RSKDTIGLRSFAAGGK
30174.m008658                   HVSRQR--VKGGGWFLDAMSNVTKRDPA SQFLV  RSKDT GLRSFAAGGK
cassava4.1_003595m              HVSRQR--VKGGGWFLDAMSNVTKRDPAAQFLV  RSKDT GLRSFAAGGK
Lus10007913                     HVSRQR--VKGGGWFLDAMS SVTKRDPAAQFLV    KDT T GLRSFAAGGK
Lus10036393                     HVSRQR--VKGGGWFLDAMS SVTKRDPAAQFLV    I T GLRSFAAGGK
ThecclEG005268t1                HVSRQR--VKGGGWFLD MSNVTKRDPAAQFLV  RSKDTIGLRSFAAGGK
Gorai.007G103000.1              H SRQR--VKGGGWFLD MSNVTKRDPAAQFLV  QSKDTIGLRSFAAGGK
Gorai.004G159800.1              HVSRQR--VKGGGWFLDMSNVTKRDPAAQFLV   RNK TIGLRS CAAGGK
evm.model.supercontig_184.28    HVSRQR--VKGGGWFLD MSNVTKRDPAAQFLV   RNK TIGLRSFAAGGK
XP_002275405.2                  HVSRQR--V QGGGWFLDAMSNVTKRDPAAQF KA R SKDTIGLRSFAAGGK
orange1.1g006758m               H SRQR--HKGGGW I L MSNVTKRDPAAQFL C- KSKDTIGLRSF TAGGK
Ciclev10019285m                 H SRQR--HKGGGW I L MSNVTKRDPAAQFL C- KSKDTIGLRSF TAGGK
Glyma09g39090.1                 HVSRQR--VKGGGW I   MSNV KRDPAAQFL    RSKDTIGLRSL AAGGK
PGSC0003DMP400000412            HVSRQR--VKGGGWFLD MSDVTKRDPAAQFLV  SRSKDTIGLRSF TAGGK
Eucgr.D02321.1                  HVSRQR--VKGGGWFLD  SNVTKRDPAAQFLV   RGK TIGLRSFAAGGK
AT1G01510.1                     HVSRQR--TKNGGWFLD   SN KRDPAAQF TA  RNKDT GLRSAAGGK
LOC_Os10g38900.1                HVARER--VAG GWFLDV SKATKRDPAAQFLV TE RNKDT GLRSE VAGGK
Sobic.001G316200.1.p            YVSRER--VAGGG  LDV  PNATKRDPAAQFLV T RNKDTIGLRSE VAGGK
BAJ89523.1                      HVSRER--VAGGG  LDV SNATKRDPAAQFL T  RNKDTIGLRSE VAGGK
GRMZM2G476107_T01               HVARQRV VGGGW  LDV  SNAT NRDPAAQFLV T   NKDT  GLRSE VAGGK
BAA25287.1                      ------------KLQM SNQEK-------------------
AAC62822.1                      P VAHPPHAPSP G----Q  KPEADRD  ASDQL-----------
NP_001185788.1                  P VAHPPHAPSP G----Q  KPEADRD HTSDQL-----------
NP_001079151.1                  A VAHPPHAPSP G----Q  KPEADRD HPSDQL-----------
                                   ......910.......920.......930.......940.......950

Potri.014G089400.1              LLQINRRMEFVF T SHSFDVWESWMLEGSLEE--CRLVNCRNPLA  LDAR  E
Potri.002G163200.1              LLQINRR TEFVFASHSFDVWESWMLEGSLEE--CRLVNCRNPLAVL  VR E
30174.m008658                   LLQINRR TEFVFASHSFDVWESWMLEGSLEE--CRLVNCRNPLAVLDVR E
cassava4.1_003595m              LLQINRRMEFVFASHSFDVWESWMLEGSLEE--CRLVNCRNPLNS    WI E
Lus10007913                     LLQINRRMEFVFASHSFDVWESWMLEG PLEE--CRLVNCRNPLAVLDV  E
Lus10036393                     LLQINRRMEFVFASHSFDVWESWMLEG PLEE--CRLVNCRNPLAVL  VC E
ThecclEG005268t1                LLQINRRMEFVFASHSFDVWESW T  QGPLEE--CRLVNCRNPSA LDH  E
Gorai.007G103000.1              LLQINRRMEFVFASHSFD  WESW T  QGPLEE--CRLVNCRNPSA LDVR E
Gorai.004G159800.1              LLQINRRMEFVFASHSFDVWESW T  QGPLEE--CRLVNCRNPSAVLDVR E
evm.model.supercontig_184.28    LLQINRRMEFVFASHSFDVWESW T  LEGSLEE--CRLVNCRNPLAVL NVS E
XP_002275405.2                  LLQINRRMEFVFASHSFDVWESWMLEGSLEE--CRLVNCRNPLAVLDVR   E
orange1.1g006758m               LLQINRRMEFVFASHSFDAWESW A  EGPLEE--CRLVNCRNPLAF LDVR E
Ciclev10019285m                 LLQINRRMEFVFASHSFDAWESW A  EGPLEE--CRLVNCRNPLAF LDVR E
Glyma09g39090.1                 LLQINRRMEFVFASHSFDVWESWM NWT LEGSL CE--CRLVNCRNPSAVLDVR  E
PGSC0003DMP400000412            LLQINRRMEFVFASHSFDVWESW TFPG   EE--CRLVNCRNPLAVLDVR E
Eucgr.D02321.1                  LLQINRRMEFVFASHSFDVWESW T  LEGSL E--C RLVNCRN SCAVL  VR  E
AT1G01510.1                     LLQINRRMEFVFASHSFDVWESW S LEGSL  E--CRLVNCRN SSAVLDVR  E
LOC_Os10g38900.1                LLQ N  T ME LVFAS YSFDVWESW T  LEGSLL Q C LVNRK T P SVVL  VYI E
Sobic.001G316200.1.p            LLQ ANN  MEFVF T SHSFDV C ESWMLEGSLSE C  LVNR NS LAV I  VYI E
BAJ89523.1                      LLQ N  K A ELVFANH APDVWESW T  LEGSLLEC  LVNHRNPLAV I  VYI E
GRMZM2G476107_T01               LLQINPR MEFVFASHSFDVWESWM  GS I L EGSL   NCRNPSAVLD  CI E
BAA25287.1                      ----------------------------------------
AAC62822.1                      ----------------------------------------
NP_001185788.1                  ----------------------------------------
NP_001079151.1                  ----------------------------------------
                                   ......960.......970.......980.......990.......1000
```

Fig. 2J

| | |
|---|---|
| Potri.014G089400.1 | ILAALAEDGVTRWLD------- |
| Potri.002G163200.1 | ILAAVGE-DGVSRWLD------- |
| 30174.m008658 | VLAAVGE-DGVTRWLD------- |
| cassava4.1_003595m | FS---------------------- |
| Lus10007913 | ILAAVGE-DGVTRWLD------- |
| Lus10036393 | ILAAVGE-DGVTRWLD------- |
| Thecc1EG005268t1 | ILAAVGE-DGVTRWLD------- |
| Gorai.007G103000.1 | ILAAVGE-DGVTRWLD------- |
| Gorai.004G159800.1 | ILAAIGE-DGVTRWLD------- |
| evm.model.supercontig_184.28 | ILAVTGE-DGVMRWLE------- |
| XP_002275405.2 | ILAAVGE-DGVTRWLD------- |
| orange1.1g006758m | ILAAVGE-DGITRWLD------- |
| Ciclev10019285m | ILAAVGE-DGITRWLD------- |
| Glyma09g39090.1 | ILATVGE-DGVTRWLE------- |
| PGSC0003DMP400000412 | VLAAVGE-DGITRWLD------- |
| Eucgr.D02321.1 | ILAVVGE-DGITRWLD------- |
| AT1G01510.1 | ILAMVG--DGITRWLD------- |
| LOC_Os10g38900.1 | ILAAVSE-DGVTRWLD------- |
| Sobic.001G316200.1.p | VLGAPS-EDGVVRWLD------- |
| BAJ89523.1 | ILAAVSE-DGVTRWLD------- |
| GRMZM2G476107_T01 | ILAAPSE-DGVTRWLDSPRWGL |
| BAA25287.1 | ------------------------ |
| AAC62822.1 | ------------------------ |
| NP_001185788.1 | ------------------------ |
| NP_001079151.1 | ------------------------ |
| | ......1010......1020.. |

Fig. 2K

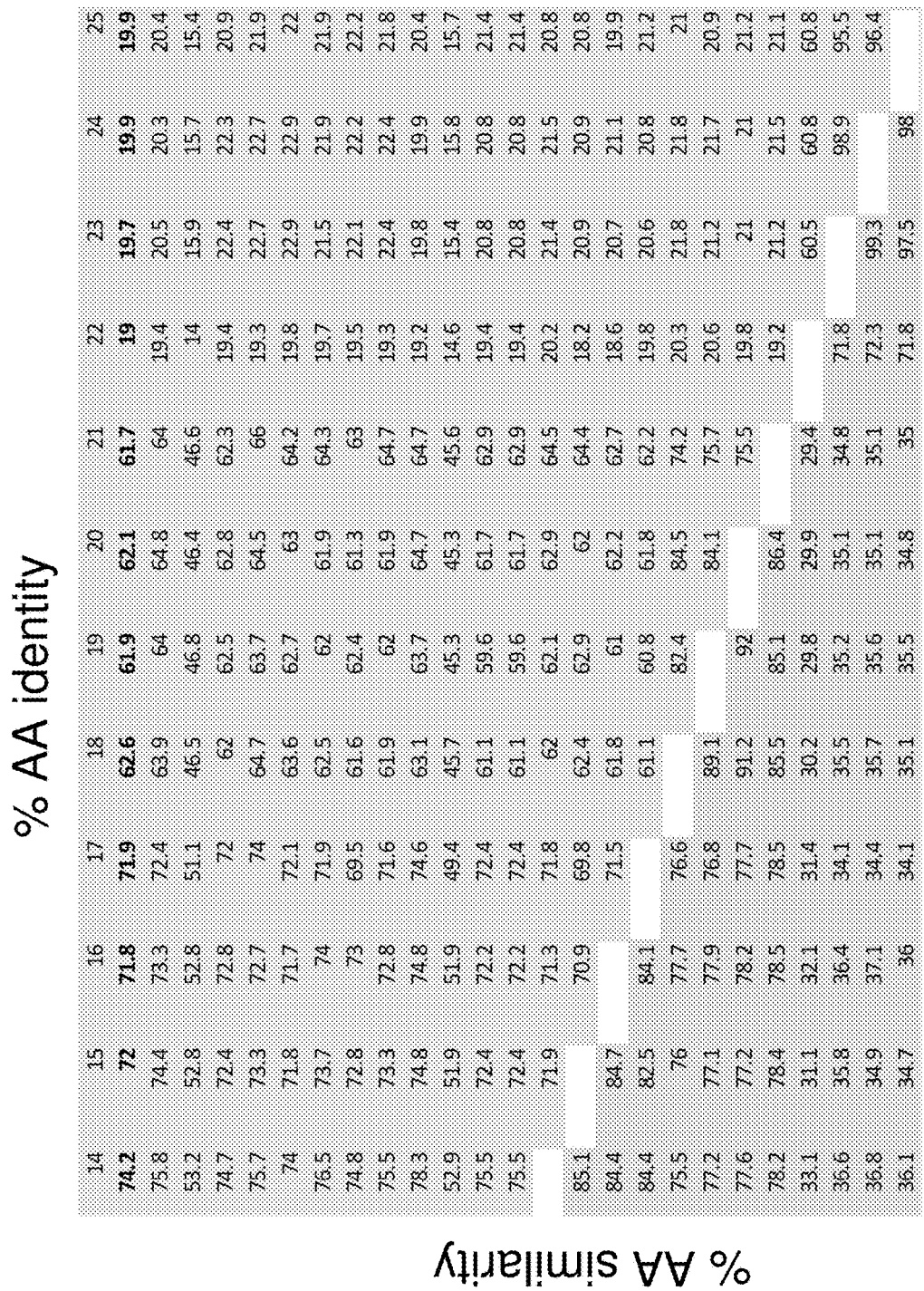
Fig. 3 (con't)

MSATTTRSLATMSHRRNTNTPPPPQQQQQQQQQQQRLPLVVTLNCIEDFAIEQDSLSGVALIEHVPLGRL

SDGKIESAAAVLLHSLAYLPRAAQRRLRPYQLILCLGSADRAVDSALAADLGLRLVHVDTSRAEEIADTV

MALFLGLLRRTHLLSRHALSASGWLGSLQPLCRGMRRCRGLVLGIVGRSASARSLATRSLAFKMSVLYFD

VHEGPGKLTRSSITFPLAARRMDTLNDLLAASDLISLHCALTNETVQIINEECLQHIKPGILLSLLILRR

AFLVNTGSSQLLDDCALKQLLIDGTLAGCALDGAEGPQWMEAWVKEMPNVLILPRSADYSEEVWMEIREK

AISILQSFFFDGIVPKNAVSDEEGEESEIGDESEQFHRQDKESTLQDSVGEQLTDDIQLTPETSRKKVSG

QSIESTSQAQGSGMSQNTTTRSDERRSRSGKKAKKRHGRQKPRQKSDNPSQLEKESTSHQEDDTAMSGSD

QVSSSRFASPEDSRSRKTPIELMQESSSGQLSRSGKRLSGKSDELLKDGHIIALYARDRPALHVSRQRAK

GGGWFLDALSNVTKRDPAAQFLVVFRNKDTIGLRSFAAGGKLLQINRRMEFVFTSHSFDVWESWMLEGSL

DECRLVNCRNPLAILDARVEILAAIAEDDGVTRWLD

Fig. 6

KEY GENE REGULATING PLANT CELL WALL RECALCITRANCE

CROSS REFERENCE TO RELATED APPLICATIONS

This application claims priority from U.S. Provisional Application No. 61/968,291 filed Mar. 5, 2014, the entire contents of which are incorporated herein by reference.

STATEMENT REGARDING FEDERALLY SPONSORED RESEARCH OR DEVELOPMENT

This disclosure was made with government support under a research project supported by Contract No. DE-AC05-00OR22725 awarded by the U.S. Department of Energy. This work was conducted under the DOE BioEnergy Science Center (BESC). The government has certain rights in this disclosure.

INCORPORATION BY REFERENCE OF SEQUENCE LISTING

The Sequence Listing in the ASCII text file, named as 29244_SequenceListing_rev.txt of 4-46152 KB, created on Nov. 4, 2015, and submitted to the United States Patent and Trademark Office via EFS-Web, is incorporated herein by reference.

BACKGROUND OF THE DISCLOSURE

Production of renewable fuel from lignocellulosic plant biomass is based on extraction of sugars from plant cell wall material. This extraction process is hampered by the presence of lignin in the cell wall. Lignins contribute to plant "recalcitrance", a term referring to the inherent resistance of plant material to release polysaccharides and other desirable biomaterials from an interwoven matrix of desirable and undesirable materials (Lynd L R. et al., *Science* 251:1318-1323 (1991)). Lignins are difficult to break down by physical, chemical and other methods, and processing plant materials to release sugars from lignins requires extensive thermochemical or enzymatic treatment. In addition, lignin processing creates inhibitory byproducts, such as acetylated compounds, that hamper further extraction and fermentation. Acetyl esters released during treatment of cell wall polymers can inhibit saccharification of biomass. The released acetate is also inhibitory to the organisms used to ferment the sugars into useful byproducts. Overcoming plant recalcitrance to releasing biomaterials bound in the cell wall is therefore an issue of primary importance in the development of biofuel technology.

Lignins, complex interlinking biopolymers derived from hydroxyphenylpropanoids, provide rigidity and structure to plant cell walls for plant growth and transport of water and nutrients, and are significant contributors to plant recalcitrance. Lignins are composed primarily of syringyl (S), guaiacyl (G) and p-hydroxyphenyl (H) monolignol subunits, which are derived from sinapyl, coniferyl and p-coumaryl alcohols, respectively. The S/G subunit ratio and resulting structure of plant lignins varies according to the genotype, environment, tissue type and maturity of the plant and as such, lignins are very heterogeneous and can vary significantly between different plants, within different tissues of a single plant and even within a single plant cell (Simmons B A et al., *Curr Opin Plant Biol.* 13:313-20 (2010)). This complexity and heterogeneity hinders the development of conversion technology able to process a range of sustainable feedstocks in a cost-effective manner.

Reduction of lignin biosynthesis, and decreases in cell wall recalcitrance, is desirable on one hand for biofuel production as well as production of cellulose-based products such as pulp and paper. Conversely, increases in cell wall recalcitrance and lignin biosynthesis can be desirable for production of lignin-based products such as carbon fibers. Thus, genetic manipulation of biomass feedstock to modulate lignin biosynthesis and S/G ratio hold promise both for production of improved, economically sustainable lignocellulosic biofuels (Vermerris W. et al., *Crop Science* 47(53): 5142-5153 (2007); Fu C. et al., *PNAS* 108:3803-3808 (2011)), and for creating improved cellulose-based products.

The genus *Populus* represents an economically important tree crop that has been targeted for use in diverse applications from the pulp and paper industry, carbon sequestration and as a feedstock in the lignocellulosic biofuel industry (Dinus R J. et al., *Crit. Rev. Plant Sci.* 20:51-69 (2001)). Recently, a study using wild *Populus trichocarpa* genotypes collected in the Pacific Northwest region demonstrated high phenotypic variation among the accessions in recalcitrance measured by lignin content and sugar release (Studer M H. et al., *PNAS* 108:6300-6305 (2011)). This study suggested that sufficient variation occurs in wild germplasm to identify specific genetic determinants of the recalcitrance trait by analysis of naturally-occurring allelic variability.

Quantitative trait loci (QTL) studies have been conducted using interspecific mapping of populations to identify genomic regions associated with cell wall phenotypes linked to recalcitrance (Novaes E. et al., *New Phytologist* 182:878-890 (2009); Yin T. et al., *PLoS one* 5:e14021 (2010)). Wegrzyn J L. et al., *New Phytologist* 188:515-532 (2010) demonstrated the feasibility of using linkage disequilibrium (LD)-based association mapping to validate candidate genes with putative functions in cell wall biosynthesis. The extent of LD decay in *P. trichocarpa* has been described by Slavov G T. et al., *New Phytologist* 196(3):713-25 (2012), who reported LD decay to below $r^2$=0.2 within 2 kb in more than half of the genes, within a genomewide average 6-7 kb. Given that the average gene size for *P. trichocarpa* is 5 kb, these results suggest that QTL fine-mapping and association mapping to within single-gene resolution is possible in *P. trichocarpa*.

Identification and manipulation of genes regulating cell wall biosynthesis and recalcitrance is critical both for efficient production of cellulosic sugars and ethanol from plant biomass, and for production of improved cellulose-based products, such as paper and pulp.

BRIEF SUMMARY OF THE DISCLOSURE

This disclosure provides plants having preferred levels of lignin synthesis, sugar release, S/G ratio, and resistance to stress and pathogens; methods of selecting plants with preferred levels of lignin synthesis, sugar release, S/G ratio, and resistance to stress and pathogens; methods of genetically modifying plants to modulate lignin synthesis, sugar release, S/G ratio, and resistance to stress and pathogens; and uses of such plants. The inventors have determined that the expression and/or activity of POPTR_0014s08530 (also referred to as Potri.014G089400), a gene encoding an *Angustifolia* transcription factor, modulates lignin synthesis, sugar release, S/G ratio, and resistance to stress and pathogens in plants. Plants with improved lignin synthesis, sugar release, S/G ratio, and resistance to stress and pathogens, based on modulation of the expression or activity of the POPTR_0014s08530 gene, have divergent uses including pulp and paper production, lignin-based carbon fibers, engineering of pathogen- and drought-resistant strains, and ethanol/biofuel production.

In one embodiment, methods of selecting a plant for a lignin biosynthesis characteristic are provided. The methods include the steps of (a) obtaining nucleic acids from a candidate plant; (b) identifying an allelic variant of the POPTR_0014s08530 gene in the nucleic acids; and (c) selecting a plant based on the presence of an allelic variant of the POPTR_0014s08530 gene in the nucleic acids obtained from the plant. The lignin biosynthesis characteristic can be high or low expression of an enzyme in the lignin synthesis pathway.

Another embodiment provides methods to detect the presence of an allelic variant of POPTR_0014s08530 in a plant. The method involves identifying a plant with high or low lignin levels, or increased S/G ratios, and determining the sequence of the gene at the POPTR_0014s08530 locus in said plant.

An allelic variant or homolog of POPTR_0014s08530 can encode a protein having the amino acid sequence of SEQ ID NO: 2, or an amino acid sequence with at least one amino acid alteration or deletion relative to the sequence of SEQ ID NO: 2. The allelic variant or homolog can encode a protein having at least 75%, 80%, 85%, 90%, 95%, 98%, or 100% sequence identity to SEQ ID NO: 2. The allelic variant or homolog can encode a polypeptide with an increased or decreased number of glutamine residues relative to the number of glutamine residues at positions 25-36 of SEQ ID NO: 2. An example of an allelic variant with an increased number of glutamine residues relative to the sequence of SEQ ID NO: 2 is SEQ ID NO: 1. Methods to determine nucleic acid sequences are known in the art and include, for example, polymerase chain reaction and nucleic acid hybridization.

Further disclosed herein are nucleic acid inhibitors of expression of POPTR_0014s08530, or inhibitors of expression of allelic variants of POPTR_0014s08530 including SEQ ID NO: 2, which can be used to reduce expression of the POPTR_0014s08530 gene and allelic variants thereof, to reduce lignin biosynthesis. Specific nucleic acid inhibitors include antisense RNA, small interfering RNA, RNAi, microRNA, artificial microRNA, and ribozymes. Inhibitors of POPTR_0014s08530 activity include expression vectors encoding the polypeptide of SEQ ID NO: 4, operably linked to a regulatory region that is functional in a plant. Also disclosed herein are plants and plant cells genetically modified by introduction of the disclosed inhibitors and expression vectors. Expression of such inhibitors and expression vectors in a plant or plant cell can be used in methods to increase glucose and/or xylose release in a plant or plant cell, to decrease lignin synthesis, or to increase resistance to environmental stress and pathogens, in such genetically modified plants and plant cells. Further disclosed herein are improved methods of producing biofuel from cellulosic biomass, by using plants with reduced or inhibited expression or activity of the POPTR_0014s08530 gene in biofuel production processes.

This disclosure further provides expression vectors with a nucleotide sequence encoding the polypeptide of SEQ ID NO: 2, or another allelic variant of POPTR_0014s08530, operably linked to a regulatory region that is functional in a plant. The regulatory region can be an inducible promoter or a tissue-specific promoter, for example, a xylem-specific promoter. Further provided herein are plants and plant cells genetically modified by introduction of such expression vectors, and methods for increasing lignin synthesis in a plant or plant cell by expressing such expression vectors in a plant or plant cell of interest.

Additionally disclosed are methods of producing paper and pulp, by using plants with increased expression of the POPTR_0014s08530 gene in paper or pulp production processes. Further disclosed are pulp and paper products produced by this method, using plants with increased expression of the POPTR_0014s08530 gene.

BRIEF DESCRIPTION OF THE FIGURES

FIGS. 1A-1B. Amino acid sequence comparison of *Populus trichocarpa* Allele A, Potri.014G089400_A (SEQ ID NO: 4); Allele B, Potri.014G089400_B (SEQ ID NO: 2); the *Populus* paralog Potri.002G163200 (SEQ ID NO: 5); and the *Arabidopsis thaliana* homolog At1g01510 (SEQ ID NO: 6).

FIGS. 2A-2K. Amino acid sequence comparison shows conservation of *Angustifolia* proteins across species. (A-K), Ptr_14G089400, *Populus trichocarpa* allelic variant (SEQ ID NO: 39); Ptr_2G163200, *Populus* paralog Potri.002G163200 (SEQ ID NO: 5); Rco_30174.m008658 (SEQ ID NO: 7), *Ricinus communis*; Mes_cassava4.1_003595m (SEQ ID NO: 8), *Manihot esculata* (Cassava); Lus10007913 (SEQ ID NO: 9) and Lus10036393 (SEQ ID NO: 10), *Linum usitatissimum*; Tca_Thecc1EG005268t1 (SEQ ID NO: 11), *Theobroma cacao*; Gra_Gorai.007G103000.1 (SEQ ID NO: 12) and Gra_Gorai.004G159800.1 (SEQ ID NO: 13), *Gossypium raimondi*; Cpa_evm.model.supercontig_18428 (SEQ ID NO: 14), *Carica papaya*; Vvi_XP_002275405.2 (SEQ ID NO: 15), *Vitis vinifera*; Csi_orange1.1g006758m (SEQ ID NO: 16), *Citrus sineasis*; Ccl_Cic1ev10019285m (SEQ ID NO: 17), *Citrus clementine*; Gma_Glyma09g39090.1 (SEQ ID NO: 18), *Glycine max*; Stu_PGSC0003DMP400000412 (SEQ ID NO: 19), *Solanum tuberasum*; Egr_Eucgr.D02321.1 (SEQ ID NO: 20), *Eucalypltus grandis*; Ath_AT1G01510.1 (SEQ ID NO: 6), *Arabidopsis thaliana*; Osa_LOC_Os10g38900.1 (SEQ ID NO: 21), *Oryza sativa*; Sbi_Sobic.001G316200.1.p (SEQ ID NO: 22), *Sorghum bicolor*; Hvu_BAJ89523.1 (SEQ ID NO: 23), *Hodeum vulgare*; Zma_GRMZM2G476107_T01 (SEQ ID NO: 24), *Zea mays*; Dm_BAA25287.1 (SEQ ID NO: 25), *Drosophila melanogaster*; Hs_AAC62822.1 (SEQ ID NO: 26), *Homo sapiens*; Mm_NP_001185788.1 (SEQ ID NO: 27), *Mus musculus*; X1_NP_001079151.1 (SEQ ID NO: 28), *Xenopus laevis*.

Potri.011G069600), a gene involved in cellulose biosynthesis, and *P. trichocarpa* caffeoyl CoA 3-O-methyltransferase-1 (PtrCCoAOMT1; Potri.009G099800), an enzyme involved in lignin biosynthesis, was compared between plants transfected with Allele A, Allele B, or the negative control gene, with expression of PtrCesA8 and PtrCCoAOMT1 in the control plants normalized to 1. (A), Cellulose synthesis is increased in protoplasts overexpressing Allele A ("A") relative to cellulose synthesis in protoplasts overexpressing Allele B ("B") or overexpressing the control gene ("C"). (B), Lignin synthesis is increased in protoplasts with overexpression of Allele B ("B") relative to overexpression of Allele A ("A") or controls. Therefore, allele A is the desirable version for biofuel productions since it results in increased cellulose synthesis, lower lignin content and a high S/G ratio whereas allele B is the desirable version for lignin-based products since it results in enhanced lignin content.

Figure 5:
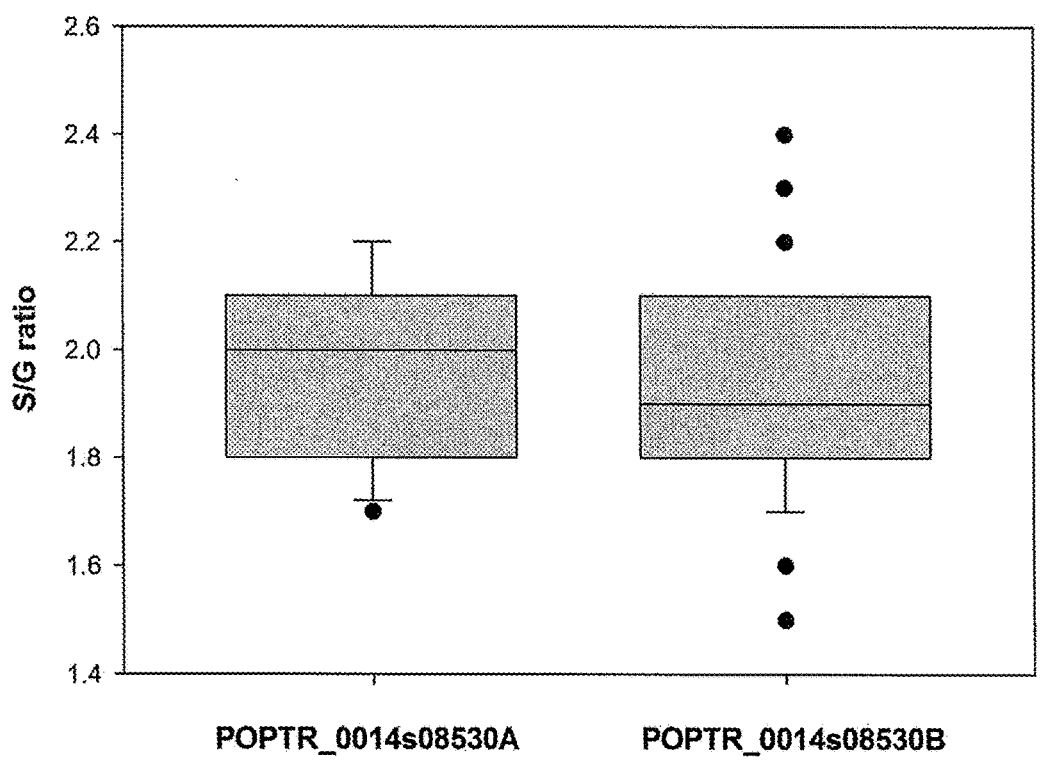

FIG. 5. Allele A shows a higher ratio of S/G monolignol subunits than Allele B. Allelic groups representing POPTR_0014s08530A or POPTR_0014s08530A were pooled, and the S/G average of each group was calculated (represented by the line within each gray box). In this case, allele POPTR_0014s08530A results in a higher S/G ratio on average (2.0) compared to allele POPTR_0014s08530B (1.9). The spots represent group outliers and also show the complete range of values in each grouping.

FIG. 6. Amino acid sequence of a *Populus trichocarpa* allelic variant (Seq ID NO: 39), showing conserved regions as follows: single underlined residues, poly-Q repeat region; double underlined residues, Retinoblastoma binding site; dashed underlined residues, homology to 2-Hacid_DH domain (CtBP domain in animals); boxed region, putative nuclear localization signal.

DETAILED DESCRIPTION OF THE DISCLOSURE

Disclosed herein are plants having desirable levels of lignin synthesis, sugar release, S/G ratio, and resistance to stress and pathogens; methods of selecting plants with preferred levels of lignin synthesis, sugar release, S/G ratio, and resistance to stress and pathogens; methods of genetically modifying plants to modulate lignin synthesis, sugar release, S/G ratio, and resistance to stress and pathogens; and uses of such plants. The inventors have identified a gene, denoted POPTR_0014s08530, with allelic variants including SEQ ID NO: 2 and SEQ ID NO: 4, that modulates lignin synthesis, sugar release, S/G ratio, and resistance to stress and pathogens in plants. POPTR_0014s08530 encodes an *Angustifolia*/C-terminal Binding Protein (CtBP) transcription factor. Plants with modulated (increased or decreased) lignin synthesis, sugar release, S/G ratio, and resistance to stress/pathogen characteristics, based on modulation of the expression or activity of the POPTR_0014s08530 gene, have divergent uses including pulp and paper production, ethanol/biofuel production, and engineering of drought- and pathogen-resistant crops.

The inventors have discovered new naturally occurring alleles in *Populus trichocarpa* associated with cell wall phenotypes. A QTL for lignin biosynthesis and S/G ratio in *P. trichocarpa* was mapped in this study to POPTR_0014s08530 (also referred to as Potri.014G089400), encoding an *Angustifolia*/CtBP transcription factor. The inventors have determined that altered expression of this gene, either to increase or decrease levels of the functional protein product, leads to a plant with desirable cell wall chemistry suitable for uses including biofuel production and pulp production.

POPTR_0014s08530 is related to the animal C-terminal Binding Protein (CtBP/BARS), which is known to function as a corepressor. Plant homologs of CtBP are monophyletic compared to animal homologs and contain an added C-terminal extension not seen in animal CtBP. The *Arabidopsis thaliana* homolog has been previously characterized and named *Angustifolia* (AN). A discerning characteristic of POPTR_0014s08530, compared to the *Populus* paralog and other AN/CtBP proteins, is the presence of a long repeated region of glutamines (poly-Qs) just upstream of the LNCIE amino acid consensus residues forming the proposed binding site of the Retinablastoma protein. Null an mutants in *Arabidopsis* (AtAN) display narrow cotyledons and rosette leaves, reduced growth and delayed flowering. This narrow leaf phenotype attributed to misregulation of polar elongation in leaf epidermal cells (Tsuge, T, et al., *Development*, 122:1589-1600 (1996)). AtAN has been further demonstrated to regulate cortical microtubule arrangements in epidermal cells (Kim, G-T, et al., *The EMBO J* 21:1267-1279 (2002)). This association is of great interest to cell wall chemistry in that previous analysis demonstrated the involvement of cortical microtubules in regulating cellulose microfibril insertion in the cell wall through determining the insertion of the cellulose synthase complexes into the cell membrane (Crowell, E, et al., *The Plant Cell*, 21:1141-1154 (2009)), The inventors provide evidence herein for roles of the *Populus* AN gene in cell wall chemistry. Without being limited, it is believed that POPTR_0014s08530 can act as a repressor, similar to the function of the animal homolog CtBP, in that POPTR_0014s08530 can increase expression of several genes including the upregulation of a xyloglucan endotransglucosylase/hydrolase, MERI5, thought to be involved in loosening the cell wall. The inventors have shown that POPTR_0014s08530 allelic variants have reduced lignin content compared to wild type plants.

Variants of POPTR_0014s08530 can be utilized for response to biotic and abiotic stresses. "Biotic" stresses include pathogens that attack plants; "abiotic" stresses include dehydration/drought, lack of sunlight, lack of nutrients, poor soil conditions, elevated temperatures, etc. Null POPTR_0014s08530 homologs in *Arabidopsis* were shown to have a higher accumulation of reactive oxygen species compared to wild type plants as well as an increased expression of stress responsive genes (Gachomo, E, et al., *BMC Plant Biology*, 13(79):1-11 (2013)). Similar to AtAN mutants, plants expressing allelic variants or homologs of POPTR_0014s08530 will be more resistant to both dehydration as well as bacterial stress.

POPTR_0014s08530 Alleles and Sequences

The inventors have studied in detail the effects of two naturally-occurring alleles of the AN transcription factor. These alleles are allele A (also referred to herein as POPTR_0014s08530A or Potri.014G089400_A), and allele B (also referred to herein as POPTR_0014s08530B or Potri.014G089400_B). The nucleic acid sequence of allele B is provided as SEQ ID NO: 1. The amino acid sequence of allele B is provided as SEQ ID NO: 2. The nucleic acid sequence of allele A is provided as SEQ ID NO: 3. The amino acid sequence of allele A is provided as SEQ ID NO: 4.

cDNA sequencing for POPTR_0014s08530A revealed an increase in glutamine repeats ("poly-Q" repeats) relative to the B allele. Plants with allele A showed markedly reduced activation of the lignin biosynthetic pathway relative to plants with allele B.

Allelic Variants and Homologs of POPTR_0014 s08530

As used herein, "allelic variants" are alternative forms of the same gene or genetic locus. Each allelic variant has a distinct nucleic acid sequence at the locus of interest. For example, the inventors have discovered two allelic variants of the POPTR_0014s08530 gene, the nucleic acid sequences of which differ from each other by at least one nucleotide. Allelic variants of POPTR_0014s08530 include SEQ ID NO: 1 and SEQ ID NO: 3. An allelic variant of the POPTR_0014s08530 gene can have at least one nucleic acid alteration or deletion relative to the sequence of SEQ ID NO: 1 or SEQ ID NO: 3, and can encode a polypeptide that differs by one or more amino acids from SEQ ID NO: 2 or SEQ ID NO: 4. Allelic variants can encode different proteins when the difference in nucleic acid sequence results in at least one alteration or deletion in the amino acid sequence between the variants. The allelic variant can encode a polypeptide with a different number of glutamine repeats relative to the sequence of SEQ ID NO: 2. A specific example of an allelic variant with a different number of glutamine repeats, relative to the sequence of SEQ ID NO: 2, is SEQ ID NO: 4.

An allelic variant of POPTR_0014s08530 can encode the amino acid sequence as set forth in SEQ ID NO: 2, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 2 or SEQ ID NO: 4. Sequence identity refers to the percent of exact matches between the amino acids of two sequences which are being compared. Where one allelic variant encodes a truncated protein relative to the protein encoded by another allelic variant, percent identity can be determined by comparing the amino acid sequences of the variants along the length of the shorter protein.

This disclosure also provides homologs of the polypeptide encoded by POPTR_0014s08530. A POPTR_0014s08530 homolog can be a homolog, ortholog or variant of the polypeptide having the amino acid sequence set forth in SEQ ID NO: 2 or SEQ ID NO: 4. For example, a POPTR_0014s08530 homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO:1.

In some embodiments, a homolog of POPTR_0014s08530 is a functional homolog. A functional homolog is a polypeptide that has sequence similarity to SEQ ID NO: 2 or SEQ ID NO: 4 and that carries out one or more of the biochemical or physiological function(s) of the polypeptide of SEQ ID NO: 2 or SEQ ID NO: 4. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

A homolog of POPTR_0014s08530 can be a native POPTR_0014s08530 protein, i.e., one or more additional copies of the coding sequence for a POPTR_0014s08530 homolog that is naturally present in the cell. Alternatively, a homolog of POPTR_0014s08530 can be heterologous to the cell, e.g., a transgenic *Populus* plant can contain the coding sequence for a POPTR_0014s08530 homolog from an *Arabidopsis* plant, for example. POPTR_0014s08530 homologs from multiple species are identified in FIGS. 2A-2K, and provided in SEQ ID NOS: 5-28.

Allelic Variation and Modulation of the POPTR_0014s08530 Gene is Associated with Altered Lignin Synthesis, Sugar Release, S/G Ratio, and Resistance to Environmental Stress and Pathogens This disclosure further provides for modulation of the POPTR_0014s08530 gene. "Modulation" refers to changing the expression or activity of the POPTR_0014s08530 gene.

One specific form of modulation is altering the number of glutamine repeats near the N-terminal end of the POPTR_0014s08530 polypeptide, to create an allelic variant with an increased or decreased number of adjacent glutamines relative to the number of glutamines (13) at residues 24-36 of SEQ ID NO: 2. For example, the nucleic acid sequence of a POPTR_0014s08530 allelic variant can be designed to encode a polypeptide with no glutamine residues at the positions corresponding to residues 24-36 of SEQ ID NO: 2, or with 1, 2, 3, 4, 5, 6, 7, 8, 9, 10, 11, 12, 13, 14, 15, 16, 17, 18, 19, 20, 21, or 22 or more glutamines at the positions corresponding to residues 24-36 of SEQ ID NO: 2. These glutamines occur adjacent to a consensus binding site (LNCIE) for the Retinoblastoma (Rb) protein. Another form of modulation is to alter the Rb binding site, the CtBP domain, and/or the nuclear localization signal (identified in FIG. 6). A region with homology to 2-Hacid_DH (the CtBP domain in animal homologs) is found at positions corresponding to residues 116 to 327 of SEQ ID NO: 2.

The POPTR_0014s08530 gene can also be modulated by increasing or decreasing expression of the gene itself. Methods to modulate expression are disclosed in detail below.

Allelic variation and modulation of the POPTR_0014s08530 gene can lead to proteins with altered activity. "Altered activity" includes an increase or decrease in a known activity of a protein encoded by a gene of interest, including loss of an established or proposed function, or gain of a new function. For example, the inventors have discovered that plants harboring Allele A of the POPTR_0014s08530 gene have low lignin biosynthesis relative to POPTR_0014s08530 Allele B plants. Thus, the A allelic variant has reduced lignin biosynthetic activity relative to the B allelic variant. Conversely, the B allelic variant can be seen to have increased lignin biosynthetic activity relative to the A allelic variant. As the POPTR_0014s08530 gene encodes an *Angustifolia*/CtBP transcription factor, activities that can be altered for this gene include, but are not limited to, DNA binding, activation of one or more downstream genes, and binding to one or more co-factors.

The inventors have determined that allelic variants of the POPTR_0014s08530 gene have altered S/G ratios, distinctive sugar release characteristics, and distinctive lignin synthesis characteristics, that produce plants with desirable qualities. The inventors have further determined that manipulating the POPTR_0014s08530 gene, for example, by manipulating the expression of the POPTR_0014s08530 gene or by increasing or decreasing the number of glutamine repeats in the protein, can modulate S/G ratio, sugar release, and/or lignin content.

Altered S/G ratios in a plant (e.g., *Populus* species) include, for example, alterations from essentially 50% syringyl ("S"):50% guaiacyl ("G") units to essentially 100% syringyl units, or essentially 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc; or less than 2:1, e.g., 0.5:1, 0.8:1, 1:1, 1.2:1, 1.5:1, 1.8:1, or 2:1.3, 2:1.5, 2:1.7, 2:1.9, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant (i.e., without the manipulation of the POPTR_0014s08530 gene). In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

By manipulating the POPTR_0014s08530 gene, the amount and/or rate of S subunit to G subunit biosynthesis, or the incorporation of S to G subunits into the lignin structure, can be altered. Alteration in the S/G subunit ratio alters the lignin composition of the plant cell wall. Manipulating the POPTR_0014s08530 gene can thus modulate the lignin composition of a plant.

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant. "Low" sugar release (i.e., high recalcitrance) means that sugar can be extracted less easily, or less sugar can be extracted, from a plant, under conditions that would result in more sugar release in a plant without the particular allelic variant. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and β-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular POPTR_0014s08530 allelic variant, relative to sugar release or sugar recovery from a plant that does not have the POPTR_0014s08530 allelic variant. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

"Lignin" is a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

Lignin "synthesis" or "biosynthesis" refers to the production of lignin in a plant, plant tissue, or plant cell. "Lignin synthesis characteristics" or "lignin biosynthesis characteristics" include the total amount of lignin ("lignin content") in a plant or plant cell, the ratio or amount of monolignol subunits, and expression and/or activity of lignin biosynthetic enzymes. Lignin content, ratio or amount of monolignols, and expression and/or activity of lignin biosynthetic enzymes, can be affected by allelic variation in the POPTR_0014s08530 gene, where one or more of these characteristics can be high or low relative to the same characteristic or characteristics in a plant that does not have the same POPTR_0014s08530 allelic variant.

Enzymes in the lignin synthesis pathway that can show high expression, high activity, low expression, or low activity, depending on the allelic variant of POPTR_0014s08530 present in the plant, include, but are not limited to, phenylalanine ammonia lyase (PAL), cinnamate 4-hydroxylase (C4H), 4-coumarate coenzyme A ligase (4CL), ferulate 5-hydroxylase (F5H), p-coumarate 3-hydroxylase (C3H), p-hydroxycinnamoyl-CoA:quinate/shikimate hydroxycinnamoyl transferase (HCT), caffeoyl-CoA O-methyltransferase (CCoAOMT), cinnamoyl-CoA reductase (CCR), caffeic acid O-methyltransferase (COMT), and cinnamyl alcohol dehydrogenase (CAD).

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation.

Plants harboring Allele A have characteristics of low lignin synthesis activity (see FIG. 4) and high sugar release relative to plants harboring the B allele.

Variants of POPTR_0014s08530, particularly variants with increased glutamine repeats relative to the number of glutamine repeats in SEQ ID NO: 2, have improved resistance to stress, specifically environmental stress, and pathogens. Environmental stresses include dehydration/drought, lack of sunlight, lack of nutrients, poor soil conditions, elevated temperatures, etc. Pathogens include, but are not limited to, single stranded RNA viruses (with and without envelope), double stranded RNA viruses, and single and double stranded DNA viruses such as (but not limited to) tobacco mosaic virus, cucumber mosaic virus, turnip mosaic virus, turnip vein clearing virus, oilseed rape mosaic virus, tobacco rattle virus, pea enation mosaic virus, barley stripe mosaic virus, potato viruses X and Y, carnation latent virus, beet yellows virus, maize chlorotic virus, tobacco necrosis virus, turnip yellow mosaic virus, tomato bushy stunt virus, southern bean mosaic virus, barley yellow dwarf virus, tomato spotted wilt virus, lettuce necrotic yellows virus, wound tumor virus, maize steak virus, and cauliflower mosaic virus. Other pathogens within the scope of the invention include, but are not limited to, fungi such as *Cochliobolus carbonum*, *Phytophthora infestans*, *Phytophthora sojae*, *Collesosichum*, *Melampsora lini*, *cladosporium fulvum*, *Heminthosporium maydia*, *Peronospora parasitica*, *Puccinia sorghi*, and *Puccinia polysora*; bacteria such as *Phynchosporium secalis*, *Pseudomonas glycinea*, *Xanthomonas oryzae* and *Fusarium oxyaporium*; and nematodes such as *Globodera rostochiensis*.

Measuring Lignin Synthesis

Methods to determine if a plant has altered lignin synthesis include, for example, directly measuring lignin content, or by determining the expression or activity of genes in the lignin biosynthetic pathway. Lignin content can be measured directly, for example, by thioglycolysis, or by histochemical analysis of tissue sections stained with toluidine blue 0 (TBO), Wiesner reagent, or Maiule reagent to identify lignified or non-lignified cell walls. Liginin may also be measured by pyrolysis vapor analysis using pyrolysis Molecular Beam Mass Spectrometry (py-MBMS) (Evans R J. et al., *Energy and Fuels* 1:123-137 (1987); Sykes R. et al., *Biofuels: Methods and Protocols* 169-183 (2009); Tuskan G. et al., *Appl. Biochem. Biotechnol.* 77:55-65 (1999)). Additional methods of measuring carbohydrate and lignin content in biomass are known in the art; see, for example, Sluiter A. et al., Determination of structural carbohydrates and lignin in biomass—laboratory analytical procedure. Technical Report NREL/TP-510-42618:1-17 (2008), available from the National Renewable Energy Laboratory.

Levels of lignin content, or levels of a monolignol (e.g., levels of syringyl, guaiacyl, or p-hydroxyphenyl monolignols), in a plant having an allelic variant of POPTR_0014s08530 can be higher or lower, e.g., by 5%, 10%, 15%, 20%, 25%, 30%, 35%, 40%, 45%, 50%, 60%, 70%, 80%, 90%, 100% or more than 100%, as compared to the corresponding levels of lignin synthesis or monolignol content in a plant without the same POPTR_0014s08530 allelic variant. In one example, lignin content is determined by py-MBMS. In this example, "low" lignin content can be less than 5%, less than 10%, less than 15%, less than 20%, or less than 25%. "High" lignin content can be greater than 20%, greater than 25%, greater than 27%, or greater than 30%.

In a preferred embodiment, lignin synthesis is measured by measuring expression and/or activity of lignin biosynthetic enzymes. Lignin biosynthetic enzymes include phenylalanine ammonia lyase (PAL), cinnamate 4-hydroxylase (C4H), 4-coumarate coenzyme A ligase (4CL), ferulate 5-hydroxylase (F5H), p-coumarate 3-hydroxylase (C3H), p-hydroxycinnamoyl-CoA:quinate/shikimate hydroxycinnamoyl transferase (HCT), caffeoyl-CoA O-methyltransferase (CCoAOMT), cinnamoyl-CoA reductase (CCR), caffeic acid O-methyltransferase (COMT), and cinnamyl alcohol dehydrogenase (CAD) (for review, see Wang, et al., *Frontiers Plant Sci. Vol.* 4, Art. 220, pages 1-14 (2013)).

Expression and/or activity of lignin biosynthetic enzymes can be determined by isolating enzymes or lignin content in from plants in vivo. Determinations of expression of lignin synthesis enzymes can also be made in vitro in plants, for example, using protoplast (isolated cell wall-free plant cells) assays. Protoplasts can be propagated from a desired plant using the methods of Guo J. et al., (*PLoS ONE* 7:e44908 (2012)). Briefly, protoplasts are isolated from the plant, and RNA is extracted and subjected to PCR analysis using primers specific for the gene or genes of interest. The expression of a normalization gene, such as a ubiquitin gene, can be used to standardize the expression of each gene. Expression of an enzyme can be compared between protoplasts transfected with an allelic variant of POPTR_0014s08530 and protoplasts not having the same allelic variant (e.g., protoplasts transfected with a different allelic variant, or without a POPTR_0014s08530 gene). In one example, the expression of three genes that encode enzymes of three major cell wall components, namely, PtrCesA8 for cellulose biosynthesis, PtrGT43B for hemicellulose biosynthesis and PtrCcoAOMT1 for lignin biosynthesis, can be used to determine expression of cell wall synthesis enzymes, which correlates with cell wall polymer composition in total.

Methods to Select Plants for Lignin Synthesis, Sugar Release, S/G Ratio, and Resistance to Environmental Stress and Pathogens In one embodiment, methods of selecting a plant for lignin synthesis, sugar release, S/G ratio, and resistance to stress/pathogen characteristics are provided. The methods include the steps of (a) obtaining nucleic acids from a candidate plant; (b) identifying an allelic variant of the POPTR_0014s08530 gene in the nucleic acids; and (c) selecting a plant based on the presence of an allelic variant of the POPTR_0014s08530 gene in the nucleic acids obtained from the plant.

The first step in selecting a plant for a lignin synthesis, sugar release, S/G ratio, or resistance to stress/pathogen characteristic is to obtain nucleic acids from a candidate plant. The candidate plant is a plant that may harbor an allelic variant of POPTR_0014s08530, or a plant that may have altered activity of POPTR_0014s08530 gene. Methods of obtaining nucleic acids from a candidate plant and detecting the presence of a nucleotide sequence are known in the art. Nucleic acid can be isolated from a plant tissue sample, according to standard methodologies (Sambrook et al., Molecular Cloning, 2nd ed., Cold Spring Harbor Laboratory Press, CSH, 1.38-1.39, 1989).

Detection of Nucleic Acid Sequences

Once nucleic acids are obtained, the next step in selecting a plant having altered lignin synthesis is to detect the presence of an allelic variant of POPTR_0014s08530 in the candidate plant. Detecting the presence of a target gene, such as an allelic variant of POPTR_0014s08530, can be accomplished by, for example, hybridization of probes to the target sequence (nucleic acid hybridization), or by amplification of target nucleic acid sequences, followed by detection of target sequences.

A number of template dependent processes are available to amplify the marker sequences present in a given nucleic acid sample. One of the best known amplification methods is the polymerase chain reaction (referred to as PCR). Other methods of amplification are ligase chain reaction (LCR), Qbeta Replicase, isothermal amplification, strand displacement amplification (SDA), PCR-like template- and enzyme-dependent synthesis using primers with a capture or detector moiety, transcription-based amplification systems (TAS), cyclical synthesis of single-stranded and double-stranded DNA, "RACE", one-sided PCR, and di-oligonucleotide amplification.

The PCR method is well known in the art and disclosed, for example, in WO 99/28500; Sambrook et al. (Molecular Cloning—A Laboratory Manual, Cold Spring Harbor Laboratory, Cold Spring Harbor, N.Y. 1989); Nucleic Acid Hybridization (Hames and Higgins eds., 1984); and Current Protocols in Human Genetics (Dracopoli et al., eds, 1984 with quarterly updates, John Wiley & Sons, Inc.), all of which are incorporated herein by reference. The PCR method utilizes a pair of oligonucleotide primers, each hybridizing to one strand of a double-stranded DNA/RNA target. The primers flank the region that will be amplified. The PCR method comprises contacting the primers and target sequence, or mixture of target sequences and optional polynucleotide probes, and performing the amplification steps.

Allelic variants can be detected by hybridization of nucleic acid probes to the target sequence. As used herein, a "probe" is an oligonucleotide that is capable of hybridizing to a target nucleic acid sequence, and which also has additional features (e.g., a fluorescent moiety, a dye, a bead, a particle, a nucleic acid sequence, etc) which allow for detection, immobilization, or manipulation of the target nucleic acid sequence. A "probe set" or "probeset" is a collection of two, three, or more probes designed to interrogate a given sequence. In contrast, a "primer" is an oligonucleotide that is capable of hybridizing to a target nucleic acid sequence and serves as a starting point for DNA synthesis/amplification. Primers may or may not contain additional features for detection, immobilization, or manipulation of the target nucleic acid sequence. For both probes and primers, the hybridizing portion is a stretch of preferably 10-50, more preferably 15-35, and most preferably 15-30 nucleotides. Suitable probes and primers (e.g., DNA probes and primers, RNA probes and primers) for hybridization to a target nucleic acid include, but are not limited to, probes and primers having at least about 70%, 75%, 80%, 85%, 90%, 95%, 98% or 99% complementarity to a target nucleic acid sequence, as well as probes and primers that have complete complementarity to a target nucleic acid sequence. Methods for preparation of labeled DNA and RNA probes and primers, and the conditions for hybridization thereof to target nucleic acid sequence, are described in Molecular Cloning: A Laboratory Manual, J. Sambrook et al., eds., 2nd edition (Cold Spring Harbor Laboratory Press, 1989), Chapters 10 and 11, the disclosures of which are incorporated herein by reference.

Primers for nucleic acid amplification of the POPTR_0014s08530 gene should contain a hybridizing region exactly or substantially complementary or corresponding to a target nucleotide sequence. Primer extension is performed under hybridization conditions of sufficient stringency to allow the selective amplification of the target sequence. A primer can either consist entirely of the hybridizing region or can contain additional features which allow for detection, immobilization, or manipulation of the amplified product, but which do not alter the basic property of the primer (that is, acting as a point of initiation of DNA synthesis).

Once an allelic variant of the POPTR_0014s08530 gene, is identified in a candidate plant, the plant is selected as a plant having particular lignin synthesis, sugar release, S/G ratio, or stress/pathogen resistance characteristic. Sugar release characteristics include high or low sugar release, such as high or low release of glucose and/or xylose. Preferred sugar release characteristics include high release of glucose and/or xylose. Lignin synthesis characteristics include high or low expression of at least one enzyme in the lignin synthesis pathway, and low lignin content. S/G ratio characteristics include increased or decreased S/G ratios. Stress resistance characteristics include increased resistance to dehydration/drought, lack of sunlight, lack of nutrients, poor soil conditions, and elevated temperatures. Pathogen resistance characteristics include increased resistance to one or more plant pathogens, particularly viral or bacterial plant pathogens.

In one example, the allelic variant encodes the polypeptide of SEQ ID NO: 2 or 4. In another example, the allelic variant is SEQ ID NO: 1 or 3. In a further example, the allelic variant can encode at least one amino acid alteration (substitution of one amino acid for another), addition, or deletion (removal of an amino acid) relative to the amino acid sequence of SEQ ID NO: 2. In a specific example, the allelic variant can encode an amino acid sequence that has an increased or decreased number of adjacent glutamines relative to the number of glutamines (13) at residues 24-36 of SEQ ID NO: 2. An example of an allelic variant with an increased number of glutamine repeats relative to the amino acid sequence of SEQ ID NO: 2 is SEQ ID NO: 4, which is encoded by the nucleic acid sequence of SEQ ID NO: 3.

Selection and Screening Using the POPTR_0014s08530 Gene

The sequence of an allelic variant of the POPTR_0014s08530 gene can be used as a molecular marker for use in screening germplasm in plant breeding programs. Primers targeting conserved regions of the gene can be used to identify genotypes carrying alterations that lead to amino acid substitutions which can affect gene function. A population of plants can be screened or selected for those members of the population that have a desired trait or phenotype. Selection or screening can be carried out over one or more generations, which can be useful to identify those plants that have a desired characteristic, such as low recalcitrance, low lignin synthesis, high S/G ratio, and/or increased stress or pathogen resistance. Selection or screening can be carried out in more than one geographic location. In some cases, transgenic plants can be grown and selected under conditions which induce a desired phenotype or are otherwise necessary to produce a desired phenotype in a transgenic plant. In addition, selection or screening can be carried out during a particular developmental stage in which the phenotype is exhibited by the plant.

A related embodiment provides methods to detect the presence of an allelic variant of POPTR_0014s08530 in a plant. The method involves selecting a plant having high or low sugar release, such as high or low glucose or xylose release, and determining the sequence of the gene at the POPTR_0014s08530 locus in said plant.

Inhibitors and Expression Vectors for Modulating the Activity of POPTR_0014 s08530

Further disclosed herein are nucleic acid inhibitors of expression of POPTR_0014s08530, or inhibitors of expression of allelic variants of POPTR_0014s08530 including SEQ ID NO: 1, which can be used to reduce expression of the POPTR_0014s08530 gene and allelic variants thereof, to provide low lignin biosynthesis, high sugar release, and/or increased resistance to stress or pathogens. Specific nucleic acid inhibitors include antisense RNA, small interfering RNA, RNAi, microRNA, artificial microRNA, and ribozymes. Inhibitors of POPTR_0014s08530 activity include expression vectors encoding a POPTR_0014s08530 allelic variant with an increased number of glutamine repeats relative to the number of glutamine repeats in the sequence of SEQ ID NO: 2, operably linked to a regulatory region that is functional in a plant.

The polynucleotides and expression vectors described herein can be used to increase or inhibit expression of POPTR_0014s08530 or a POPTR_0014s08530 allelic variant. The term "expression" refers to the process of converting genetic information of a polynucleotide into RNA through transcription, which is catalyzed by an enzyme, RNA polymerase and into protein, through translation of mRNA on ribosomes. Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

A "nucleic acid inhibitor" is a nucleic acid that can reduce or prevent expression or activity of a target gene. For example, an inhibitor of expression of POPTR_0014s08530 can reduce or eliminate transcription and/or translation of the POPTR_0014s08530 gene product, thus reducing POPTR_0014s08530 protein expression.

An altered level of gene expression refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204, 253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep.* V19:304-310 (2000); Chang and Yang, *Bot. Bull. Acad. Sin.*, V37:35-40 (1996) and Han et al., *Biotechnology in Agriculture and Forestry*, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit POPTR_0014s08530 expression in plants. Suitable inhibitors include full-length nucleic acids of allelic variants of POPTR_0014s08530, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophile*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., Plant Physiol., 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators of POPTR_0014s08530 and Uses Thereof.

This disclosure provides methods of altering lignin synthesis and sugar release in a plant, comprising introducing into a plant cell an exogenous nucleic acid with a regulatory region operably linked to a nucleic acid encoding a POPTR_0014s08530 allelic variant, where a tissue of a plant produced from the plant cell has an altered cell wall compared to the cell wall in tissue of a control plant that does not comprise the nucleic acid.

In one embodiment, the exogenous nucleic acid is an expression vector encoding the polypeptide of a POPTR_0014s08530 allelic variant that leads to low, inhibited or decreased lignin synthesis. Preferred POPTR_0014s08530 allelic variants include variants with an increased number of glutamine repeats relative to the number of glutamine repeats in SEQ ID NO: 2. An example of such an expression vector is an expression vector comprising the POPTR_0014s08530 allelic variant encoding SEQ ID NO: 4. Expression of such a vector in a plant or plant cell would lead to a decrease in lignin synthesis in that plant or plant cell. This expression vector would be useful, for example, for increasing sugar release, that is, increasing glucose and/or xylose release, in a plant or plant cell in which the expression vector is introduced, relative to plants or plant cells which are not transformed by the vector. This expression vector would also be useful for decreasing lignification or lignin production in a plant or plant cell in which the expression vector is introduced.

In a further embodiment, such an expression vector encoding a POPTR_0014s08530 allelic variant with an increased number of glutamine repeats relative to the number of glutamine repeats in SEQ ID NO: 2 leads to plants with increased resistance to environmental stress and/or pathogens. An example of such an expression vector is an expression vector comprising the POPTR_0014s08530 allelic variant encoding SEQ ID NO: 4. This expression vector would be useful, for example, for increasing resistance of plants to environmental stress or pathogens, in a plant or plant cell in which the expression vector is introduced, relative to plants or plant cells which are not transformed by the vector.

In another embodiment, the exogenous nucleic acid is an expression vector encoding the polypeptide of a POPTR_0014s08530 allelic variant that leads to high or increased lignin synthesis. An example of such an expression vector is an expression vector comprising the POPTR_0014s08530 allelic variant encoding SEQ ID NO: 2. This expression vector would be useful, for example, for increasing lignin synthesis in a plant or plant cell in which the expression vector is introduced, relative to plants or plant cells which are not transformed by the vector.

Vectors containing nucleic acids such as those described herein are provided. A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorsulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate: CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)) and the rice tungro bacilliform virus (RTBV) promoter (Dai et al., *Proc. Natl. Acad. Sci. USA*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one example, the coding sequence of a POPTR_0014s08530 allelic variant is amplified from either genomic DNA or cDNA by PCR. The DNA fragments are then subcloned into an expression construct. In this example, a construct is made by first digesting pSAT4A-DEST-n(1-174)EYFP-N1 (ABRC stock #CD3-1080) and pSAT5-DEST-c(175-end)EYFP-C1(B) (ABRC stock #CD3-1097) (Citovsky V. et al., *J Mol Biol* 362:1120-1131 (2006)) with NdeI and BglII, then ligating the 1.1 kb fragment of the first construct and 4.4 kb fragment of the second one, followed by subcloning of the coding sequence of a POPTR_0014s08530 allelic variant into the construct to create the expression vector.

Transgenic Plants/Plant Species/Plant Cells

Also disclosed herein are plants and plant cells genetically modified by introduction of the disclosed inhibitors and expression vectors. In certain cases, a transgenic plant cell or plant comprises at least two recombinant nucleic acid constructs or exogenous nucleic acids, e.g., one including a nucleic acid encoding a POPTR_0014s08530 allelic variant or homolog, and another including a nucleic acid encoding a second POPTR_0014s08530 allelic variant or one or more different cell wall modulating polypeptides.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous POPTR_0014s08530 allelic variant whose expression has not previously been confirmed in particular recipient cells.

Initial and immediate application of the expression of POPTR_0014s08530 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, *sorghum*, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium;* and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia;* and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula,* alba and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In one aspect, a plant cell is provided. The plant cell comprises an endogenous or exogenous nucleic acid comprising a regulatory region operably linked to a polynucleotide encoding a POPTR_0014s08530 allelic variant where a tissue of a plant produced from the plant cell has an altered cell wall compared to the cell wall in tissue of a control plant that does not comprise the nucleic acid.

The cell can further comprise a nucleic acid encoding a second POPTR_0014s08530 allelic variant operably linked to a second regulatory region. The nucleic acid encoding a second POPTR_0014s08530 allelic variant operably linked to a second regulatory region can be present on a second recombinant nucleic acid construct. This allows expression of the POPTR_0014s08530 allelic variant in multiple combinations, such as under control of different promoters or multiple copies of the gene.

In another aspect, a plant cell comprising a POPTR_0014s08530 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of POPTR_0014s08530 or a POPTR_0014s08530 allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered (increased or decreased) lignin synthesis.

Methods of Use of Transgenic Plants

Disclosed herein are methods to increase glucose and/or xylose release in a plant or plant cell, or to decrease lignin synthesis, or to alter S:G ratio, by expressing the disclosed inhibitors, or expressing expression vectors encoding a POPTR_0014s08530 allelic variant that leads to reduced lignin synthesis (for example, an expression vector encoding SEQ ID NO: 4), in plants and plant cells.

Further disclosed herein are improved methods of producing biofuel from cellulosic biomass, by using plants with reduced or inhibited expression or activity of the POPTR_0014s08530 gene in biofuel production processes. Methods of pretreatment and saccharification of biomass to fermentable sugars, followed by fermentation of the sugars to ethanol, are known in the art.

Additionally disclosed are methods for increasing lignin synthesis in a plant or plant cell, by expressing expression vectors encoding a POPTR_0014s08530 allelic variant that leads to increased lignin synthesis (for example, an expression vector encoding SEQ ID NO: 2), in a plant or plant cell of interest. Additionally disclosed are methods of producing paper and pulp, by using plants with increased expression of the POPTR_0014s08530 gene in paper or pulp production processes, as known in the art.

Articles of Manufacture

The materials and methods described herein are useful for modifying biomass characteristics, such as characteristics of biomass renewable energy source plants. "Biomass" refers to any cellulosic or lignocellulosic raw material and includes materials containing cellulose, and optionally further containing hemicellulose, lignin, starch, oligosaccharides and/or monosaccharides. The term "cellulosic" refers to a composition containing cellulose. The term "lignocellulosic" refers to a composition containing both lignin and cellulose. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, *sorghum*, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

The invention also relates to the use of the pulp obtained from the disclosed genetically modified plants in the production of cellulose-based products, for example, in the paper industry, or for the production of cardboard. Pulp, produced using plants which have been genetically modified to have increased expression of the POPTR_0014s08530 gene and therefore also have increased lignin synthesis, can be used as a building material and in particular as output material for pressed chipboard, fiberboard of medium density, or as filler material.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide increased amounts of lignin or altered S/G lignin ratio in one or more tissues of plants grown from such seeds.

The present disclosure is further illustrated by the following non-limiting examples.

EXAMPLES

Materials and Methods

Association Mapping Populations.

A population of 1,100 naturally varying black cottonwood genotypes (*P. trichocarpa*) was assembled to encompass the central portion of the natural range of *P. trichocarpa*, stretching from 38.8° to 54.3° from California to British Colombia (Slavov G T. et al., *New Phytologist* 196(3):713-25 (2012)). Propagation materials were collected from individual trees, clonally replicated under nursery conditions at Mount Jefferson Farms, Salem, Oreg. and subsequently established in replicated field plots in Placerville, Calif. (38° 43'47"N 120° 47'55"W), Corvallis, Oreg. (44° 34'14.81"N 123° 16'33.59"W) and Clatskanie, Oreg. (46° 6'11"N 123° 12'13"W). Additional details regarding field management and environmental conditions are given in supplementary materials. A partially overlapping and independently phenotyped population of 499 *P. trichocarpa* genotypes was collected from a latitudinal range spanning from 44° to 58.6° and established in Surrey, British Colombia as described by Porth I. et al., *New Phytologist* 197:777-790 (2013). After eliminating genotypes with evidence of sibship (Porth et al., *New Phytologist* 200: 710-726 (2013) and missing SNP data >10%, the two populations shared 146 genotypes during the phenotypic correlation analysis and 123 genotypes during the association mapping analysis.

QTL Mapping Pedigree.

A pseudo-backcross population with 712 individuals was established in a replicated field trial in Morgantown, W. Va. (39° 38'1"N 79° 57'2"W). The population was developed by crossing a female *P. trichocarpa* clone, '93-968', from western Washington state with a male *P. deltoides* clone, 'ILL-101', from southern Illinois. The female $F_1$ genotype, '52-225', was crossed with an alternate male *P. deltoides* clone from Minnesota, 'D124', to create the 52-124 pseudo-backcross population.

Phenotyping.

Wood disks cut from each stem 1.2 m off the ground for each genotype in the pseudo-backcross mapping pedigree were collected in December Year#1 and February Year #3 from 2- and 3-year-old trees, respectively. In Year #1, 4.3 mm increment cores were collected from 570 of the 1,100 wild *P. trichocarpa* genotypes in their native environments. 300 single-replicate stem disks were harvested from 2-year-old trees in Corvallis, Oreg., and in June Year #3, 4.3 mm increment cores were collected from 932 4-year-old trees in Clatskanie, Oreg. Of the 932 genotypes, 235 had 2 biological replicates. Debarked and air-dried increment cores and stem disks were ground using a Wiley Mini-Mill (Swedesboro, N.J.) with a 20-mesh screen. Lignin content, syringyl to guaiacyl ratio (S/G) and 5- and 6-carbon sugar content were determined using pyrolysis Molecular Beam Mass Spectrometry (pyMBMS) analysis. Both assays were conducted at the National Renewable Energy Laboratory (Golden, Colo.) (see below for further details). Glucose and xylose release were evaluated using saccharification analysis described below. The Surrey population was characterized for seventeen different cell wall traits using wet chemistry assays at the University of British Colombia, Vancouver, BC, Canada as described by Porth I. et al., *New Phytologist* 197:777-790 (2013).

To complement this, wood cores from segregating pseudo-backcross ($BC_1$) mapping pedigree, Family '52-124', were collected in Year #1 and Year #2 from 2- and 3-year-old trees from a plantation in Morgantown, W. Va. Wood cores were subjected to the MBMS and saccharification assays as described below.

Saccharification Analysis of the *P. trichocarpa* Population.

Wood samples were treated with α-amylase (spirizyme Ultra—0.25%, Novozymes, North America, Inc., Franklinton, N.C.) and β-glucosidase (Liquozyme SC DS—1.5%, Novozymes) in 0.1 M sodium acetate (24 h, 55° C., pH 5.0) to remove available starch (16 ml enzyme solution per 1 g biomass). This was followed by an ethanol (95% v/v) soxhlet extraction for an additional 24 h to remove extractives. After drying overnight, 5 mg (±0.5 mg) of extract-free biomass was weighed in triplicate into a solid hastelloy 96 well microtiter plate. 250 µl $H_2O$ were added, the samples were sealed with silicone adhesive and Teflon tape and heated at 180° C. for 40 min. Once cooled, 40 µl of buffer-enzyme stock was added. The buffer-enzyme stock consisted of 8% CTec2 (Novozymes) in 1 M sodium citrate buffer. The samples were then gently mixed and left to statically incubate at 50° C. for 70 h. After the 70 h incubation, an aliquot of the saccharified hydrolysate was diluted and tested using the glucose oxidase/peroxidase and xylose dehydrogenase assays (Megazyme International Ireland, Wicklow, Ireland). Results were calculated using calibration curves constructed from standard mixtures of glucose and xylose.

Pyrolysis MBMS.

A commercially available MBMS (molecular beam mass spectrometry) designed specifically for biomass analysis was used for pyrolysis vapor analysis (Evans R J. et al., *Energy and Fuels* 1:123-137 (1987); Sykes R. et al., *Biofuels: Methods and Protocols* 169-183 (2009); Tuskan G. et al., *Appl. Biochem. Biotechnol.* 77:55-65 (1999)). Approximately 4 mg of air dried 20 mesh biomass was introduced into the quartz pyrolysis reactor via 80 µL deactivated stainless steel Eco-Cups provided with the autosampler. Mass spectral data from 30-450 m/z were acquired on a Merlin Automation Data System version 3.0 (Extrel CMS, Pittsburgh, Pa.) using 17 eV electron impact ionization.

Lignin estimates were determined by summing the intensities of peaks assigned to lignin compounds. The lignin intensities were then corrected to a standard with a known Klason lignin content using a single point correction technique. S/G ratios were determined by summing the syringyl peaks 154, 167, 168, 182, 194, 208 and 210 and dividing by the sum of guaiacyl peaks 124, 137, 138, 150, 164 and 178.

SNP Genotyping in Pseudo-Backcross Pedigree and Genetic Map Construction.

712 pseudo-backcross progeny were genotyped using a 5K Illumina Infinium SNP array (Illumina, San Diego, Calif.) containing 5,390 probes. Details of array design, target SNP selection and DNA preparation are given in supplementary materials. SNP clusters were visualized using the Illumina GenomeStudio software V2010.3 (Illumina, Calif.) and were manually curated for cluster separation before extracting genotype calls. SNPs with the expected segregation pattern, a minimum GenTrain score of 0.15 and non-overlapping clusters were considered for downstream analysis. Map construction was conducted using JoinMap 4.0 (Van Ooijen J W, MAPQTL (Kyazma B V, Wageningen, Netherlands) (2009)) using SNPs with less than 5% missing data and a minor allele frequency (MAF) of at least 0.30 after excluding genotypes with more than 10% missing data. Linkage groups (LG) were numbered according to markers derived from the 19 chromosome-scale scaffolds assembly (Tuskan, G A, et al., *Science*, 313:1596-1604 (2006)).

Genotyping of the *P. trichocarpa* Population and Association Mapping.

The 34K Illumina INFINIUM® SNP array described by Geraldes A. et al., *Molecular Ecology Resources* 13:306-323 (2013) was used to genotype 991 and 334 individuals of the 1,100 and Surrey populations, respectively. The array was designed to encompass SNPs distributed in and around 3,543 candidate genes and was based on v2.2 of the *Populus* reference genome (available on the phytozome website). SNP data were visualized and curated as described above.

SNP positions for the 5K and 34K Infinium arrays were translated into v3.0 positions by aligning sequences flanking the SNP against the phytozome poplar v3.0 assembly. SNP names included the scaffold number followed by the physical position of the SNP.

Since the Infinium SNP array was not designed to achieve marker saturation, a second genotyping exercise was conducted using whole-genome re-sequencing to exhaustively characterize SNP and indel polymorphisms. Briefly, 673 genotypes representing the central latitudinal range of the 1,100 population were sequenced using the Illumina Genome Analyzer (Illumina, Calif.) at the Joint Genome Institute (Walnut Creek, Calif.). Short reads were aligned to v3.0 of *Populus* genome assembly using BWA 0.5.9-r16 with default options (Li, H, et al., *Bioinformatics* 25:1754-1760 (2009)). SNP and indel polymorphisms were called using SAMtools mpileup and bcftools (Li, H, et al., *Bioinformatics,* 25:2078-2079 (2009)). Only genotypes with more than 90% agreement between the two platforms were used in downstream analysis. SNPs were named as described above.

Population Structure and Kinship.

Q estimates of population structure were computed based on a set of 1507 SNPs with no missing data and MAF>0.05 distributed across the 19 scaffolds of the genome assembly. The admixture model with correlated allele frequencies was run in the software Structure 2.3.3 with 10,000 burn-ins and 10,000 MCMC replications after burn-in for K=1 to 15. The K estimate with the highest mean ln P(D) values was accepted as the number of distinct sub-populations. A pairwise kinship matrix was generated based on 27,940 SNPs with less than 10% missing data and MAF>0.05 using TASSEL 3.0 software (available online on the sourceforge website).

Linkage Disequilibrium.

The inventors evaluated the extent of LD on a chromosome-wide scale using SNP data from the Infinium SNP array and on a locus-specific scale using SNP data from whole-genome re-sequencing effort. The LDheatmap function was implemented in R to calculate pairwise LD for all SNPs (Shin, J H, et al., *J Statistical Software* 16:Code Snippet 3 (2006)).

QTL Mapping.

The maximum likelihood algorithm of the Multiple-QTL Mapping (MQM) package of MapQTL 6.0 (Van Ooijen J W, MAPQTL (Kyazma B V, Wageningen, Netherlands) (2009)) was used to identify QTLs. One thousand permutations were conducted separately for each trait and experiment to determine genome-wise LOD significance threshold at p<0.05 (Churchill, G A, et al., *Genetics,* 138:963-971 (1994)). QTLs were declared significant when identified (i.e., having LOD scores above the significance threshold) in at least two independent experiments or between two different phenotypes in the same experiment. A drop in LOD score of 1.0 was used to declare separate adjacent QTL.

Association Mapping.

Based on evidence of a major QTL hotspot for cell wall phenotypes, SNPs distributed across chromosome XIV of the assembly were specifically evaluated for association with recalcitrance phenotypes. SNPs with a MAF>0.05 from the Infinium array and re-sequencing data were used in this part of the study. Firstly, SNP-trait associations were evaluated for the Infinium array data on a whole-chromosome scale as well as on a QTL-interval scale. Based on results of this analysis, we performed a second analysis using re-sequencing data to saturate candidate loci revealed during the first analysis. The software TASSEL 3.0 (available online on the sourceforge website) was used to identify marker-trait associations using the mixed linear model analysis with kinship and population structure as covariates (Yu, J, et al., *Nat Genet,* 38:203-208 (2005)). Cell wall chemistry phenotypes, as well as individual m/z peak intensities from the pyMBMS analysis, were analyzed.

Candidate gene intervals identified based on the Infinium array data were saturated with SNPs from the re-sequencing effort and re-analyzed for associations using phenotypic data from Corvallis, Clatskanie and native environments. Candidate intervals were saturated by selecting SNPs within each candidate gene plus 10 kb flanking regions.

Statistical Analysis.

Correction for multiple testing was conducted using the unadjusted Bonferroni correction (Bonferroni C E., *Il calcolo delle assicurazioni su gruppi di teste chapter "Studi in Onore del Professore Salvatore ortu Carboni"*, 13-60 (1935)) on a chromosome-wise level using all SNP markers and on QTL-interval-wise level using SNPs falling within QTL and candidate gene intervals. Spearman's rank correlation analyses were performed using the Statistix 8 software (Statistix 8 user's manual: Analytical Software, Tallahassee Fla. (2003)).

cDNA Cloning and *Populus* Protoplast Transient Expression Assay.

For vector construction, a Gateway compatible construct for transient gene expression in protoplasts was made by first digesting pSAT4A-DEST-n(1-174)EYFP-N1 (ABRC stock #CD3-1080) and pSAT5-DEST-c(175-end)EYFP-C1 (B) (ABRC stock #CD3-1097) (Citovsky et al., 2006) with NdeI and BglII, then ligating the 1.1 kb fragment of the first construct and 4.4 kb fragment of the second one. The efficacy of this construct was validated by over-expressing a GUS gene in protoplasts. The coding sequence of each *Populus* gene was cloned from cDNA by PCR. The DNA fragments were introduced into a pENTR vector by using pENTR™/D-TOPO® Cloning Kit (Invitrogen Inc., Carlsbad, Calif.). The gene of interest was then subcloned into the above-mentioned expression construct using LR Clonase (Invitrogen Inc., Carlsbad, Calif.).

Regulatory genes including transcription factors and protein kinases, whose activity could be measured relative to activation of marker genes were selected for cloning and protoplast assays. Greenhouse-grown genotypes from the 1,100 *P. trichocarpa* association population carrying alternate alleles of target genes were used to clone cDNAs for the protoplast assay. The AN locus was cloned using the following primers:

```
        Potri.014G089400_F (forward primer):
                                   (SEQ ID NO: 29)
        CACCATGAGCGCCACGACTACC;

Potri.014G089400_R (reverse primer):
                                   (SEQ ID NO: 30)
        CTAATCTAGCCAACGAGTAACACC.
```

Sequence verification was done by sequencing each cDNA from both directions. Sequence translation was done using the ExPASy online translate tool (available on the expasy website) and cDNA and protein alignments were generated using the online EMBL-EBI ClustalW2 tool (available online through the clustalw2 Tools link on the ebi.ac.uk website).

Alternate alleles as well as a negative control, an empty vector, were transfected into *Populus* protoplasts and evaluated for the induction of marker genes for cellulose, hemicelluloses and lignin biosynthetic pathways described below. The *Populus* protoplast transfection assay was conducted as described by Guo J. et al., *PLoS ONE* 7:e44908 (2012). Briefly, intact protoplasts were isolated from leaves of the *Populus* genotype 717 cultured on MS medium in a Magenta box. Protoplasts from the same isolation were separated into three pools for side-by-side transfection with the two alternate alleles and the negative control. Each transfection treatment was replicated three times. Transfected protoplasts were incubated overnight under low light condition (10 µmol s$^{-1}$ m$^2$) to facilitate the expression of the transgene. Total RNA was extracted from approximately 5 million protoplasts with Trizol (Invitrogen Inc., Carlsbad, Calif.). Two-hundred-fifty microliters of Trizol was used for each RNA extraction and linear polyacrylamide (Gaillard, C, et al., *Nucleic Acids Research*, 18:378-378 (1990)) was added in the RNA precipitation step as a carrier. 500 ng of total RNA was used for reverse transcription using RevertAid™ Reverse Transcriptase (Fermentas Inc. Hanover, Md., USA) and oligo dT$_{16}$ as the primer. The real-time PCR primers were designed using the NCBI Primer-BLAST tool (Ye, J, et al., *BMC Bioinformatics* 13:134 (2012)) Primers used for qPCR:

```
                                   (SEQ ID NO: 31)
        PtrUBQqF-5'ACTCCACTTGGTGCTCCGTTTGAGG, (SEQ ID NO: 32)
        PtrUBQqR-5'AGTCTCTGCTGGTCTGGTGGGATACCCT, (SEQ ID NO: 33)
        PtrCcoAOMT1qF-5'ACGTCAGCGATGCCTCAGGG, (SEQ ID NO: 34)
        PtrCcoAOMT1qR-5' GCTACCAACCGGGAGGGGGT, (SEQ ID NO: 35)
        PtrCESA8qF-5'GGGTCGCCAAAACCGAACACCA, (SEQ ID NO: 36)
        PtrCESA8qR-5' TCCAATTTCCGAAGGTTTAGCCCCA, (SEQ ID NO: 37)
        PtrGT43BqF-5' GTCGCCCTTCTTCAGTCCAGCA, (SEQ ID NO: 38)
        PtrGT43BqR-5' ACAGTCCTCTGGTGGGATTCCCT.
```

The specificity of each primer pair was determined by aligning the primers against the reference RNA sequence database for *P. trichocarpa* using the Blastn program (available online at the National Center for Biotechnology Information website). Real-time PCR reactions were conducted on a StepOne Plus™ Realtime PCR system (Applied Biosystems) with the iTaq™-SYBRH Green Super Mix with ROX (Bio-RAD Inc.). Expression of the *Populus* ubiquitin gene, Potri.001G418500, was used to standardize the expression of each gene. A 35S::GFP (*Arabidopsis* Biological Resource Center stock #: CD3-911) construct was co-transfected for each sample to monitor the transfection efficiency in each assay. Only assays with estimated transfection efficiency of 60% or higher were used for qRT-PCR analysis.

The expression of three marker genes associated with cell biosynthesis pathways, namely, PtrCesA8 (Potri.011G069600) for cellulose, PtrGT43B (Potri.016G086400) for hemicellulose and PtrCcoAOMT1 (Potri.009G099800) for lignin biosynthesis (Zhong, R, et al., *Plant Physiol* 152:1044-1055 (2010)), were used to assess difference in activation potential among allelic variants and the negative control. Two transcriptional factors, PtrWND2B (Zhong, R, et al., *Plant Signal Behav* 5:469-72 (2010)) and PtrMYB20 (Zhong, R, et al., *Plant Physiol* 157:1452-68 (2011)), known to regulate the expression of the three marker genes were used to validate this system. In order to construct the promoter::GUS reporter, the 2 kb sequence upstream of the CDSs of the three reporter genes was cloned and fused to a GUS gene by replacing the UBQ10 promoter of the HBT95-pUBQ10-GUS construct reported previously (Norris, S R, et al., *Plant Molecular Biology* 21:895-906 (1993)).

Results pyMBMS Analysis of the *P. trichocarpa×P. Deltoides* Pseudo-Backcross Population.

Lignin content within the pseudo-backcross ranged from 21.8 to 32.7 among the 2- and 4-year old trees. S/G ratios for the same material ranged from 1.5 to 2.5 in each of the two sampling datasets. 5- and 6-carbon sugars were only evaluated in the Year #1 sampling and phenotypic values ranged from lows of 23.7 and 24.8 and highs of 34.4 and 36.7, respectively.

Phenotypic values for each trait were highly correlated between Year #1 and Year #3 samples. Correlations between different phenotypes were also largely significance within and between years. For example, lignin and S/G ratio were significantly correlated in both years, Year #1 (r=0.37, p<0.00001) and Year #3 (r=0.36, p<0.00001) and 5- and 6-carbon sugars were negatively correlated with lignin, r=−0.65 (p=0.0000) and r=−0.77 (p=0.0000), respectively.

pyMBMS Analysis of the *P. trichocarpa* Population.

The lowest lignin content between the Native, Corvallis, and Clatskanie environments were 15.7, 20.6, and 17.7% lignin from total biomass and the highest percent lignin were 27.9, 28, and 28.1% lignin from total biomass, respectively. S/G ratios ranged from 1 to 3 in the native environment, between 1.5 and 2.4 in Corvallis, and between 1.3 and 2.5 in Clastkanie. 5 and 6-carbon sugars in the native environment ranged from 18.1 to 29.9, and 21.8 to 43.2, respectively. In Corvallis, the same phenotypes ranged from 19.5 to 31.7 and 20.3 to 38.3, respectively.

Phenotypic correlations were generally higher within the same environment and moderate to not significant across different environments. S/G ratio exhibited the highest correlation across different environments, achieving a high of r=0.43, p<0.00001 (n=258) between the Corvallis and Clatskanie common gardens and r=0.31, p<0.00001 (n=795) between the Clatskanie and native environments. Similarly, S/G ratio had the highest correlation between different phenotyping platforms, reaching r=0.61, p<0.00001 (n=146) between the pyMBMS-characterized native and the wet chemistry-characterized Surrey environments.

Saccharification Analysis of the *P. trichocarpa* Population.

Glucose release ranged from 0.01 to 0.48 mg/mg biomass in the native environments, 0.01 to 0.21 in Corvallis and 0.17 to 0.50 in Clatskanie. Xylose release for the same environments ranged from 0.07 to 0.19 mg/mg biomass, 0.01 to 0.19 and 0.09 to 0.24 mg/mg biomass, respectively. Glucose release was negatively correlated with lignin content in both native and Clatskanie environments as well as between the native environments and the Surrey populations that were phenotyped using different platforms.

SNP Genotyping in Pseudo-Backcross Pedigree and Genetic Map Construction.

The inventors incorporated 3,568 of the 3,751 segregating SNP markers into 19 linkage groups corresponding to the haploid number of *Populus* chromosomes. The map was 3,053.9 cM in length, with the largest linkage group being 379.2 cM for LG I and the shortest being 98.7 cM for LG XIX. The number of markers in a single linkage group ranged from 93 for LG XII to 458 for LG I. The average marker distance was 0.75 cM and the map covered 90% of the *P. trichocarpa* reference genome. The target LG XIV had 180 SNP markers with an average marker distance of 0.82 cM.

SNP Genotyping in *P. trichocarpa* Populations.

Performance results for the 34K Illumina INFINIUM SNP array were described in detail by Geraldes A. et al., *Molecular Ecology Resources* 13:306-323 (2013), whereas results for the Surrey population were described by Porth et al., *New Phytologist* 197:777-790 (2013) and Porth et al., *New Phytologist* 200: 710-726 (2013). For the 1100 population, 27,940 SNPs had less than 10% missing data, with MAF across all loci ranging from 0.044 to 0.500. On the target chromosome XIV, 1439 SNPs met the minimum criteria for use in association mapping having the less than 10% missing data and MAF>0.05.

Population Structure.

After excluding genotypes exhibiting evidence of clonality and high levels of relatedness, the inventors analyzed a set of 886 genotypes in the population structure analysis. There was a substantial increase in probability ln P(D) as a function of number of sub-populations from K=1 up K=6. The smallest differences among ln P(D) values were observed from K=7 up to K=10 after which the values exhibited substantial decrease between K=11 and K=15. The inventors selected K=10, which had the highest ln P(D), as the number of sub-populations in the Q matrix generated as a covariate in association analysis.

QTL Mapping.

Out of the 712 genotypes from the pseudo-backcross population, 515 individuals had both phenotypic and genotypic data for use in QTL mapping. A QTL hotspot for lignin content, S/G ratio, and 5- and 6-carbon sugars was identified on linkage group XIV corresponding to scaffold 14 of the *Populus* genome. All QTLs exceeded the genome-wise LOD significance thresholds in each experiment with percentage phenotypic variance explained (% PVE) ranging from 1.9 to 7.5%. QTL profiles across this linkage group were reproducible between phenotypic data collected in two different years on 2- and 3-year-old progeny for the pseudo-backcross population. Using a drop in LOD score of 1 between peaks to distinguish neighboring QTL, the inventors identified QTLs for S/G ratio and lignin content and for 5- and 6-carbon sugars (Table 1). The SNP marker for scaffold 14_6368158, within QTL intervals 5872672-6437075 and 5673304-6437075, corresponds to the Potri.014G089400 locus.

TABLE 1

QTL intervals identified based on Multiple QTL Model (MQM) mapping in an interspecific pseudo-backcross population

| Trait | QTL physical interval | SNP marker at peak | LOD score | LOD significance threshold | % PVE |
|---|---|---|---|---|---|
| S/G ratio_Year 1 | 2560710-3122244 | Scaffold_14_2862785 | 5.72 | 2.0 | 5.0 |
| S/G ratio_Year 1 | 5872672-6437075 | Scaffold_14_6368158 | 8.14 | 2.0 | 7.0 |
| S/G ratio_Year 1 | 6528633-7579341 | Scaffold_14_6858404 | 8.73 | 2.0 | 7.5 |

TABLE 1-continued

QTL intervals identified based on Multiple QTL Model (MQM)
mapping in an interspecific pseudo-backcross population

| Trait | QTL physical interval | SNP marker at peak | LOD score | LOD significance threshold | % PVE |
|---|---|---|---|---|---|
| S/G ratio_Year 1 | 9117895-9944333 | Scaffold_14_9351168 | 4.91 | 2.0 | 4.3 |
| S/G ratio_Year 1 | 10002110-10563345 | Scaffold_14_10224867 | 4.12 | 2.0 | 3.6 |
| S/G ratio_Year 3 | 2560710-3511349 | Scaffold_14_2862785 | 5.92 | 2.0 | 5.2 |
| S/G ratio_Year 3 | 5673304-6437075 | Scaffold_14_6368158 | 8.58 | 2.0 | 7.4 |
| S/G ratio_Year 3 | 6475757-7579341 | Scaffold_14_6858404 | 8.32 | 2.0 | 7.2 |
| S/G ratio_Year 3 | 9095216-994433 | Scaffold_14_9386399 | 4.84 | 2.0 | 4.3 |
| S/G ratio_Year 3 | 9982303-10659100 | Scaffold_14_10224867 | 4.03 | 2.0 | 3.6 |

SNPs co-locating with QTL peaks were highly consistent between different experiments with a few exceptions. QTL peaks for all four traits tended to occur in the same general physical intervals. However, lignin content and 5- and 6-carbon sugars had the most robust co-location of QTL peaks on three intervals. In each case the same SNP markers had the highest LOD score for each phenotype in each experiment.

Association Mapping.

From the Infinium array-based association mapping effort, seven SNPs were identified within six candidate genes that exceeded the chromosome-wide 3.47E-05 (P<0.05) Bonferroni-adjusted significance threshold. Altogether, twelve SNPs from six candidate genes were ranked 1$^{st}$ in 14 unique marker-trait associations across the four sampling environments. Re-analysis of candidate gene intervals saturated using whole-genome re-sequencing data identified 21 SNPs from 5 of the 6 intervals with significant trait associations. Since only 673 genotypes had whole genome re-sequencing data compared to 991 for the infinium array, the reanalysis effort involved smaller population sizes across the three environments. Despite this difference in population sizes, there was close agreement between results based on the two genotyping platforms. SNPs with the lowest p-values mapped within 10.0 kb or less across multiple environments for 5 of the 6 intervals. For the remaining interval which encompassed a 17.9 kb candidate gene, SNPs mapped within 1.5 kb across three environments for the Infinium array and 30.7 kb across two environments for re-sequencing-based associations. All SNPs with significant associations mapped within QTL intervals for S/G ratio, lignin content, and 5- and 6-carbon sugars described above.

lyzing the same interval using 401 SNPs from the re-sequencing effort. However, three SNPs spanning a 2.7 kb region had suggestive associations with glucose/xylose release (p=6.84E-04) and 5-carbon sugars (p=4.63E-04) in the native environments and 6-carbon sugars (p=5.36E-04) in Corvallis.

Sequencing of Allelic Variants.

The inventors observed a tri-nucleotide repeat polymorphism with an additional CAGCAG starting at position 96 from the start codon in one of the alleles and a SNP (A/G) which resulted in a threonine/alanine amino acid substitution at positions 650 and 648 of the two proteins (FIGS. 1A and 1B). These polymorphisms resulted in two additional glutamine residues in the mature protein. As such, the allele derived from genotype BESC-470 had a longer PolyQ sequence compared to the allele derived from BESC-293.

Protoplast Assays.

Figure 3:
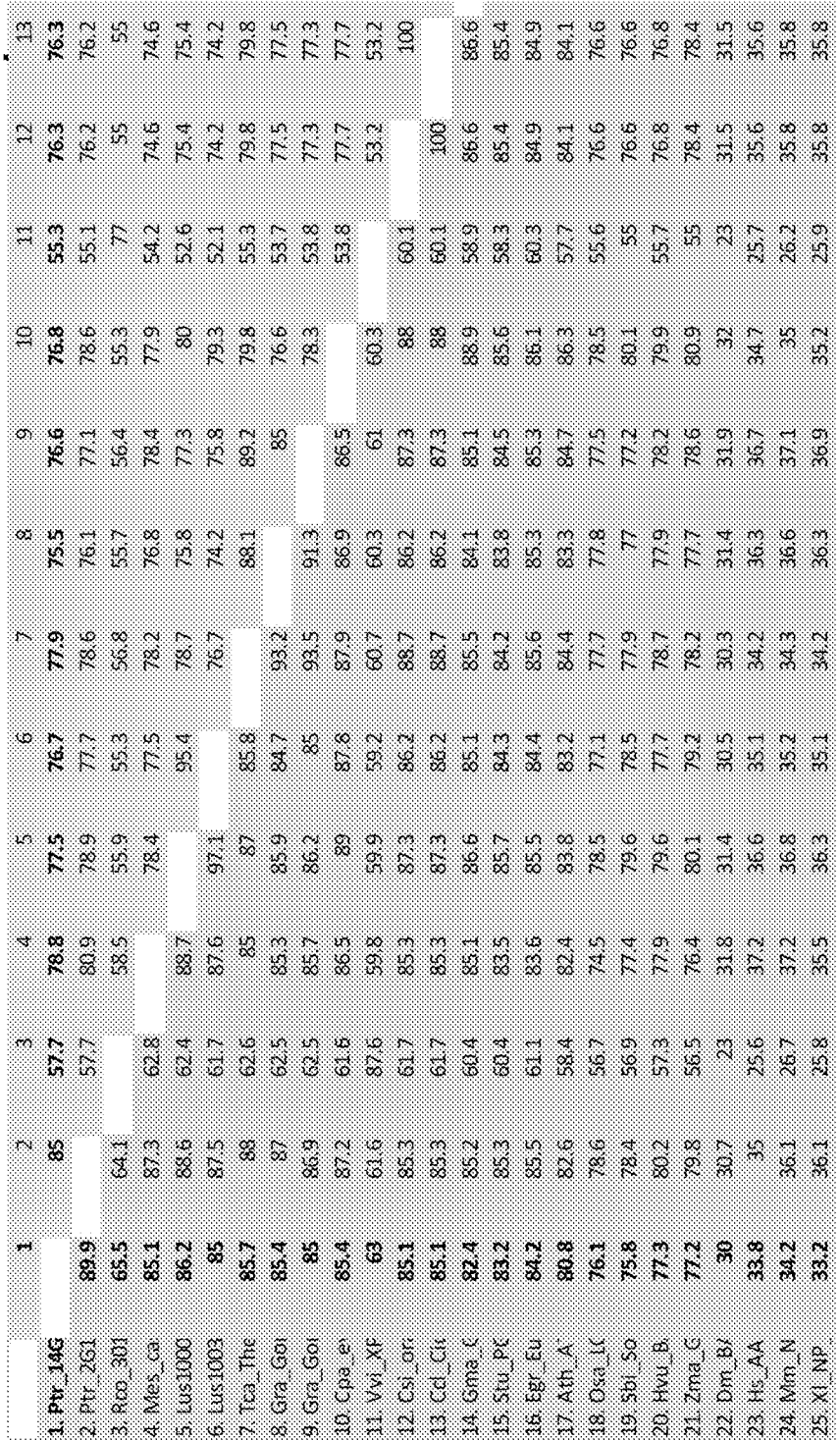
FIG. 3. Species alignment matrix showing percent amino acid identity and percent amino acid similarity across species for the alignment in FIGS. 2A-2K. Numbers 1-25 in both the left hand column and across the top row correspond to the sequences in FIGS. 2A-2K as follows: 1. SEQ ID NO: 2. 2. SEQ ID NO: 5. 3. SEQ ID NO: 7. 4. SEQ ID NO: 8. 5. SEQ ID NO: 9. 6. SEQ ID NO: 10. 7. SEQ ID NO: 11. 8. SEQ ID NO: 12. 9. SEQ ID NO: 13. 10. SEQ ID NO: 14. 11. SEQ ID NO: 15. 12. SEQ ID NO: 16. 13. SEQ ID NO: 17. 14. SEQ ID NO: 18. 15. SEQ ID NO: 19. 16. SEQ ID NO: 20. 17. SEQ ID NO: 6. 18. SEQ ID NO: 21. 19. SEQ ID NO: 22. 20. SEQ ID NO: 23. 21. SEQ ID NO: 24. 22. SEQ ID NO: 25. 23. SEQ ID NO: 26. 24. SEQ ID NO: 27. 25. SEQ ID NO: 28.
Figure 4:
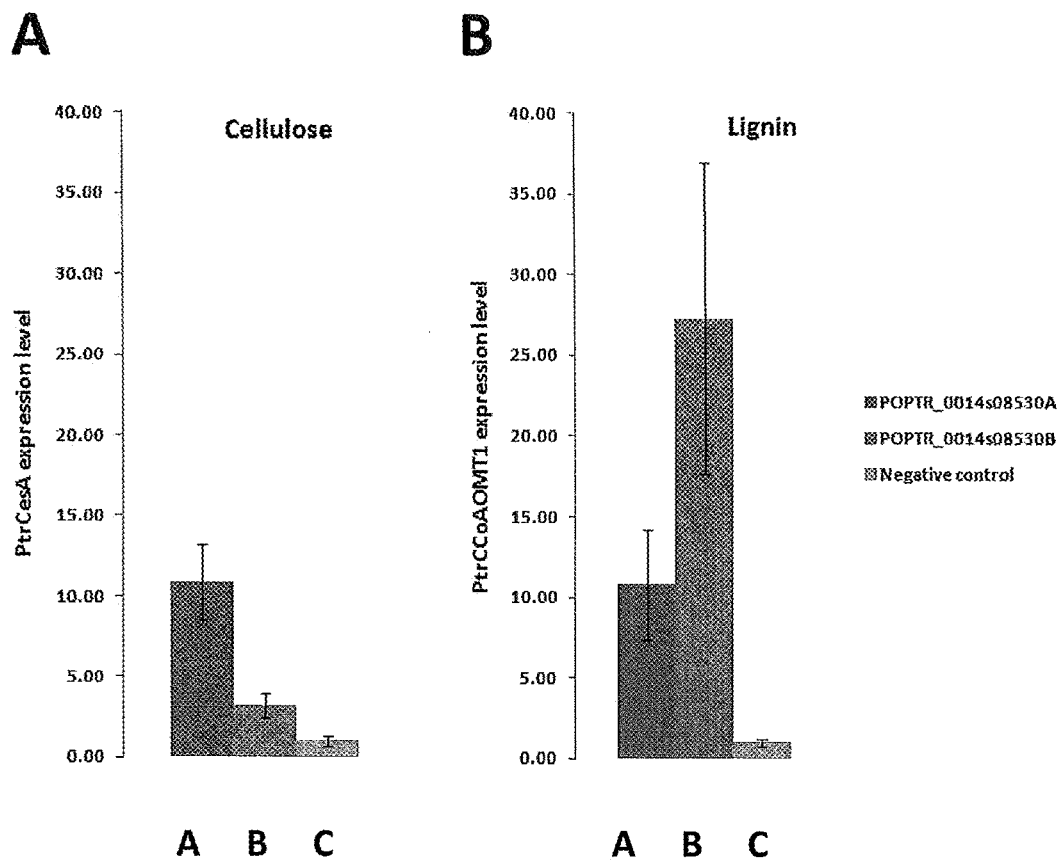
FIG. 4. Results of protoplast assays in *Populus* protoplasts transfected with Allele A (POPTR_0014s08530A) or Allele B (POPTR_0014s08530B). The negative control for (A) and (B) is transfection with an empty vector. Expression of *P. trichocarpa* cellulose synthase (PtrCesA8.

The inventors used protoplast transient expression assays in *Populus* to assess activation of marker genes by alternate alleles of the *Angustifolia* CtBP Potri.014G089400 locus. Results of the protoplast assay suggested that the allele derived from BESC-470 had significantly more activation of the CesA8 marker gene compared to the shorter PolyQ allele. The opposite was true when evaluating activation of the CcoAOMT1 marker gene, where the shorter PolyQ allele showed significantly higher activation of the lignin pathway marker gene (FIG. 4). These results indicate that this gene is involved in concurrent activation/repression of the cellulose and lignin biosynthetic pathway.

The *Angustifolia* CtBP gene was significantly associated with glucose and xylose release in both the native environment and Corvallis common garden. Based on transcript and

TABLE 2

SNP-trait associations across different environments for Potri.014G089400 locus

| | Infinium array | | | Re-sequencing | | |
|---|---|---|---|---|---|---|
| Location | SNP marker | p-value | Trait | SNP marker | p-value | Trait |
| Corvallis | scaffold_14_7043301 | 1.06E-05 | Xylose release | scaffold_14_7041563 | 4.63E-04* | 5-carbon sugars |
| Native | scaffold_14_7044284 | 6.84E-04 | Glucose/xylose | scaffold_14_7044259 | 5.36E-04* | 6-carbon sugars |

An *Angustifolia* C-terminus binding protein (CtBP) transcription factor, Potri.014G089400, harbored SNPs from the Infinium array that were significantly associated with xylose release (p=1.06E-05) at the chromosome-wise threshold in the Corvallis environment and with glucose/xylose release (p=6.84E-04) at the QTL-wise threshold in native environments. There were no significant associations when reanaproteome profiling of developing xylem in *Populus*, this gene was reported to have high EST expression and protein abundance in the xylem including tissues under tension (Kalluri, U C, et al., *Proteomics,* 9:4871-4880 (2009)). Subsequent cDNA cloning and sequencing using trees carrying alternate alleles of the two SNPs revealed a tri-nucleotide CAGCAG repeat polymorphism leading to variable PolyQ length polymorphism as well as a single amino acid substitution between the two alternate alleles. Protoplast assays using alternate alleles suggested that the allele with the expanded PolyQ sequence displayed significantly higher activation of the cellulose pathway marker gene CesA8, but had lower activation of the lignin pathway CcoAOMT1 marker gene compared to the alternate allele. Although the amino acid substitution cannot be ruled out at this stage, effects of variable-length PolyQ stretches on transcription factor activity have been documented in diverse organisms (Atanesyan et al., 2012). In addition, activator/repressor activity of *Angustifolia* CtBP transcription factor has also been reported in *Arabidopsis*, where the *Arabidopsis* ortholog was shown to regulate leaf-cell expansion, arrangement of cortical microtubules and the expression of genes involved in cell wall formation (Chinnadurai, G, *BioEssays* 25:9-12 (2002); Kim, G-T, et al., *The EMBO J* 21:1267-1279 (2002)).

The enhancement of transcription factor activity by the PolyQ stretch suggests naturally enhanced activity as well as opportunities to engineer multiple tandem PolyQ segments for enhanced versions of transcription factors regulating the expression of genes affecting economically important traits. In applied breeding programs, genotypes carrying enhancer mutations could be strategically used in marker assisted breeding schemes to pyramid complementary mutations that may result in superior phenotypes.

SEQUENCE LISTING

<160> NUMBER OF SEQ ID NOS: 39

<210> SEQ ID NO 1
<211> LENGTH: 1974
<212> TYPE: DNA
<213> ORGANISM: Populus trichocarpa

<400> SEQUENCE: 1

```
atgagcgcca cgactaccag atctttagcg acaatgtcac accgccgtaa cactaacact      60
cctcctcctc cacagcaaca gcaacagcaa cagcaacaac aacaacaaca acgtctccct     120
cttgttgtca ctctcaactg catcgaagat tttgccatcg aacaagactc cttatccggc     180
gtcgctttaa ttgaacacgt ccctctcggc cgcctctccg atggcaagat cgaatctgcc     240
gctgccgtcc tcctccattc actcgcttac ctcccacgcg ccgcccaacg ccgtctccgt     300
ccttaccagc tcatcctatg cctggggtcg gctgaccgag ctgtcgactc cgctctcgct     360
gccgatttag gtctccggct tgtacacgtg gatacttctc gagccgagga gatcgctgat     420
acggttatgg ctttgtttct aggcttgctg cgccggacgc atttgttgtc aagacatgcc     480
ttatcagctt ccggttggct tggctcgctg cagccgcttt gtagaggaat gaggaggtgt     540
agaggtttgg tattgggcat tgttggtaga tctgcatcag ctagatcttt ggctactaga     600
agcttagctt ttaaaatgag tgtgctgtat tttgatgtac acgaggggcc aggaaaatta     660
accaggtctt ctattacatt tcctttagct gctcgaagaa tggatactct taatgattta     720
ctggctgcaa gtgatcttat ttcacttcac tgtgctttaa ctaatgaaac tgttcagatt     780
atcaatgaag agtgcttgca acatataaag ccaggggcat ttcttgtgaa tacgggcagc     840
agtcagctgc tggatgattg tgctttgaag caacttctga ttgatgggac cttggccggt     900
tgtgccctgg atggtgctga agggccacag tggatggaag catgggtaaa agagatgccc     960
aatgtattga tacttccacg cagtgcagat tacagtgaag aagtgtggat ggagataagg    1020
gaaaaagcta tctctattct gcagtcattc ttctttgatg ggatcgtacc aaagaatgct    1080
gtttctgatg aggaagggga agaaagtgaa ataggtgatg aaagtgaaca atttcacagg    1140
caagacaaag aaagtactct gcaggattct gttggtgagc aattgaccga tgatattcag    1200
ctaactccag aaacctctcg caaaaaagtc agtggtcaat caatagaatc taccagccaa    1260
gctcagggtt ctggcatgtc tcaaaataca accacaagat ctgatgaaag acgcagccga    1320
tcaggcaaga aggcaaaaaa aagacatggc cgtcaaaaac ctcgacagaa atcagacaat    1380
ccttctcaat tagagaaaga aagtacttca catcaagaag atgatactgc tatgagtggc    1440
agtgatcaag tctccagttc tcggtttgct tcccctgaag actcaaggag taggaaaaca    1500
ccaatagaat taatgcaaga atcaagttca ggccagcttt caagatcagg caagaggctc    1560
```

```
agtggaaagt ctgatgagct gctcaaagat gggcacatta tagctttata tgcaagagat    1620
cgccctgcac tccatgtttc caggcaaaga gctaaaggag gtggttggtt cctggatgct    1680
ctgtcaaatg taacaaaaag agatcctgca gcccagttcc ttgttgtttt cagaaacaag    1740
gacacaattg ggttgcgctc ttttgctgct ggtggaaagt tattgcagat taacaggaga    1800
atggaatttg ttttcaccag tcacagtttt gatgtttggg agagttggat gttggaaggt    1860
tctttggatg aatgcaggct ggttaactgt agaaatcctt tggctatttt ggatgcacgt    1920
gtcgagattc tggccgccat agcggaagat gatggtgtta ctcgttggct agat          1974

<210> SEQ ID NO 2
<211> LENGTH: 658
<212> TYPE: PRT
<213> ORGANISM: Populus trichocarpa

<400> SEQUENCE: 2
```

Met Ser Ala Thr Thr Thr Arg Ser Leu Ala Thr Met Ser His Arg Arg
1               5                   10                  15

Asn Thr Asn Thr Pro Pro Pro Gln Gln Gln Gln Gln Gln Gln Gln Gln
            20                  25                  30

Gln Gln Gln Gln Arg Leu Pro Leu Val Val Thr Leu Asn Cys Ile
        35                  40                  45

Glu Asp Phe Ala Ile Glu Gln Asp Ser Leu Ser Gly Val Ala Leu Ile
50                  55                  60

Glu His Val Pro Leu Gly Arg Leu Ser Asp Gly Lys Ile Glu Ser Ala
65                  70                  75                  80

Ala Ala Val Leu Leu His Ser Leu Ala Tyr Leu Pro Arg Ala Ala Gln
            85                  90                  95

Arg Arg Leu Arg Pro Tyr Gln Leu Ile Leu Cys Leu Gly Ser Ala Asp
        100                 105                 110

Arg Ala Val Asp Ser Ala Leu Ala Ala Asp Leu Gly Leu Arg Leu Val
    115                 120                 125

His Val Asp Thr Ser Arg Ala Glu Glu Ile Ala Asp Thr Val Met Ala
130                 135                 140

Leu Phe Leu Gly Leu Leu Arg Arg Thr His Leu Leu Ser Arg His Ala
145                 150                 155                 160

Leu Ser Ala Ser Gly Trp Leu Gly Ser Leu Gln Pro Leu Cys Arg Gly
            165                 170                 175

Met Arg Arg Cys Arg Gly Leu Val Leu Gly Ile Val Gly Arg Ser Ala
        180                 185                 190

Ser Ala Arg Ser Leu Ala Thr Arg Ser Leu Ala Phe Lys Met Ser Val
    195                 200                 205

Leu Tyr Phe Asp Val His Glu Gly Pro Gly Lys Leu Thr Arg Ser Ser
210                 215                 220

Ile Thr Phe Pro Leu Ala Ala Arg Arg Met Asp Thr Leu Asn Asp Leu
225                 230                 235                 240

Leu Ala Ala Ser Asp Leu Ile Ser Leu His Cys Ala Leu Thr Asn Glu
            245                 250                 255

Thr Val Gln Ile Ile Asn Glu Glu Cys Leu Gln His Ile Lys Pro Gly
        260                 265                 270

Ala Phe Leu Val Asn Thr Gly Ser Ser Gln Leu Leu Asp Asp Cys Ala
    275                 280                 285

Leu Lys Gln Leu Leu Ile Asp Gly Thr Leu Ala Gly Cys Ala Leu Asp
290                 295                 300

Gly Ala Glu Gly Pro Gln Trp Met Glu Ala Trp Val Lys Glu Met Pro
305                 310                 315                 320

Asn Val Leu Ile Leu Pro Arg Ser Ala Asp Tyr Ser Glu Glu Val Trp
            325                 330                 335

Met Glu Ile Arg Glu Lys Ala Ile Ser Ile Leu Gln Ser Phe Phe Phe
        340                 345                 350

Asp Gly Ile Val Pro Lys Asn Ala Val Ser Asp Glu Glu Gly Glu Glu
    355                 360                 365

Ser Glu Ile Gly Asp Glu Ser Glu Gln Phe His Arg Gln Asp Lys Glu
370                 375                 380

Ser Thr Leu Gln Asp Ser Val Gly Glu Gln Leu Thr Asp Asp Ile Gln
385                 390                 395                 400

Leu Thr Pro Glu Thr Ser Arg Lys Lys Val Ser Gly Gln Ser Ile Glu
            405                 410                 415

Ser Thr Ser Gln Ala Gln Gly Ser Gly Met Ser Gln Asn Thr Thr Thr
        420                 425                 430

Arg Ser Asp Glu Arg Arg Ser Arg Ser Gly Lys Lys Ala Lys Lys Arg
    435                 440                 445

His Gly Arg Gln Lys Pro Arg Gln Lys Ser Asp Asn Pro Ser Gln Leu
450                 455                 460

Glu Lys Glu Ser Thr Ser His Gln Glu Asp Asp Thr Ala Met Ser Gly
465                 470                 475                 480

Ser Asp Gln Val Ser Ser Ser Arg Phe Ala Ser Pro Glu Asp Ser Arg
            485                 490                 495

Ser Arg Lys Thr Pro Ile Glu Leu Met Gln Glu Ser Ser Gly Gln
        500                 505                 510

Leu Ser Arg Ser Gly Lys Arg Leu Ser Gly Lys Ser Asp Glu Leu Leu
    515                 520                 525

Lys Asp Gly His Ile Ile Ala Leu Tyr Ala Arg Asp Arg Pro Ala Leu
530                 535                 540

His Val Ser Arg Gln Arg Ala Lys Gly Gly Gly Trp Phe Leu Asp Ala
545                 550                 555                 560

Leu Ser Asn Val Thr Lys Arg Asp Pro Ala Ala Gln Phe Leu Val Val
            565                 570                 575

Phe Arg Asn Lys Asp Thr Ile Gly Leu Arg Ser Phe Ala Ala Gly Gly
        580                 585                 590

Lys Leu Leu Gln Ile Asn Arg Arg Met Glu Phe Val Phe Thr Ser His
    595                 600                 605

Ser Phe Asp Val Trp Glu Ser Trp Met Leu Glu Gly Ser Leu Asp Glu
610                 615                 620

Cys Arg Leu Val Asn Cys Arg Asn Pro Leu Ala Ile Leu Asp Ala Arg
625                 630                 635                 640

Val Glu Ile Leu Ala Ala Ile Ala Glu Asp Asp Gly Val Thr Arg Trp
            645                 650                 655

Leu Asp

<210> SEQ ID NO 3
<211> LENGTH: 1980
<212> TYPE: DNA
<213> ORGANISM: Populus trichocarpa

<400> SEQUENCE: 3
atgagcgcca cgactaccag atctttagcg acaatgtcac accgccgtaa cactaacact    60

| | |
|---|---|
| cctcctcctc cacagcaaca gcaacagcaa cagcaacagc agcaacaaca acaacaacgt | 120 |
| ctccctcttg ttgtcactct caactgcatc gaagattttg ccatcgaaca agactcctta | 180 |
| tccggcgtcg ctttaattga acacgtccct ctcggccgcc tctccgatgg caagatcgaa | 240 |
| tctgccgctg ccgtcctcct ccattcactc gcttacctcc cacgcgccgc caacgccgt | 300 |
| ctccgtcctt accagctcat cctatgcctg gggtcggctg accgagctgt cgactccgct | 360 |
| ctcgctgccg atttaggtct ccggcttgta cacgtggata cttctcgagc cgaggagatc | 420 |
| gctgatacgg ttatggcttt gtttctaggc ttgctgcgcc ggacgcattt gttgtcaaga | 480 |
| catgccttat cagcttccgg ttggcttggc tcgctgcagc cgctttgtag aggaatgagg | 540 |
| aggtgtagag gtttggtatt gggcattgtt ggtagatctg catcagctag atctttggct | 600 |
| actagaagct tagcttttaa aatgagtgtg ctgtatttg atgtacacga ggggccagga | 660 |
| aaattaacca ggtcttctat tacatttcct ttagctgctc gaagaatgga tactcttaat | 720 |
| gatttactgg ctgcaagtga tcttatttca cttcactgtg ctttaactaa tgaaactgtt | 780 |
| cagattatca atgaagagtg cttgcaacat ataaagccag gggcatttct tgtgaatacg | 840 |
| ggcagcagtc agctgctgga tgattgtgct tgaagcaac ttctgattga tgggaccttg | 900 |
| gccggttgtg ccctggatgg tgctgaaggg ccacagtgga tggaagcatg ggtaaaagag | 960 |
| atgcccaatg tattgatact tccacgcagt gcagattaca gtgaagaagt gtggatggag | 1020 |
| ataagggaaa aagctatctc tattctgcag tcattcttct ttgatgggat cgtaccaaag | 1080 |
| aatgctgttt ctgatgagga aggggaagaa agtgaaatag gtgatgaaag tgaacaattt | 1140 |
| cacaggcaag acaaagaaag tactctgcag gattctgttg gtgagcaatt gaccgatgat | 1200 |
| attcagctaa ctccagaaac ctctcgcaaa aaagtcagtg gtcaatcaat agaatctacc | 1260 |
| agccaagctc agggttctgg catgtctcaa atacaaccca aagatctga tgaaagacgc | 1320 |
| agccgatcag gcaagaaggc aaaaaaaaga catggccgtc aaaaacctcg acagaaatca | 1380 |
| gacaatcctt ctcaattaga gaagaaagt acttcacatc aagaagatga tactgctatg | 1440 |
| agtggcagtg atcaagtctc cagttctcgg tttgcttccc ctgaagactc aaggagtagg | 1500 |
| aaaacaccaa tagaattaat gcaagaatca agttcaggcc agctttcaag atcaggcaag | 1560 |
| aggctcagtg gaaagtctga tgagctgctc aaagatgggc acattatagc tttatatgca | 1620 |
| agagatcgcc ctgcactcca tgtttccagg caaagagcta aaggaggtgg ttggttcctg | 1680 |
| gatgctctgt caaatgtaac aaaaagagat cctgcagccc agttccttgt tgttttcaga | 1740 |
| aacaaggaca caattgggtt gcgctctttt gctgctggtg gaaagttatt gcagattaac | 1800 |
| aggagaatgg aatttgtttt caccagtcac agttttgatg tttgggagag ttggatgttg | 1860 |
| gaaggttctt tggatgaatg caggctggtt aactgtagaa atcctttggc tattttggat | 1920 |
| gcacgtgtcg agattctggc caccatagcg gaagatgatg gtgttactcg ttggctagat | 1980 |

<210> SEQ ID NO 4
<211> LENGTH: 660
<212> TYPE: PRT
<213> ORGANISM: Populus trichocarpa

<400> SEQUENCE: 4

Met Ser Ala Thr Thr Thr Arg Ser Leu Ala Thr Met Ser His Arg Arg
1               5                   10                  15

Asn Thr Asn Thr Pro Pro Pro Pro Gln Gln Gln Gln Gln Gln Gln Gln
            20                  25                  30

Gln Gln Gln Gln Gln Gln Gln Arg Leu Pro Leu Val Val Thr Leu Asn

```
              35                  40                  45
Cys Ile Glu Asp Phe Ala Ile Glu Gln Asp Ser Leu Ser Gly Val Ala
 50                  55                  60

Leu Ile Glu His Val Pro Leu Gly Arg Leu Ser Asp Gly Lys Ile Glu
 65                  70                  75                  80

Ser Ala Ala Ala Val Leu Leu His Ser Leu Ala Tyr Leu Pro Arg Ala
                 85                  90                  95

Ala Gln Arg Arg Leu Arg Pro Tyr Gln Leu Ile Leu Cys Leu Gly Ser
            100                 105                 110

Ala Asp Arg Ala Val Asp Ser Ala Leu Ala Ala Asp Leu Gly Leu Arg
            115                 120                 125

Leu Val His Val Asp Thr Ser Arg Ala Glu Glu Ile Ala Asp Thr Val
130                 135                 140

Met Ala Leu Phe Leu Gly Leu Leu Arg Arg Thr His Leu Leu Ser Arg
145                 150                 155                 160

His Ala Leu Ser Ala Ser Gly Trp Leu Gly Ser Leu Gln Pro Leu Cys
                165                 170                 175

Arg Gly Met Arg Arg Cys Arg Gly Leu Val Leu Gly Ile Val Gly Arg
            180                 185                 190

Ser Ala Ser Ala Arg Ser Leu Ala Thr Arg Ser Leu Ala Phe Lys Met
            195                 200                 205

Ser Val Leu Tyr Phe Asp Val His Glu Gly Pro Gly Lys Leu Thr Arg
210                 215                 220

Ser Ser Ile Thr Phe Pro Leu Ala Ala Arg Arg Met Asp Thr Leu Asn
225                 230                 235                 240

Asp Leu Leu Ala Ala Ser Asp Leu Ile Ser Leu His Cys Ala Leu Thr
                245                 250                 255

Asn Glu Thr Val Gln Ile Ile Asn Glu Glu Cys Leu Gln His Ile Lys
            260                 265                 270

Pro Gly Ala Phe Leu Val Asn Thr Gly Ser Ser Gln Leu Leu Asp Asp
            275                 280                 285

Cys Ala Leu Lys Gln Leu Leu Ile Asp Gly Thr Leu Ala Gly Cys Ala
290                 295                 300

Leu Asp Gly Ala Glu Gly Pro Gln Trp Met Glu Ala Trp Val Lys Glu
305                 310                 315                 320

Met Pro Asn Val Leu Ile Leu Pro Arg Ser Ala Asp Tyr Ser Glu Glu
                325                 330                 335

Val Trp Met Glu Ile Arg Glu Lys Ala Ile Ser Ile Leu Gln Ser Phe
            340                 345                 350

Phe Phe Asp Gly Ile Val Pro Lys Asn Ala Val Ser Asp Glu Glu Gly
            355                 360                 365

Glu Glu Ser Glu Ile Gly Asp Glu Ser Glu Gln Phe His Arg Gln Asp
            370                 375                 380

Lys Glu Ser Thr Leu Gln Asp Ser Val Gly Glu Gln Leu Thr Asp Asp
385                 390                 395                 400

Ile Gln Leu Thr Pro Glu Thr Ser Arg Lys Lys Val Ser Gly Gln Ser
                405                 410                 415

Ile Glu Ser Thr Ser Gln Ala Gln Gly Ser Gly Met Ser Gln Asn Thr
            420                 425                 430

Thr Thr Arg Ser Asp Glu Arg Arg Ser Arg Ser Gly Lys Lys Ala Lys
            435                 440                 445

Lys Arg His Gly Arg Gln Lys Pro Arg Gln Lys Ser Asp Asn Pro Ser
            450                 455                 460
```

```
Gln Leu Glu Lys Glu Ser Thr Ser His Gln Glu Asp Asp Thr Ala Met
465                 470                 475                 480

Ser Gly Ser Asp Gln Val Ser Ser Arg Phe Ala Ser Pro Glu Asp
                485                 490                 495

Ser Arg Ser Arg Lys Thr Pro Ile Glu Leu Met Gln Glu Ser Ser Ser
                500                 505                 510

Gly Gln Leu Ser Arg Ser Gly Lys Arg Leu Ser Gly Lys Ser Asp Glu
            515                 520                 525

Leu Leu Lys Asp Gly His Ile Ile Ala Leu Tyr Ala Arg Asp Arg Pro
530                 535                 540

Ala Leu His Val Ser Arg Gln Arg Ala Lys Gly Gly Gly Trp Phe Leu
545                 550                 555                 560

Asp Ala Leu Ser Asn Val Thr Lys Arg Asp Pro Ala Ala Gln Phe Leu
                565                 570                 575

Val Val Phe Arg Asn Lys Asp Thr Ile Gly Leu Arg Ser Phe Ala Ala
                580                 585                 590

Gly Gly Lys Leu Leu Gln Ile Asn Arg Arg Met Glu Phe Val Phe Thr
            595                 600                 605

Ser His Ser Phe Asp Val Trp Glu Ser Trp Met Leu Glu Gly Ser Leu
610                 615                 620

Asp Glu Cys Arg Leu Val Asn Cys Arg Asn Pro Leu Ala Ile Leu Asp
625                 630                 635                 640

Ala Arg Val Glu Ile Leu Ala Thr Ile Ala Glu Asp Asp Gly Val Thr
                645                 650                 655

Arg Trp Leu Asp
            660

<210> SEQ ID NO 5
<211> LENGTH: 648
<212> TYPE: PRT
<213> ORGANISM: Populus trichocarpa

<400> SEQUENCE: 5

Met Ser Ala Thr Asn Asn Arg Ser Ser Thr Thr Met Ser Leu His His
1               5                   10                  15

Leu Thr Thr Asn Pro Pro Pro Gln Gln Asn Leu Pro Leu Val Val
            20                  25                  30

Thr Leu Asn Cys Ile Glu Asp Cys Ala Ile Glu Gln Asp Ser Leu Ser
            35                  40                  45

Gly Val Ala Ser Ile Glu His Val Pro Leu Ser Arg Leu Ser Gly Gly
        50                  55                  60

Lys Ile Glu Ser Ala Ala Ala Val Leu Leu His Ser Leu Ala Tyr Leu
65                  70                  75                  80

Pro Arg Ala Ala Gln Arg Arg Leu Arg Pro Tyr Gln Leu Ile Leu Cys
                85                  90                  95

Leu Gly Ser Ala Asp Arg Ala Val Asp Ser Ala Leu Ala Ala Asp Leu
            100                 105                 110

Gly Leu Arg Leu Val His Val Asp Asn Ser Arg Ala Glu Glu Ile Ala
        115                 120                 125

Asp Thr Val Met Ala Leu Phe Leu Gly Leu Leu Arg Arg Thr His Leu
    130                 135                 140

Leu Ser Arg His Thr Leu Ser Ala Ser Gly Trp Leu Gly Ser Val Gln
145                 150                 155                 160

Pro Leu Cys Arg Gly Met Arg Arg Cys Arg Gly Leu Val Leu Gly Ile
```

```
                    165                 170                 175
Val Gly Arg Ser Ala Ser Ala Lys Ser Leu Ala Thr Arg Ser Leu Ala
            180                 185                 190

Phe Lys Ile Ser Val Leu Tyr Phe Asp Val His Glu Gly Pro Gly Ile
        195                 200                 205

Leu Ser Arg Ser Ser Ile Ala Phe Pro Ser Ala Ala Arg Arg Met Asp
    210                 215                 220

Thr Leu Asn Asp Leu Leu Ala Ala Ser Asp Leu Ile Ser Leu His Cys
225                 230                 235                 240

Ala Leu Thr Asn Glu Thr Val Gln Ile Ile Ser Ala Glu Cys Leu Gln
            245                 250                 255

His Ile Lys Pro Gly Ala Phe Leu Val Asn Thr Gly Ser Ser Gln Leu
        260                 265                 270

Leu Asp Asp Cys Ala Leu Lys Gln Leu Leu Ile Asp Gly Thr Leu Ala
    275                 280                 285

Gly Cys Ala Leu Asp Gly Ala Glu Gly Pro Gln Trp Met Glu Ala Trp
290                 295                 300

Val Lys Glu Met Pro Asn Val Leu Ile Leu Pro Arg Ser Ala Asp Tyr
305                 310                 315                 320

Ser Glu Glu Val Trp Met Glu Ile Arg Asp Lys Ala Ile Ser Ile Leu
            325                 330                 335

Gln Ser Phe Phe Leu Asp Gly Thr Val Pro Lys Asn Ala Val Ser Asp
        340                 345                 350

Glu Glu Glu Glu Glu Ser Glu Ile Gly Glu Glu Ser Asp Gln Phe His
    355                 360                 365

Arg Gln Asp Lys Glu Ser Thr Leu Gln Asp Ser Val Val Glu Gln Leu
370                 375                 380

Thr Asp Asp Val Gln Val Thr Leu Glu Ser Tyr His Lys Lys Val Ile
385                 390                 395                 400

Ser Gln Ser Ile Glu Ser Thr Ser Lys Ala Gln Val Ser Gly Met Ser
            405                 410                 415

Gln Asn Met Ala Thr Arg Thr Glu Gly Arg Arg Asn Arg Leu Gly Lys
        420                 425                 430

Lys Ala Lys Lys Arg His Gly His Gln Lys Ser Gln Lys Ser Asp
    435                 440                 445

Asp Pro Ser Gln Leu Glu Lys Glu Ile Thr Ser His Gln Glu Asp Asp
450                 455                 460

Thr Ala Met Ser Gly Thr Asp Gln Val Leu Ser Ser Gly Ser Arg Phe
465                 470                 475                 480

Ala Ser Pro Glu Asp Ser Arg Ser Arg Lys Thr Pro Ile Glu Leu Thr
            485                 490                 495

Gln Asp Pro Thr Ser Gly Gln Leu Ser Arg Ser Gly Lys Lys Leu Ser
        500                 505                 510

Gly Lys Ser Asp Lys Leu Leu Lys Asp Gly His Ile Ile Ala Leu Tyr
    515                 520                 525

Ala Arg Asp His Ser Ala Leu His Val Ser Arg Gln Arg Val Lys Gly
530                 535                 540

Gly Gly Trp Phe Leu Asp Ala Met Ser Asn Val Thr Lys Arg Asp Pro
545                 550                 555                 560

Ala Ala Gln Phe Leu Val Val Phe Arg Ser Asp Thr Ile Gly Leu
            565                 570                 575

Arg Ser Phe Ala Ala Gly Gly Lys Leu Leu Gln Ile Asn Arg Arg Thr
        580                 585                 590
```

```
Glu Phe Val Phe Ala Ser His Ser Phe Asp Val Trp Glu Ser Trp Met
            595                 600                 605

Leu Glu Gly Ser Leu Glu Glu Cys Arg Leu Val Asn Cys Arg Asn Pro
610                 615                 620

Leu Ala Val Leu Glu Val Arg Ile Glu Ile Leu Ala Ala Val Gly Glu
625                 630                 635                 640

Asp Gly Val Ser Arg Trp Leu Asp
                645

<210> SEQ ID NO 6
<211> LENGTH: 636
<212> TYPE: PRT
<213> ORGANISM: Arabidopsis thaliana

<400> SEQUENCE: 6

Met Ser Lys Ile Arg Ser Ser Ala Thr Met Pro His Arg Asp Gln Pro
1               5                   10                  15

Ser Pro Ala Ser Pro His Val Val Thr Leu Asn Cys Ile Glu Asp Cys
                20                  25                  30

Ala Leu Glu Gln Asp Ser Leu Ala Gly Val Ala Gly Val Glu Tyr Val
            35                  40                  45

Pro Leu Ser Arg Ile Ala Asp Gly Lys Ile Glu Ser Ala Thr Ala Val
        50                  55                  60

Leu Leu His Ser Leu Ala Tyr Leu Pro Arg Ala Ala Gln Arg Arg Leu
65                  70                  75                  80

Arg Pro His Gln Leu Ile Leu Cys Leu Gly Ser Ala Asp Arg Ala Val
                85                  90                  95

Asp Ser Thr Leu Ala Ala Asp Leu Gly Leu Arg Leu Val His Val Asp
            100                 105                 110

Thr Ser Arg Ala Glu Glu Ile Ala Asp Thr Val Met Ala Leu Ile Leu
        115                 120                 125

Gly Leu Leu Arg Arg Thr His Leu Leu Ser Arg His Ala Leu Ser Ala
130                 135                 140

Ser Gly Trp Leu Gly Ser Leu Gln Pro Leu Cys Arg Gly Met Arg Arg
145                 150                 155                 160

Cys Arg Gly Met Val Leu Gly Ile Val Gly Arg Ser Val Ser Ala Arg
                165                 170                 175

Tyr Leu Ala Ser Arg Ser Leu Ala Phe Lys Met Ser Val Leu Tyr Phe
            180                 185                 190

Asp Val Pro Glu Gly Asp Glu Glu Arg Ile Arg Pro Ser Arg Phe Pro
        195                 200                 205

Arg Ala Ala Arg Arg Met Asp Thr Leu Asn Asp Leu Leu Ala Ala Ser
210                 215                 220

Asp Val Ile Ser Leu His Cys Ala Leu Thr Asn Asp Thr Val Gln Ile
225                 230                 235                 240

Leu Asn Ala Glu Cys Leu Gln His Ile Lys Pro Gly Ala Phe Leu Val
                245                 250                 255

Asn Thr Gly Ser Cys Gln Leu Leu Asp Asp Cys Ala Val Lys Gln Leu
            260                 265                 270

Leu Ile Asp Gly Thr Ile Ala Gly Cys Ala Leu Asp Gly Ala Glu Gly
        275                 280                 285

Pro Gln Trp Met Glu Ala Trp Val Lys Glu Met Pro Asn Val Leu Ile
290                 295                 300

Leu Pro Arg Ser Ala Asp Tyr Ser Glu Glu Val Trp Met Glu Ile Arg
```

```
            305                 310                 315                 320
Glu Lys Ala Ile Ser Ile Leu His Ser Phe Phe Leu Asp Gly Val Ile
                325                 330                 335
Pro Ser Asn Thr Val Ser Asp Glu Glu Val Glu Glu Ser Glu Ala Ser
                340                 345                 350
Glu Glu Glu Glu Gln Ser Pro Ser Lys His Glu Lys Leu Ala Ile Val
                355                 360                 365
Glu Ser Thr Ser Arg Gln Gln Gly Glu Ser Thr Leu Thr Ser Thr Glu
                370                 375                 380
Ile Val Arg Arg Glu Ala Ser Glu Leu Lys Glu Ser Leu Ser Pro Gly
385                 390                 395                 400
Gln Gln His Val Ser Gln Asn Thr Ala Val Lys Pro Glu Gly Arg Arg
                405                 410                 415
Ser Arg Ser Gly Lys Lys Ala Lys Lys Arg His Ser Gln Lys Tyr
                420                 425                 430
Met Gln Lys Thr Asp Gly Ser Ser Gly Leu Asn Glu Glu Ser Thr Ser
                435                 440                 445
Arg Arg Asp Asp Ile Ala Met Ser Asp Thr Glu Glu Val Leu Ser Ser
450                 455                 460
Ser Ser Arg Cys Ala Ser Pro Glu Asp Ser Arg Ser Arg Lys Thr Pro
465                 470                 475                 480
Leu Glu Val Met Gln Glu Ser Ser Pro Asn Gln Leu Val Met Ser Ser
                485                 490                 495
Lys Lys Phe Ile Gly Lys Ser Ser Glu Leu Leu Lys Asp Gly Tyr Val
                500                 505                 510
Val Ala Leu Tyr Ala Lys Asp Leu Ser Gly Leu His Val Ser Arg Gln
                515                 520                 525
Arg Thr Lys Asn Gly Gly Trp Phe Leu Asp Thr Leu Ser Asn Val Ser
                530                 535                 540
Lys Arg Asp Pro Ala Ala Gln Phe Ile Ile Ala Tyr Arg Asn Lys Asp
545                 550                 555                 560
Thr Val Gly Leu Arg Ser Phe Ala Ala Gly Gly Lys Leu Leu Gln Ile
                565                 570                 575
Asn Arg Arg Met Glu Phe Val Phe Ala Ser His Ser Phe Asp Val Trp
                580                 585                 590
Glu Ser Trp Ser Leu Gly Leu Asp Glu Cys Arg Leu Val Asn
                595                 600                 605
Cys Arg Asn Ser Ser Ala Val Leu Asp Val Arg Val Glu Ile Leu Ala
                610                 615                 620
Met Val Gly Asp Asp Gly Ile Thr Arg Trp Ile Asp
625                 630                 635

<210> SEQ ID NO 7
<211> LENGTH: 930
<212> TYPE: PRT
<213> ORGANISM: Ricinus communis

<400> SEQUENCE: 7

Met Asn Phe Gln Glu Gln Glu Ser Asn Ser Tyr Asn Leu Ile Thr Ser
1               5                   10                  15
Ser Ala Thr Trp Leu Glu Ile Arg Leu Phe Tyr Val Arg Ile Thr Pro
                20                  25                  30
Cys Val Ile Asp Ser Val Pro Asp His Leu Thr Leu Arg His Leu Arg
                35                  40                  45
```

```
Arg Glu Ile Ser Thr Pro Leu Glu Ile Asn Gly Ser Arg Ile Pro Ala
 50                  55                  60
Ala Asp Ser Ala Ser Val Thr Leu Arg Arg Asp Arg Leu Asn Lys Glu
 65                  70                  75                  80
Ser Ser Glu Val Thr Tyr Val Ser Thr Asp Ser Val Arg Ile Thr Gly
                 85                  90                  95
Ala Leu Glu Phe Glu Val Ile Glu Glu Asn Asp Leu Phe Leu Cys Gly
                100                 105                 110
Ser Leu Glu Arg Ile Glu Ser Thr Thr Leu Trp Gly Asn Asp Ser Lys
            115                 120                 125
Thr Gly Trp Ser Met Glu Cys Tyr Met Ala Ala Ser Val Gly Glu Gly
130                 135                 140
Asn Ser Val Phe Phe Gln Pro Lys Leu Gly Val Ser Ala Pro Ala Ile
145                 150                 155                 160
Glu Val Tyr Ile Ala Gly Cys Cys Gly Gly Ile Pro Val Ile Leu Thr
                165                 170                 175
Lys Thr Ile Leu Val Ser Pro Arg Lys Lys Gly Ser Arg His Gly Met
            180                 185                 190
Leu Asp Ala Ile Pro Glu Asp Glu Met Glu Lys Glu His Asn Gly
        195                 200                 205
Asp Ala Ser Leu Arg Leu Arg Lys Val Gln Ile Ile Glu Ser Glu Gly
210                 215                 220
Asp Asp Ser Asp Leu Glu Lys Thr Gly Asn Arg Tyr Tyr Ser Asp
225                 230                 235                 240
Asp Met Tyr Tyr Gly Glu Asp Gln Leu Thr Trp Phe Asn Ala Gly
                245                 250                 255
Val Arg Val Gly Val Gly Ile Gly Leu Gly Met Cys Leu Gly Ile Gly
            260                 265                 270
Ile Gly Val Gly Leu Leu Met Arg Ser Tyr Gln Ala Thr Thr Arg Asn
        275                 280                 285
Phe Arg Arg Ser Thr Asn Ile Arg Ser Ser Ala Thr Met Ser His His
290                 295                 300
Lys Ser Ser Ser Gln Pro Leu Pro Leu Val Val Ser Leu Asn Cys Ile
305                 310                 315                 320
Glu Asp Cys Ser Ile Glu Gln Asp Ser Leu Ala Gly Val Ala Thr Val
                325                 330                 335
Glu His Val Pro Leu Ser Arg Leu Ala Asp Gly Lys Ile Glu Ser Ala
            340                 345                 350
Ala Ala Val Leu Leu His Ser Leu Ala Tyr Leu Pro Arg Ala Ala Gln
        355                 360                 365
Arg Arg Leu Arg Pro Tyr Gln Leu Leu Leu Cys Leu Gly Ser Ala Asp
370                 375                 380
Arg Ala Val Asp Ser Ala Leu Ala Ala Asp Leu Gly Leu Arg Leu Val
385                 390                 395                 400
His Val Asp Thr Ser Arg Ala Glu Glu Ile Ala Asp Thr Val Met Ala
                405                 410                 415
Leu Phe Leu Gly Leu Leu Arg Arg Thr His Leu Leu Ser Arg His Ala
            420                 425                 430
Leu Ser Ala Ser Gly Trp Leu Gly Ser Val Gln Pro Leu Cys Arg Gly
        435                 440                 445
Met Arg Arg Cys Arg Gly Leu Val Leu Gly Ile Gly Arg Ser Ala
450                 455                 460
Ser Ala Arg Ser Leu Ala Thr Arg Ser Leu Ala Phe Lys Met Ser Val
```

```
              465                 470                 475                 480
        Leu Tyr Phe Asp Ile His Glu Gly Lys Gly Lys Val Ser Arg Ser Ser
                            485                 490                 495
        Leu Arg Phe Pro Pro Ala Ala Arg Arg Met Asp Thr Leu Asn Asp Leu
                        500                 505                 510
        Leu Ala Ala Ser Asp Leu Ile Ser Leu His Cys Ala Leu Ser Asn Glu
                        515                 520                 525
        Thr Val Gln Ile Leu Asn Ala Glu Cys Leu Gln His Ile Lys Pro Gly
                    530                 535                 540
        Ala Phe Leu Val Asn Thr Gly Ser Ser Gln Leu Leu Asp Asp Cys Ser
        545                 550                 555                 560
        Leu Lys Gln Leu Leu Ile Asp Gly Thr Leu Ala Gly Cys Ala Leu Asp
                        565                 570                 575
        Gly Ala Glu Gly Pro Gln Trp Met Glu Ala Trp Val Lys Glu Met Pro
                    580                 585                 590
        Asn Val Leu Ile Leu Pro Arg Ser Ala Asp Tyr Ser Glu Glu Val Trp
                    595                 600                 605
        Val Glu Ile Arg Asp Lys Ala Ile Ser Leu Leu Gln Ser Phe Phe Phe
                610                 615                 620
        Asp Gly Val Ile Pro Lys Asp Ile Ile Ser Asp Glu Glu Glu Glu Ser
        625                 630                 635                 640
        Glu Met Gly Asp Glu Asn Glu Gln Phe His Lys Gln Asp Lys Glu Ser
                            645                 650                 655
        Phe Leu Gln Ala Ser Ile Gly Glu Arg Leu Thr Asp Asp Ile Gln Val
                        660                 665                 670
        Ser Pro Glu Ser Thr Arg Ser Lys Val Ile Asn Gln Ser Thr Glu Ser
                    675                 680                 685
        Ser Gln Ala Gln Gly Ser Gly Leu Ser Gln Thr Thr Ala Ala Arg Ser
                690                 695                 700
        Glu Gly Lys Arg Ser Arg Ser Gly Lys Lys Ala Lys Lys Arg His Gly
        705                 710                 715                 720
        Arg Gln Lys Ser Ile Gln Lys Pro Asp Asp Leu Ser His Leu Glu Lys
                        725                 730                 735
        Glu Ser Thr Ser His Arg Glu Asp Asp Ala Thr Met Ser Gly Thr Asp
                        740                 745                 750
        Gln Val Leu Ser Ser Ser Arg Phe Ala Ser Pro Glu Asp Ser Arg
                    755                 760                 765
        Ser Arg Lys Thr Pro Ile Glu Ser Ile Gln Glu Ser Asn Ala Asp Gln
            770                 775                 780
        Leu Leu Arg Ser Ser Lys Lys Leu Ser Gly Lys Ser Gly Glu Leu Leu
        785                 790                 795                 800
        Lys Asp Gly Tyr Val Ile Ala Leu Tyr Ala Arg Asp Arg Pro Ala Leu
                            805                 810                 815
        His Val Ser Arg Gln Arg Val Lys Gly Gly Trp Phe Leu Asp Ala
                        820                 825                 830
        Met Ser Asn Val Thr Lys Arg Asp Pro Ala Ser Gln Phe Leu Val Val
                    835                 840                 845
        Phe Arg Ser Lys Asp Thr Ile Gly Leu Arg Ser Phe Ala Ala Gly Gly
                        850                 855                 860
        Lys Leu Leu Gln Ile Asn Arg Arg Thr Glu Phe Val Phe Ala Ser His
        865                 870                 875                 880
        Ser Phe Asp Val Trp Glu Ser Trp Met Leu Glu Gly Ser Leu Glu Asp
                            885                 890                 895
```

```
Cys Arg Leu Val Asn Cys Arg Asn Pro Leu Ala Val Leu Asp Val Arg
                900                 905                 910

Ile Glu Val Leu Ala Ala Val Gly Glu Asp Asp Gly Val Thr Arg Trp
        915                 920                 925

Leu Asp
    930

<210> SEQ ID NO 8
<211> LENGTH: 629
<212> TYPE: PRT
<213> ORGANISM: Manihot esculenta

<400> SEQUENCE: 8

Met Val Met Ser Ala Thr Ser Ile Arg Ser Ser Val Thr Met Ser His
1               5                   10                  15

Arg Thr Ser Pro Ala Gln Ala Leu Pro Leu Val Val Thr Leu Asn Cys
            20                  25                  30

Ile Glu Asp Cys Ala Ile Glu Gln Asp Ser Leu Ala Gly Val Ala Ser
        35                  40                  45

Ile Glu His Val Pro Leu Ser Arg Leu Ala Asp Gly Lys Ile Glu Ser
    50                  55                  60

Ala Ala Ala Val Leu Leu His Ser Leu Ala Tyr Leu Pro Arg Ala Ala
65                  70                  75                  80

Gln Arg Arg Leu Arg Pro Asn Gln Leu Ile Leu Cys Leu Gly Ser Ala
                85                  90                  95

Asp Arg Ala Val Asp Ser Ala Leu Ala Ala Asp Leu Gly Leu Arg Leu
            100                 105                 110

Val His Val Asp Thr Ser Arg Ala Glu Glu Ile Ala Asp Thr Val Met
    115                 120                 125

Ala Leu Phe Leu Gly Leu Leu Arg Arg Thr His Leu Leu Ser Arg His
130                 135                 140

Ala Leu Ser Ala Ser Gly Trp Leu Gly Ser Val Gln Pro Leu Cys Arg
145                 150                 155                 160

Gly Met Arg Arg Cys Arg Gly Leu Val Leu Gly Ile Val Gly Arg Ser
                165                 170                 175

Ala Ser Ala Arg Ser Leu Ala Thr Arg Ser Leu Ala Phe Lys Ile Ser
            180                 185                 190

Val Leu Tyr Phe Asp Val His Glu Gly Lys Gly Lys Val Ser Arg Ser
    195                 200                 205

Ser Ile Arg Phe Pro Pro Ala Ala Arg Arg Met Asp Thr Leu Asn Asp
    210                 215                 220

Leu Leu Ala Ala Ser Asp Leu Ile Ser Leu His Cys Ala Leu Thr Asn
225                 230                 235                 240

Glu Thr Val Gln Ile Ile Asn Ala Glu Cys Leu Gln His Ile Lys Pro
                245                 250                 255

Gly Ala Phe Leu Val Asn Thr Gly Ser Ser Gln Leu Leu Asp Asp Cys
            260                 265                 270

Ala Leu Lys Gln Leu Leu Ile Asp Gly Thr Leu Ala Gly Cys Ala Leu
    275                 280                 285

Asp Gly Ala Glu Gly Pro Gln Trp Met Glu Ala Trp Val Lys Glu Met
290                 295                 300

Pro Asn Val Leu Ile Leu Pro Arg Ser Ala Asp Tyr Ser Glu Glu Val
305                 310                 315                 320

Trp Met Glu Ile Arg Glu Lys Ala Ile Ser Leu Leu Gln Ser Phe Phe
```

```
            325                 330                 335
Phe Asp Gly Val Ile Pro Lys Asp Ala Ile Ser Asp Glu Glu Glu
                340                 345                 350
Ser Glu Leu Ala Asp Glu Ser Glu Glu Phe Leu Lys Gln Asp Asn Ala
            355                 360                 365
Ser Ala Leu Gln Ala Ser Val Gly Glu Lys Leu Lys Asp Ile Leu
        370                 375                 380
Leu Ser Pro Glu Ser Ser Asn Arg Lys Gly Asn Asn Gln Ser Thr Glu
385                 390                 395                 400
Ser Ser Tyr Pro Ala Lys Ser Ser Gly Leu Ser Gln Thr Ala Val Arg
            405                 410                 415
Ser Glu Gly Arg Ser Ser Arg Ser Gly Lys Lys Ala Lys Lys Arg His
            420                 425                 430
Gly Arg Gln Lys Ser Leu Gln Lys Ser Asp Asp Pro Arg Gln Leu Glu
            435                 440                 445
Asn Glu Ser Asn Ser Asn Arg Glu Asp Asp Thr Ala Met Ser Gly Thr
    450                 455                 460
Asp Gln Val Leu Ser Ser Gly Ser Arg Phe Gly Ser Pro Glu Asp Ser
465                 470                 475                 480
Ser Ser Arg Lys Thr Pro Ile Ala Ser Met Gln Ser Thr Ser Asp
                485                 490                 495
Gln Leu Leu Ser Ser Lys Asn Leu Ser Arg Lys Ser Gly Glu Leu
            500                 505                 510
Leu Lys Asp Gly Cys Val Ile Ala Leu Tyr Ala Arg Asp Gln Pro Ala
        515                 520                 525
Leu His Val Ser Arg Gln Arg Val Lys Gly Gly Trp Phe Leu Asp
    530                 535                 540
Ala Met Ser Asn Val Thr Lys Arg Asp Pro Ala Ala Gln Phe Leu Val
545                 550                 555                 560
Val Phe Arg Ser Lys Asp Thr Val Gly Leu Arg Ser Phe Ala Ala Gly
                565                 570                 575
Gly Lys Leu Leu Gln Ile Asn Arg Arg Met Glu Phe Val Phe Ala Ser
            580                 585                 590
His Ser Phe Asp Val Trp Glu Ser Trp Met Leu Glu Gly Ser Leu Glu
        595                 600                 605
Glu Cys Arg Leu Val Asn Cys Arg Asn Pro Leu Asn Ser Ile Glu Leu
    610                 615                 620
Trp Ile Glu Phe Ser
625

<210> SEQ ID NO 9
<211> LENGTH: 628
<212> TYPE: PRT
<213> ORGANISM: Linum usitatissimum

<400> SEQUENCE: 9

Met Ser His Arg Asn Asn Asn Pro Ala Pro Pro Leu Pro Leu Val
1               5                   10                  15

Val Thr Leu Asn Cys Val Asp Asp Cys Gly Val Glu Gln Glu Ser Leu
                20                  25                  30

Ser Gly Val Ala Ala Val Glu His Val Pro Leu Ser Arg Leu Ala Asp
            35                  40                  45

Gly Lys Ile Glu Ser Ala Ser Ala Val Leu Leu His Ser Leu Ala Tyr
        50                  55                  60
```

-continued

```
Leu Pro Arg Ala Ala Gln Arg Arg Leu Arg Pro Tyr Gln Leu Ile Leu
 65                  70                  75                  80

Cys Leu Gly Ser Ala Asp Arg Ala Val Asp Ser Ala Leu Ala Ala Asp
                 85                  90                  95

Leu Gly Leu Arg Leu Val His Val Asp Thr Ser Arg Ala Glu Glu Ile
            100                 105                 110

Ala Asp Thr Val Met Ala Leu Phe Leu Gly Leu Val Arg Arg Thr His
        115                 120                 125

Leu Leu Ser Arg His Ala Leu Ser Ala Ser Gly Trp Leu Gly Ser Val
    130                 135                 140

Gln Pro Leu Cys Arg Gly Met Arg Arg Cys Arg Gly Met Val Leu Gly
145                 150                 155                 160

Ile Val Gly Arg Ser Ala Ser Ala Arg Ala Leu Ala Ser Arg Ser Leu
                165                 170                 175

Ala Phe Lys Met Ser Val Leu Tyr Phe Asp Val Tyr Gln Gly Asn Gly
            180                 185                 190

Gln Val Ser Arg Ser Ser Ile Thr Phe Pro Ser Ala Ala Arg Arg Met
        195                 200                 205

Asp Thr Leu Asn Asp Leu Leu Ala Ala Ser Asp Leu Ile Ser Leu His
    210                 215                 220

Cys Ala Leu Thr Asn Asp Thr Val Gln Ile Leu Ser Ala Glu Cys Leu
225                 230                 235                 240

Gln His Val Lys Pro Gly Ala Phe Leu Val Asn Thr Gly Ser Cys Gln
                245                 250                 255

Leu Leu Asp Asp Cys Ala Leu Lys Gln Leu Leu Ile Asp Gly Thr Leu
            260                 265                 270

Ala Gly Cys Ala Leu Asp Gly Ala Glu Gly Pro Gln Trp Met Glu Ala
        275                 280                 285

Trp Val Lys Glu Met Pro Asn Val Leu Ile Leu Pro Arg Ser Ala Asp
    290                 295                 300

Tyr Ser Glu Glu Val Trp Met Glu Ile Arg Glu Lys Ala Ile Ser Ile
305                 310                 315                 320

Leu Gln Ser Phe Phe Phe Asp Gly Val Ile Pro Lys Asp Ala Ile Ser
                325                 330                 335

Asp Ala Glu Glu Asp Val Asp Glu Leu Gly Asp Glu Thr Glu Pro Phe
            340                 345                 350

His Lys Lys Asp Lys Glu Ser Glu His Met Thr Asp Asp Phe Lys
        355                 360                 365

Leu Ser Pro Glu Ser Ser Asn Arg Arg Ala Ile Glu Gln Leu Thr Glu
    370                 375                 380

Ser Pro Gly Gln Ala Gln Val Ser Ser Leu Ser Gln Asn Thr Thr Pro
385                 390                 395                 400

Lys Ser Asp Gly Arg Arg Ser Arg Ser Gly Lys Lys Ala Lys Lys Arg
                405                 410                 415

His Gly Arg Gln Lys Ala Met Ser Lys Ser Asn Asp Pro Ser Gln Leu
            420                 425                 430

Glu Lys Glu Ser Thr Ser His Gln Glu Asp Asp Thr Ala Leu Ser Gly
        435                 440                 445

Thr Asp Gln Val Leu Ser Ser Gly Ser Arg Phe Ala Ser Pro Glu Pro
    450                 455                 460

Ser Arg Ser Arg Lys Thr Pro Ile Glu Ala Met Gln Glu Ser Pro Ser
465                 470                 475                 480

Asp Gln Phe Lys Ser Ser Ser Lys His Phe Ser Gly Lys Pro Ser Glu
```

```
                        485                 490                 495
Leu Leu Lys Asp Gly Cys Val Ile Ala Leu Tyr Ala Arg Asp Arg His
            500                 505                 510

Ala Leu His Val Ser Arg Gln Arg Val Lys Gly Gly Gly Trp Phe Leu
            515                 520                 525

Asp Ala Met Ser Ser Val Thr Lys Arg Asp Pro Ala Ala Gln Phe Leu
            530                 535                 540

Val Val Tyr Arg Asn Lys Glu Thr Met Gly Leu Arg Ser Phe Ala Ala
545                 550                 555                 560

Gly Gly Lys Leu Leu Gln Ile Asn Arg Met Glu Phe Val Phe Ala
            565                 570                 575

Ser His Ser Phe Asp Val Trp Glu Ser Trp Met Leu Glu Gly Pro Leu
            580                 585                 590

Glu Glu Cys Arg Leu Val Asn Cys Arg Asn Pro Leu Ala Val Leu Asp
            595                 600                 605

Val Cys Ile Glu Ile Leu Ala Ala Val Gly Glu Asp Gly Val Thr
            610                 615                 620

Arg Trp Leu Asp
625

<210> SEQ ID NO 10
<211> LENGTH: 630
<212> TYPE: PRT
<213> ORGANISM: Linum usitatissimum

<400> SEQUENCE: 10

Met Ser His Arg Asn Asn Asn Pro Ala Pro Pro Leu Pro Leu Val
1               5                   10                  15

Val Thr Leu Asn Cys Val Asp Asp Cys Gly Ile Glu Gln Glu Ser Leu
            20                  25                  30

Ser Gly Val Ala Ala Val Glu His Val Pro Leu Ser Arg Leu Ala Asp
            35                  40                  45

Gly Lys Ile Glu Ser Ala Ser Ala Val Leu Leu His Ser Leu Ala Tyr
        50                  55                  60

Leu Pro Arg Ala Ala Gln Arg Arg Leu Arg Pro Tyr Gln Leu Ile Leu
65                  70                  75                  80

Cys Leu Gly Ser Ala Asp Arg Ala Val Asp Ser Ala Leu Ala Ala Asp
                85                  90                  95

Leu Gly Leu Arg Leu Val His Val Asp Thr Ser Arg Ala Glu Glu Ile
            100                 105                 110

Ala Asp Thr Val Met Ala Leu Phe Leu Gly Leu Val Arg Arg Thr His
            115                 120                 125

Leu Leu Ser Arg His Ala Leu Ser Ala Ser Gly Trp Leu Gly Ser Val
            130                 135                 140

Gln Pro Leu Cys Arg Gly Met Arg Arg Cys Arg Gly Met Val Leu Gly
145                 150                 155                 160

Ile Val Gly Arg Ser Ala Ser Ala Arg Ala Leu Ala Ser Arg Ser Leu
                165                 170                 175

Ala Phe Lys Met Ser Val Leu Tyr Phe Asp Val Tyr Gln Gly Asn Gly
            180                 185                 190

Met Val Ser Arg Ser Pro Ile Thr Phe Pro Ser Ala Ala Arg Arg Met
            195                 200                 205

Asp Thr Leu Asn Asp Leu Leu Ala Ala Ser Asp Leu Ile Ser Leu His
        210                 215                 220
```

```
Cys Ala Leu Thr Asn Glu Thr Val Gln Ile Leu Ser Ala Arg His Thr
225                 230                 235                 240

His Pro Pro Thr His Thr Arg Ala Phe Leu Val Asn Thr Gly Ser Cys
            245                 250                 255

Gln Leu Leu Asp Asp Cys Ala Leu Lys Gln Leu Leu Ile Asp Gly Thr
                260                 265                 270

Leu Ala Gly Cys Ala Leu Asp Gly Ala Glu Gly Pro Gln Trp Met Glu
            275                 280                 285

Ala Trp Val Lys Glu Leu Pro Asn Val Leu Ile Leu Pro Arg Ser Ala
        290                 295                 300

Asp Tyr Ser Glu Glu Val Trp Met Glu Ile Arg Glu Lys Ala Ile Ser
305                 310                 315                 320

Ile Leu Gln Ser Phe Phe Phe Asp Gly Val Ile Pro Lys Asp Ile
                325                 330                 335

Ser Asp Ala Glu Glu Asp Val Asp Glu Leu Gly Asp Glu Thr Glu Pro
                340                 345                 350

Phe His Lys Gln Asp Lys Glu Ser Ser Val His Met Thr Asp Gly Phe
            355                 360                 365

Lys Leu Ser Pro Glu Ser Ser Asn Arg Arg Ala Ile Glu Gln Ser Thr
        370                 375                 380

Glu Ser Pro Gly Gln Ala Gln Val Ser Ser Leu Ser Gln Asn Thr Thr
385                 390                 395                 400

Pro Lys Ser Asp Gly Arg Arg Ser Arg Ser Gly Lys Lys Ala Lys Lys
                405                 410                 415

Arg His Gly Arg Gln Lys Ala Met Gln Lys Ser Ser Asp Pro Ser Gln
            420                 425                 430

Leu Glu Lys Glu Ser Thr Ser His Gln Glu Asp Asp Thr Ala Leu Ser
        435                 440                 445

Gly Thr Asp Gln Val Leu Ser Ser Gly Ser Arg Phe Ala Ser Pro Glu
450                 455                 460

Ala Ser Arg Ser Arg Lys Thr Pro Ile Ile Glu Ala Met Gln Glu Ser
465                 470                 475                 480

Pro Ser Asp Gln Phe Leu Ser Ser Ser Lys His Leu Ser Gly Lys Pro
                485                 490                 495

Phe Glu Leu Leu Lys Asp Gly Cys Val Ile Ala Leu Tyr Ala Arg Asp
                500                 505                 510

Arg His Ala Leu His Val Ser Arg Gln Arg Val Lys Gly Gly Gly Trp
            515                 520                 525

Phe Leu Asp Ala Met Ser Ser Val Thr Lys Arg Asp Pro Ala Ala Gln
        530                 535                 540

Phe Leu Val Val Tyr Arg Asn Lys Glu Thr Met Gly Leu Arg Ser Phe
545                 550                 555                 560

Ala Ala Gly Gly Lys Leu Leu Gln Ile Asn Arg Arg Met Glu Phe Val
                565                 570                 575

Phe Ala Ser His Ser Phe Asp Val Trp Glu Ser Trp Met Leu Glu Gly
            580                 585                 590

Pro Leu Glu Glu Cys Arg Leu Val Asn Cys Arg Asn Pro Leu Ala Val
        595                 600                 605

Leu Glu Val Cys Ile Glu Ile Leu Ala Ala Val Gly Glu Asp Asp Gly
            610                 615                 620

Val Thr Arg Trp Leu Asp
625                 630
```

<210> SEQ ID NO 11
<211> LENGTH: 647
<212> TYPE: PRT
<213> ORGANISM: Theobroma cacao

<400> SEQUENCE: 11

```
Met Asn Thr Thr Thr Thr Thr Lys Thr Ser Ser Arg Leu Arg Ser Ser
 1               5                  10                  15

Ala Ala Met Pro His Arg Asn Asn Pro Thr Pro Leu Pro Leu Ala Val
             20                  25                  30

Ser Leu Asn Cys Ile Glu Asp Cys Val Leu Glu Gln Glu Ser Leu Ala
         35                  40                  45

Gly Val Ala Leu Val Glu His Val Pro Leu Ser Arg Leu Gly Glu Gly
     50                  55                  60

Lys Ile Glu Ala Ala Ala Val Leu Leu His Ser Leu Ala Tyr Leu
 65                  70                  75                  80

Pro Arg Ala Ala Gln Arg Arg Leu Cys Pro Tyr Gln Leu Ile Leu Cys
                 85                  90                  95

Leu Gly Ser Ser Asp Arg Ala Val Asp Ser Ala Leu Ala Ala Asp Leu
            100                 105                 110

Gly Leu Arg Leu Val His Val Asp Ala Ser Arg Ala Glu Glu Ile Ala
        115                 120                 125

Asp Thr Val Met Ala Leu Phe Leu Gly Leu Leu Arg Arg Thr His Leu
130                 135                 140

Leu Ser Arg His Ser Leu Ser Ala Ser Gly Trp Leu Gly Ser Val Gln
145                 150                 155                 160

Pro Leu Cys Arg Gly Met Arg Cys Arg Gly Leu Val Leu Gly Ile
                165                 170                 175

Val Gly Arg Ser Ala Ser Ala Arg Ser Leu Ala Ser Arg Ser Leu Ala
            180                 185                 190

Phe Lys Met Ser Val Leu Tyr Phe Asp Val Ile Glu Glu Asn Gly Lys
        195                 200                 205

Val Ser Ser Ser Ser Ile Thr Phe Pro Ser Ala Ala Arg Arg Met Asp
210                 215                 220

Thr Leu Asn Asp Leu Leu Ala Ala Ser Asp Leu Ile Ser Leu His Cys
225                 230                 235                 240

Ala Leu Thr Asn Glu Thr Val Gln Ile Ile Asn Ala Glu Cys Leu Gln
                245                 250                 255

His Val Lys Pro Gly Ala Phe Leu Val Asn Thr Gly Ser Ser Gln Leu
            260                 265                 270

Leu Asp Asp Cys Ala Leu Lys Gln Leu Leu Ile Asp Gly Thr Leu Ala
        275                 280                 285

Gly Cys Ala Leu Asp Gly Ala Glu Gly Pro Gln Trp Met Glu Ala Trp
    290                 295                 300

Val Lys Glu Met Pro Asn Val Leu Ile Leu Pro Arg Ser Ala Asp Tyr
305                 310                 315                 320

Ser Glu Glu Val Trp Met Glu Ile Arg Glu Lys Ala Ile Ser Met Leu
                325                 330                 335

Gln Thr Tyr Phe Phe Asp Gly Val Ile Pro Lys Asp Ala Ile Ser Asp
            340                 345                 350

Gly Asp Glu Glu Glu Ser Glu Ile Val Asp Glu Arg Gly Gln Phe Ser
        355                 360                 365

Arg Gln Asp Lys Glu Ser Ala Leu Gln Gly Ser Thr Glu Gln Leu
370                 375                 380
```

```
Thr Asp Asp Ile Gln Pro Ser Pro Glu Ser Ser Leu Lys Lys Asp Thr
385                 390                 395                 400

Asn Gln Ser Lys Glu Tyr Pro Asn Gln Asn Gly Ser Gly Leu Ser
            405                 410                 415

His Asn Thr Ala Thr Lys Ser Asp Thr Arg Arg Gly Arg Ser Gly Lys
                420                 425                 430

Lys Ala Lys Arg His Ala Arg Gln Lys Thr Leu Gln Lys Pro Asp
            435                 440                 445

Glu Pro Leu Ile Leu Glu Lys Glu Ser Thr Ser Gln Arg Glu Asp Asp
            450                 455                 460

Thr Ala Met Ser Gly Thr Asp Gln Ala Leu Ser Ser Gly Ser Arg Ser
465                 470                 475                 480

Pro Glu Asp Ser Arg Ser Arg Lys Thr Pro Ile Glu Leu Met Gln Gly
                485                 490                 495

Ser Thr Ser Asp Gln Leu Leu Lys Ala Ser Lys Lys Val Ser Gly Leu
                500                 505                 510

Ser Ala Asp Thr Leu Lys Asp Gly Tyr Val Ile Ala Leu Tyr Ala Arg
                515                 520                 525

Asp Arg Thr Ala Leu His Val Ser Arg Gln Val Lys Gly Gly Gly
            530                 535                 540

Trp Phe Leu Asp Thr Met Ser Asn Val Thr Lys Arg Asp Pro Ala Ala
545                 550                 555                 560

Gln Phe Leu Val Val Tyr Arg Ser Lys Asp Thr Ile Gly Leu Arg Ser
                565                 570                 575

Phe Ala Ala Gly Gly Lys Leu Leu Gln Ile Asn Arg Arg Met Glu Phe
                580                 585                 590

Val Phe Ala Ser His Ser Phe Asp Val Trp Glu Ser Trp Thr Leu Gln
                595                 600                 605

Gly Pro Leu Glu Glu Cys Arg Leu Val Asn Cys Arg Asn Pro Ser Ala
            610                 615                 620

Ile Leu Asp Val His Val Glu Ile Leu Ala Ala Val Gly Glu Asp Asp
625                 630                 635                 640

Gly Val Thr Arg Trp Leu Asp
            645

<210> SEQ ID NO 12
<211> LENGTH: 647
<212> TYPE: PRT
<213> ORGANISM: Gossypium raimondii

<400> SEQUENCE: 12

Met Asn Leu Ala Ser Asn Ser Thr Thr Ser Pro Met Leu Arg Ser Ser
1               5                   10                  15

Ser Gly Met Arg His Arg Asp Asn Pro Thr Pro Leu Pro Leu Val Ile
            20                  25                  30

Ser Leu Asn Cys Ile Glu Asp Cys Ala Leu Glu Gln Glu Phe Leu Ala
            35                  40                  45

Gly Val Ala Val Val His His Val Pro Leu Ser Ser Leu Gly Glu Gly
        50                  55                  60

Lys Ile Glu Gly Ala Ala Ala Val Leu Leu His Ser Leu Ser Tyr Leu
65                  70                  75                  80

Pro Arg Ala Ala Gln Arg Arg Leu Arg Pro Tyr Gln Leu Ile Leu Cys
                85                  90                  95

Leu Gly Ser Ser Asp Arg Ala Val Asp Ser Ala Leu Ala Ala Asp Leu
                100                 105                 110
```

```
Gly Leu Arg Leu Val His Val Asp Ala Ser Arg Ala Glu Glu Ile Ala
            115                 120                 125

Asp Thr Val Met Ala Leu Phe Leu Gly Leu Leu Arg Arg Thr His Leu
130                 135                 140

Leu Ser Arg His Ala Leu Ser Ala Ser Gly Trp Leu Gly Ser Val Gln
145                 150                 155                 160

Pro Leu Cys Arg Gly Met Arg Arg Cys Arg Gly Leu Val Leu Gly Ile
                165                 170                 175

Val Gly Arg Ser Ala Ser Ala Arg Ser Leu Ala Ser Arg Ser Leu Ala
                180                 185                 190

Phe Lys Met Ser Val Leu Tyr Tyr Asp Ile Val Glu Glu Asn Gly Lys
                195                 200                 205

Val Ser Arg Ser Ser Ile Thr Phe Pro Pro Ala Arg Arg Met Asp
210                 215                 220

Thr Leu Asn Asp Leu Leu Ala Ala Ser Asp Leu Ile Ser Leu His Cys
225                 230                 235                 240

Ala Leu Thr Asp Glu Thr Ile Gln Ile Ile Asn Ala Glu Cys Leu Gln
                245                 250                 255

His Ile Lys Pro Gly Ala Phe Leu Val Asn Thr Gly Ser Ser Gln Leu
                260                 265                 270

Leu Asp Asp Cys Ala Leu Lys Gln Leu Leu Ile Asp Gly Thr Leu Ala
                275                 280                 285

Gly Cys Ala Leu Asp Gly Ala Glu Gly Pro Gln Trp Met Glu Ala Trp
                290                 295                 300

Val Lys Glu Met Pro Asn Val Leu Ile Leu Pro Arg Ser Ala Asp Tyr
305                 310                 315                 320

Ser Glu Glu Val Trp Met Glu Ile Arg Glu Lys Ala Ile Ser Met Leu
                325                 330                 335

Gln Thr Phe Phe Cys Asp Gly Val Ile Pro Lys Asp Ala Thr Ser Asp
                340                 345                 350

Glu Asp Glu Glu Ser Glu Ile Val Asp Glu Lys Glu Gln Phe Ser
                355                 360                 365

Ile Gln Glu Lys Glu Ser Ala Leu Arg Gly Ser Ser Gly Glu Gln Phe
370                 375                 380

Thr Asp Asp Ile Gln Leu Ser Pro Glu Ser Ser Leu Lys Lys Asp Thr
385                 390                 395                 400

Asn Gln Ala Lys Asp Tyr Pro Asn Gln Asn Gln His Ser Gly Met Ser
                405                 410                 415

Ser Gly Thr Pro Thr Lys Ser Asp Ala Lys Arg Ser Arg Ser Gly Lys
                420                 425                 430

Lys Ala Lys Lys Arg His Ala Arg Arg Asn Asn Leu Gln Lys Ser Asp
                435                 440                 445

Glu Pro Leu Ile Leu Glu Lys Glu Ser Thr Ser Gln Arg Glu Asp Asp
450                 455                 460

Thr Ala Met Ser Gly Thr Asp Gln Ala Leu Ser Ser Gly Ser Arg Ser
465                 470                 475                 480

Pro Leu Asp Ser Arg Ser Arg Lys Thr Pro Lys Glu Leu Thr Gln Gly
                485                 490                 495

Ser Thr Ser Asp Gln Leu Leu Lys Met Ser Arg Asn Leu Ser Gly Gln
                500                 505                 510

Ser Gly Asp Leu Leu Lys Glu Gly Tyr Val Ile Ala Met Tyr Ala Arg
                515                 520                 525
```

-continued

Asp Arg Pro Ala Leu His Leu Ser Arg Gln Arg Val Lys Gly Gly Gly
    530                 535                 540

Trp Phe Leu Asp Ser Met Ser Asn Val Thr Lys Arg Asp Pro Ala Ala
545                 550                 555                 560

Gln Phe Leu Val Val Cys Arg Ser Lys Asp Thr Ile Gly Leu Arg Ser
                565                 570                 575

Phe Ala Ala Gly Gly Lys Leu Leu Gln Ile Asn Arg Arg Met Glu Phe
            580                 585                 590

Val Phe Ala Ser His Ser Phe Asp Ile Trp Glu Ser Trp Thr Leu Gln
        595                 600                 605

Gly Pro Leu Glu Glu Cys Arg Leu Val Asn Cys Arg Asn Pro Ser Ala
    610                 615                 620

Ile Leu Asp Val Arg Ile Glu Ile Leu Ala Ala Val Gly Glu Asp Asp
625                 630                 635                 640

Gly Val Thr Arg Trp Leu Asp
                645

<210> SEQ ID NO 13
<211> LENGTH: 645
<212> TYPE: PRT
<213> ORGANISM: Gossypium raimondii

<400> SEQUENCE: 13

Met Asn Thr Ser Ile Pro Thr Thr Ser Ser Gly Leu Arg Ser Ser Ala
1               5                   10                  15

Thr Met Pro Arg Arg Asn Ile Pro Thr Pro Leu Pro Leu Val Val Ser
            20                  25                  30

Leu Asn Cys Val Glu Asp Cys Val Leu Glu Gln Glu Ser Leu Ala Gly
        35                  40                  45

Val Ser Leu Phe Glu His Val Pro Leu Ser Arg Leu Ala Asp Gly Lys
    50                  55                  60

Ile Glu Ala Ala Ala Ala Val Leu Leu His Ser Leu Ala Tyr Leu Pro
65                  70                  75                  80

Arg Ala Ala Gln Arg Arg Leu Arg Pro Tyr Gln Leu Ile Leu Cys Leu
                85                  90                  95

Gly Ser Ser Asp Arg Ala Val Asp Ser Ala Leu Ala Ala Asp Leu Gly
            100                 105                 110

Leu Arg Leu Val His Val Asp Val Ser Arg Ala Glu Glu Ile Ala Asp
        115                 120                 125

Thr Val Met Ala Leu Phe Leu Gly Leu Leu Arg Thr His Leu Leu
    130                 135                 140

Ser Arg His Ala Leu Ser Ala Ser Gly Trp Leu Gly Ser Val Gln Pro
145                 150                 155                 160

Leu Cys Arg Gly Met Arg Arg Cys Arg Gly Leu Val Leu Gly Ile Val
                165                 170                 175

Gly Arg Ser Ala Ser Ala Arg Ser Leu Ala Ser Arg Ser Leu Ala Phe
            180                 185                 190

Arg Met Ser Val Leu Tyr Phe Asp Val Val Glu Glu Asn Gly Lys Val
        195                 200                 205

Ser Arg Ser Ser Ile Arg Phe Pro Pro Ala Ala Arg Arg Met Asp Thr
    210                 215                 220

Leu Asn Asp Leu Leu Ala Ala Ser Asp Leu Ile Ser Leu His Cys Ala
225                 230                 235                 240

Leu Thr Asn Glu Thr Val Gln Ile Ile Asn Ser Glu Cys Leu Gln His
                245                 250                 255

Val Lys Pro Gly Ala Phe Leu Val Asn Thr Gly Ser Ser Gln Leu Leu
        260                 265                 270

Asp Asp Cys Ala Leu Lys Gln Leu Ile Asp Gly Thr Leu Ala Gly
            275                 280                 285

Cys Ala Leu Asp Gly Ala Glu Gly Pro Gln Trp Met Glu Ala Trp Val
        290                 295                 300

Lys Glu Met Pro Asn Val Leu Ile Leu Pro Arg Ser Ala Asp Tyr Ser
305                 310                 315                 320

Glu Glu Ala Trp Met Glu Ile Arg Glu Lys Ala Ile Ser Met Leu Gln
                325                 330                 335

Ser Phe Phe Phe Asp Gly Val Ile Pro Lys Asp Ala Ile Ser Asp Glu
                340                 345                 350

Asp Glu Glu Glu Ser Glu Ile Val Asp Glu Lys Gly Gln Phe Ser Ile
            355                 360                 365

Gln Asp Lys Glu Ser Ala Leu Gln Gly Ser Cys Ala Glu Gln Leu Ile
        370                 375                 380

Asn Glu Ile Gln Gln Ser Pro Glu Ser Ser Leu Lys Lys Asp Ser Asn
385                 390                 395                 400

Gln Ser Lys Gln Ser Asn Gln Asn Pro Ser Pro Gly Leu Pro His Asn
                405                 410                 415

Ile Ala Ala Lys Ser Glu Gly Arg Arg Ser Arg Ser Gly Lys Lys Ala
                420                 425                 430

Lys Lys Arg Gln Ala Arg Gln Lys Thr Leu Gln Lys Ser Asp Glu Pro
            435                 440                 445

Leu Ile Leu Glu Lys Glu Ser Thr Ser Gln Arg Glu Asp Asp Thr Ala
        450                 455                 460

Met Ser Gly Thr Asp Gln Ala Leu Ser Ser Gly Ser Gln Ser Pro Glu
465                 470                 475                 480

Gly Ser Arg Ser Arg Lys Thr Pro Ile Glu Leu Met Gln Val Ser Thr
                485                 490                 495

Ser Asp Arg Leu Leu Lys Thr Ser Lys Lys Leu Ser Glu Leu Ser Gly
            500                 505                 510

Asp Ser Leu Lys Asp Gly Tyr Ile Ile Ala Leu Tyr Ala Arg Val Cys
        515                 520                 525

Pro Ala Leu His Val Ser Arg Gln Arg Val Lys Gly Gly Gly Trp Phe
        530                 535                 540

Leu Asp Thr Met Ser Asn Val Thr Lys Arg Asp Pro Ala Ala Gln Phe
545                 550                 555                 560

Leu Val Val Tyr Arg Asn Lys Glu Thr Ile Gly Leu Arg Ser Cys Ala
                565                 570                 575

Ala Gly Gly Lys Leu Leu Gln Ile Asn Arg Arg Met Glu Phe Val Phe
            580                 585                 590

Ala Ser His Ser Phe Asp Val Trp Glu Ser Trp Thr Leu Gln Gly Pro
        595                 600                 605

Leu Glu Glu Cys Arg Leu Val Asn Cys Arg Asn Pro Ser Ala Val Leu
        610                 615                 620

Asp Val Arg Ile Glu Ile Leu Ala Ala Ile Gly Glu Asp Gly Val
625                 630                 635                 640

Thr Arg Trp Leu Asp
                645

<210> SEQ ID NO 14
<211> LENGTH: 628

<212> TYPE: PRT
<213> ORGANISM: Carica papaya

<400> SEQUENCE: 14

Met Pro His Arg Asn Thr Pro Ala Pro Ala Leu Pro Ser Val Val Thr
1               5                   10                  15

Leu Asn Cys Ile Asp Asp Cys Ala Leu Glu Gln Asp Ser Leu Gly Gly
            20                  25                  30

Val Ala Ser Ile Glu His Val Pro Leu Ser Arg Leu Ala Asp Gly Lys
        35                  40                  45

Ile Glu Ala Ala Ser Ala Val Leu Leu His Ser Leu Ala Phe Leu Pro
50                  55                  60

Arg Ala Ala Gln Arg Arg Leu His Pro Tyr Gln Leu Ile Leu Cys Leu
65                  70                  75                  80

Gly Ser Ala Asp Arg Ala Val Asp Ser Ala Leu Ala Ala Asp Leu Gly
                85                  90                  95

Leu Gln Leu Val His Ile Asp Thr Ser Arg Ala Glu Glu Ile Ala Asp
            100                 105                 110

Thr Val Met Ala Leu Ile Leu Gly Leu Leu Arg Arg Thr His Leu Leu
        115                 120                 125

Ser Arg His Ala Leu Ser Ala Ser Gly Trp Leu Gly Ser Val Gln Pro
130                 135                 140

Leu Cys Arg Gly Met Arg Arg Cys Arg Gly Leu Val Leu Gly Ile Val
145                 150                 155                 160

Gly Arg Ser Ala Ser Ala Arg Ser Leu Ala Ser Arg Ser Leu Ala Phe
                165                 170                 175

Lys Met Ser Val Leu Tyr Phe Asp Val Gln Glu Gly Ser Gly Lys Val
            180                 185                 190

Ser Arg Ser Pro Ile Ile Phe Pro Ser Ala Ala Arg Arg Met Asp Thr
        195                 200                 205

Leu Asn Asp Leu Leu Ala Ala Ser Asp Leu Val Ser Leu His Cys Ala
210                 215                 220

Leu Thr Asn Glu Thr Val Gln Ile Ile Asn Ala Asp Cys Leu Gln His
225                 230                 235                 240

Ile Lys Pro Gly Ala Phe Leu Val Asn Thr Gly Ser Ser Gln Leu Leu
                245                 250                 255

Asp Asp Cys Ala Val Lys Gln Leu Leu Ile Asp Gly Thr Leu Ala Gly
            260                 265                 270

Cys Ala Leu Asp Gly Ala Glu Gly Pro Gln Trp Met Glu Ala Trp Val
        275                 280                 285

Arg Glu Met Pro Asn Val Leu Ile Leu Pro Arg Ser Ala Asp Tyr Ser
290                 295                 300

Glu Glu Val Trp Met Glu Ile Arg Glu Lys Ala Ile Ser Ile Leu Gln
305                 310                 315                 320

Ser Phe Phe Leu Asp Gly Ile Ile Pro Lys Asn Thr Val Ser Asp Glu
                325                 330                 335

Glu Glu Thr Glu Val Gly Asp Glu Asn Asp Gln Phe Asp Lys Gln Asp
            340                 345                 350

Arg Gly Cys Ile Pro Gln Val Ser Met Ser Ala His Leu Thr Asn Asp
        355                 360                 365

Ile Gln Val Ser Pro Glu Ser Ser Gln Lys Lys Gly Thr Ile Gln Ser
370                 375                 380

Lys Glu Ser Pro Ser Gln His Gln Gly Ser Val Leu Ser Gln Ser Thr
385                 390                 395                 400

Gly Thr Lys Ser Asp Gly Arg Ser Arg Ser Gly Lys Lys Ala Lys
                405                 410                 415

Arg Arg His Ala Arg Gln Lys Ser Gln Gln Lys Ser Asp Val Leu
            420                 425                 430

Glu Lys Glu Ser Thr Ser Gln Arg Glu Asp Asp Thr Ala Met Ser Gly
        435                 440                 445

Thr Asp Gln Ala Leu Thr Ser Ser Ser Arg Cys Ala Ser Pro Glu Asp
450                 455                 460

Ser Arg Ser Arg Lys Thr Pro Ile Glu Val Thr Arg Glu Ser Thr Ser
465                 470                 475                 480

Asp Gln Leu Leu Lys Val Ser Lys Lys Leu Gly Gly Lys Ser Ile Glu
                485                 490                 495

Leu Pro Lys Asp Gly Tyr Val Ile Ala Leu Tyr Ala Arg Asp Asn Ser
                500                 505                 510

Ala Leu His Val Ser Arg Gln Arg Val Lys Gly Gly Trp Phe Leu
            515                 520                 525

Asp Thr Met Ser Asn Val Thr Lys Arg Asp Pro Ala Ala Gln Phe Leu
            530                 535                 540

Val Val Tyr Arg Asn Lys Glu Thr Ile Gly Leu Arg Ser Phe Ala Ala
545                 550                 555                 560

Gly Gly Lys Leu Leu Gln Ile Asn Arg Arg Met Glu Phe Val Phe Ala
                565                 570                 575

Ser His Ser Phe Asp Val Trp Glu Ser Trp Thr Leu Glu Gly Ser Leu
            580                 585                 590

Glu Glu Cys Arg Leu Val Asn Cys Arg Asn Pro Leu Ala Val Leu Asn
            595                 600                 605

Val Ser Ile Glu Ile Leu Ala Val Thr Gly Glu Asp Asp Gly Val Met
610                 615                 620

Arg Trp Leu Glu
625

<210> SEQ ID NO 15
<211> LENGTH: 952
<212> TYPE: PRT
<213> ORGANISM: Vitis vinifera

<400> SEQUENCE: 15

Met Asp Tyr Glu Glu Gly Asn Ser Ser Ile Ala Ser Ala Lys Ser Pro
1               5                   10                  15

Asn Ser Arg Ser Asn Leu Tyr Arg Ile Ile Asp Gly His Ser Ser Pro
            20                  25                  30

Pro Ser Val Ser Leu Glu Ile Arg Leu Phe Tyr Val Arg Ile Ala Pro
        35                  40                  45

Cys Val Ile Asp Ser Val Pro Asp His Leu Thr Leu Cys His Ile Arg
    50                  55                  60

Arg Gly Ile Gly Val Ser Leu Glu Ile Asn Gly Ala Arg Ile Pro Ala
65                  70                  75                  80

Ser Glu Thr Ala Ser Leu Thr Leu Arg Arg Asp Arg Leu Asp Lys Glu
                85                  90                  95

Ser Ser Glu Val Ile Tyr Val Ser Thr Asp Ser Val Arg Val Ala Gly
            100                 105                 110

Gly Val Glu Phe Glu Val Tyr Glu Lys Glu Glu Met Ile Leu Cys Gly
        115                 120                 125

Ser Leu Glu Arg Met Glu Ser Ser Trp Gly Asn Gly Ser Gly Gly Leu

-continued

```
                130             135             140
Glu Asn Gly Ser Arg Thr Gly Trp Asp Met Asp Cys Tyr Thr Ala Ala
145                 150                 155                 160
Ser Val Val Ala Gly Ser Ser Ala Phe Phe Gln Pro Lys Leu Gly Val
                165                 170                 175
Ser Ser Pro Ser Ile Glu Val Tyr Ile Ala Gly Cys Ser Ser Ser Met
            180                 185                 190
Pro Val Ile Leu Thr Lys Thr Ile Gln Ile Ser Pro Arg Gln Lys Ala
                195                 200                 205
Ser Arg His Gly Met Leu Asp Ala Ile Pro Glu Gly Glu Ile Gly
210                 215                 220
Lys Ala Gln Glu Asn Ser Asn Gly Thr Val Arg Gln Arg Lys Asp Met
225                 230                 235                 240
Val Met Glu Phe Cys His Asp Asp Tyr Glu Ser Asp Gly Lys Ile Gly
                245                 250                 255
His Gly Phe His Ser Glu Asp Met Tyr Ser Gly Glu Asp Gly Gln Leu
            260                 265                 270
Thr Trp Phe Asn Ala Gly Val Arg Val Gly Val Gly Ile Gly Leu Gly
                275                 280                 285
Met Cys Leu Gly Ile Gly Ile Gly Val Gly Leu Leu Met Arg Ser Tyr
            290                 295                 300
Gln Ala Thr Thr Arg Asn Phe Arg Arg Arg Asp Ser Gly Arg Ser Ser
305                 310                 315                 320
Ala Ser Ala Ala His His His Arg Ser Ala Pro Leu Pro Leu Val Val
                325                 330                 335
Ser Leu Asn Cys Ile Asp Asp Pro Ser Leu Glu Gln Glu Ser Leu Ser
            340                 345                 350
Gly Ile Ala Ser Val Glu His Val Ser Leu Ala Arg Leu Ser Asp Gly
                355                 360                 365
Lys Ile Glu Ser Ala Ala Ala Val Leu Ile His Ser Leu Ala Tyr Leu
            370                 375                 380
Pro Arg Ala Ala Gln Arg Arg Leu Arg Pro Trp Gln Leu Leu Leu Cys
385                 390                 395                 400
Leu Gly Ser Ser Asp Arg Ser Val Asp Ser Ala Leu Ala Ala Asp Leu
                405                 410                 415
Gly Leu Arg Leu Val His Val Asp Thr Ser Arg Ala Glu Glu Val Ala
            420                 425                 430
Asp Thr Val Met Ala Leu Phe Leu Gly Leu Leu Arg Arg Thr His Leu
                435                 440                 445
Leu Ser Arg His Thr Leu Ser Ala Ser Gly Trp Leu Gly Ser Val Gln
450                 455                 460
Pro Leu Cys Arg Gly Met Arg Arg Cys Arg Gly Leu Val Leu Gly Ile
465                 470                 475                 480
Val Gly Arg Ser Ala Ser Ala Arg Ser Leu Ala Thr Arg Ser Leu Ala
                485                 490                 495
Phe Lys Met Asn Val Leu Tyr Phe Asp Val Gln Glu Gly Lys Gly Lys
            500                 505                 510
Leu Ser Arg Ser Ile Thr Phe Pro Pro Ala Ala Arg Arg Met Asp Thr
            515                 520                 525
Leu Asn Asp Leu Leu Ala Ala Ser Asp Leu Val Ser Leu His Cys Thr
            530                 535                 540
Leu Thr Asn Glu Thr Val Gln Ile Ile Asn Ala Glu Cys Leu Gln His
545                 550                 555                 560
```

```
Ile Lys Pro Gly Ala Phe Leu Val Asn Thr Gly Ser Gln Leu Leu
                565                 570                 575

Asp Asp Cys Ala Leu Lys Gln Leu Leu Ile Asp Gly Thr Ile Ala Gly
                580                 585                 590

Cys Ala Leu Asp Gly Ala Glu Gly Pro Gln Trp Met Glu Ala Trp Val
                595                 600                 605

Lys Glu Met Pro Asn Val Leu Ile Leu Pro Arg Ser Ala Asp Tyr Ser
                610                 615                 620

Glu Glu Val Trp Met Glu Ile Arg Glu Lys Thr Ile Cys Ile Leu Gln
625                 630                 635                 640

Thr Tyr Phe Phe Asp Gly Val Ile Pro Lys Asn Thr Val Ser Asp Glu
                645                 650                 655

Glu Asp Glu Glu Ser Glu Ile Val Tyr Glu Asn Glu Gln Phe Asp Lys
                660                 665                 670

Gln Tyr Lys Glu Ile Ala Leu Gln Gly Ser Val Gly Glu Gln Leu Thr
                675                 680                 685

Asp Asp Val Leu Val Ser Pro Glu Ser Ser Gln Lys Lys Gly Thr Asn
                690                 695                 700

Gln Ser Asn Glu Ser Pro Ser Gln His Gln Gly Ser Gly Leu Ser Gln
705                 710                 715                 720

Asn Thr Thr Asn Arg Ser Glu Gly Lys Arg Ser Arg Ser Gly Lys Lys
                725                 730                 735

Ala Lys Lys Arg His Ala Arg Gln Arg Ser Leu Gln Lys Ser Asp Asp
                740                 745                 750

Pro Ser Ala Leu Glu Lys Glu Ser Thr Ser His Arg Glu Asp Asp Thr
                755                 760                 765

Ala Met Ser Gly Thr Asp Gln Val Leu Ser Ser Ser Arg Phe Ala
                770                 775                 780

Ser Pro Glu Asp Ser Arg Ser Arg Lys Thr Pro Ile Glu Ser Val Gln
785                 790                 795                 800

Glu Ser Thr Ser Glu Gln Leu Leu Lys Ser Ser Met Arg Leu Ser Lys
                805                 810                 815

Pro Gly Glu Val Leu Leu Lys Asp Gly Tyr Val Ile Ala Leu His Ala
                820                 825                 830

Arg Asp Arg Ala Ala Leu His Val Ser Arg Gln Arg Val Gln Gly Gly
                835                 840                 845

Gly Trp Phe Leu Asp Thr Met Ser Asn Val Thr Lys Arg Asp Pro Ala
850                 855                 860

Ala Gln Phe Leu Ile Ala Phe Arg Ser Lys Asp Thr Ile Gly Leu Arg
865                 870                 875                 880

Ser Phe Ala Ala Gly Gly Lys Leu Leu Gln Ile Asn Arg Arg Met Glu
                885                 890                 895

Phe Val Phe Ala Ser His Ser Phe Asp Val Trp Glu Ser Trp Met Leu
                900                 905                 910

Glu Gly Ser Leu Glu Glu Cys Arg Leu Val Asn Cys Arg Asn Pro Leu
                915                 920                 925

Ala Val Leu Asp Val Arg Val Glu Ile Leu Ala Ala Val Gly Glu Glu
                930                 935                 940

Asp Gly Val Thr Arg Trp Leu Asp
945                 950

<210> SEQ ID NO 16
<211> LENGTH: 632
```

<212> TYPE: PRT
<213> ORGANISM: Citrus sinensis

<400> SEQUENCE: 16

```
Met Met Lys Asn Arg Phe Pro Ala Ala Met Pro His Arg Asp Asn Pro
1               5                   10                  15

Thr Pro Leu Pro Ser Val Val Ala Leu Asn Cys Ile Glu Asp Cys Val
            20                  25                  30

Leu Glu Gln Asp Ser Leu Ala Gly Val Ala Leu Val Glu His Val Pro
        35                  40                  45

Leu Gly Arg Leu Ala Asp Gly Lys Ile Glu Ala Ala Ala Val Leu
50                  55                  60

Leu His Ser Leu Ala Tyr Leu Pro Arg Ala Ala Gln Arg Arg Leu Arg
65                  70                  75                  80

Pro Tyr Gln Leu Ile Leu Cys Leu Gly Ser Ser Asp Arg Thr Val Asp
                85                  90                  95

Ser Ala Leu Ala Ala Asp Leu Gly Leu Arg Leu Ile His Val Asp Thr
            100                 105                 110

Ser Arg Ala Glu Glu Ile Ala Asp Thr Val Met Ala Leu Leu Leu Gly
        115                 120                 125

Leu Leu Arg Arg Thr His Leu Leu Ala Arg His Ala Leu Ser Ala Ser
130                 135                 140

Gly Trp Leu Gly Ser Val Gln Pro Leu Cys Arg Gly Met Arg Arg Cys
145                 150                 155                 160

Arg Gly Leu Val Leu Gly Ile Val Gly Arg Ser Ala Ser Ala Arg Ala
                165                 170                 175

Leu Ala Thr Arg Ser Leu Ser Phe Lys Met Ser Val Leu Tyr Phe Asp
            180                 185                 190

Val Pro Glu Gly Lys Gly Lys Val Thr Phe Pro Ser Ala Ala Arg Arg
        195                 200                 205

Met Asp Thr Leu Asn Asp Leu Leu Ala Ala Ser Asp Val Ile Ser Leu
210                 215                 220

His Cys Ala Val Thr Asp Glu Thr Ile Gln Ile Ile Asn Ala Glu Cys
225                 230                 235                 240

Leu Gln His Ile Lys Pro Gly Ala Phe Leu Val Asn Thr Gly Ser Ser
                245                 250                 255

Gln Leu Leu Asp Asp Cys Ala Val Lys Gln Leu Leu Ile Asp Gly Thr
            260                 265                 270

Leu Ala Gly Cys Ala Leu Asp Gly Ala Glu Gly Pro Gln Trp Met Glu
        275                 280                 285

Ala Trp Val Arg Glu Met Pro Asn Val Leu Ile Leu Pro Arg Ser Ala
290                 295                 300

Asp Tyr Ser Glu Glu Val Trp Met Glu Ile Arg Asp Lys Ala Ile Ser
305                 310                 315                 320

Val Leu Gln Thr Phe Phe Phe Asp Gly Val Ile Pro Lys Asn Ala Ile
                325                 330                 335

Ser Asp Thr Glu Gly Cys Glu Asn Glu Ile Asp Asp Glu Ile Glu Gln
            340                 345                 350

Tyr Asn Lys Leu Asp Lys Val Ser Thr Leu Glu Gly Ser Val Gly Gly
        355                 360                 365

Gln Leu Thr Asp Asp Ile Gln Val Ser Pro Glu Asp Ser Leu Lys Lys
370                 375                 380

Gly Ile Ser Trp Ser Arg Asp Ser Pro Ser Gln Leu Gln Gly Ser Gly
385                 390                 395                 400
```

```
Phe Ser Gln Asn Ser Ala Asn Thr Lys Ser Asp Gly Arg Arg Ser Arg
                405                 410                 415

Ser Gly Lys Lys Ala Lys Arg His Ala Arg Gln Lys Ser Leu Gln
            420                 425                 430

Lys Pro Asp Pro Ser Ala Leu Glu Lys Glu Ser Thr Ser His Lys
            435                 440                 445

Glu Asp Asp Thr Ala Met Ser Gly Thr Asp Gln Ala Ser Ser Arg Cys
450                 455                 460

Ala Ser Pro Glu Glu Leu Arg Ser Arg Lys Thr Pro Ile Glu Ser Ile
465                 470                 475                 480

Gln Glu Ser Thr Ser Lys Lys Leu Ser Arg Ser Lys Lys Leu Ser
                485                 490                 495

Glu Val Ser Gly Glu Thr Leu Lys Asp Gly Tyr Val Val Ala Leu Tyr
                500                 505                 510

Ala Arg Asp Arg Pro Ala Leu His Ile Ser Arg Gln Arg His Lys Gly
                515                 520                 525

Gly Gly Trp Ile Leu Glu Thr Met Ser Asn Val Thr Lys Arg Asp Pro
                530                 535                 540

Ala Ala Gln Phe Leu Ile Cys Lys Ser Lys Asp Thr Ile Gly Leu Arg
545                 550                 555                 560

Ser Phe Thr Ala Gly Gly Lys Leu Leu Gln Ile Asn Arg Arg Met Glu
                565                 570                 575

Phe Val Phe Ala Ser His Ser Phe Asp Ala Trp Glu Ser Trp Ala Ile
                580                 585                 590

Glu Gly Pro Leu Glu Glu Cys Arg Leu Val Asn Cys Arg Asn Pro Leu
                595                 600                 605

Ala Phe Leu Asp Val Arg Ile Glu Ile Leu Ala Ala Val Gly Glu Asp
                610                 615                 620

Asp Gly Ile Thr Arg Trp Leu Asp
625                 630

<210> SEQ ID NO 17
<211> LENGTH: 632
<212> TYPE: PRT
<213> ORGANISM: Citrus clementine

<400> SEQUENCE: 17

Met Met Lys Asn Arg Phe Pro Ala Ala Met Pro His Arg Asp Asn Pro
1               5                   10                  15

Thr Pro Leu Pro Ser Val Val Ala Leu Asn Cys Ile Glu Asp Cys Val
                20                  25                  30

Leu Glu Gln Asp Ser Leu Ala Gly Val Ala Leu Val Glu His Val Pro
            35                  40                  45

Leu Gly Arg Leu Ala Asp Gly Lys Ile Glu Ala Ala Ala Val Leu
50                  55                  60

Leu His Ser Leu Ala Tyr Leu Pro Arg Ala Ala Gln Arg Arg Leu Arg
65                  70                  75                  80

Pro Tyr Gln Leu Ile Leu Cys Leu Gly Ser Ser Asp Arg Thr Val Asp
                85                  90                  95

Ser Ala Leu Ala Ala Asp Leu Gly Leu Arg Leu Ile His Val Asp Thr
            100                 105                 110

Ser Arg Ala Glu Glu Ile Ala Asp Thr Val Met Ala Leu Leu Leu Gly
            115                 120                 125

Leu Leu Arg Arg Thr His Leu Leu Ala Arg His Ala Leu Ser Ala Ser
```

-continued

```
            130                 135                 140
Gly Trp Leu Gly Ser Val Gln Pro Leu Cys Arg Gly Met Arg Cys
145                 150                 155                 160

Arg Gly Leu Val Leu Gly Ile Val Gly Arg Ser Ala Ser Ala Arg Ala
                165                 170                 175

Leu Ala Thr Arg Ser Leu Ser Phe Lys Met Ser Val Leu Tyr Phe Asp
            180                 185                 190

Val Pro Glu Gly Lys Gly Lys Val Thr Phe Pro Ser Ala Ala Arg Arg
                195                 200                 205

Met Asp Thr Leu Asn Asp Leu Leu Ala Ala Ser Asp Val Ile Ser Leu
            210                 215                 220

His Cys Ala Val Thr Asp Glu Thr Ile Gln Ile Ile Asn Ala Glu Cys
225                 230                 235                 240

Leu Gln His Ile Lys Pro Gly Ala Phe Leu Val Asn Thr Gly Ser Ser
                245                 250                 255

Gln Leu Leu Asp Asp Cys Ala Val Lys Gln Leu Leu Ile Asp Gly Thr
            260                 265                 270

Leu Ala Gly Cys Ala Leu Asp Gly Ala Glu Gly Pro Gln Trp Met Glu
        275                 280                 285

Ala Trp Val Arg Glu Met Pro Asn Val Leu Ile Leu Pro Arg Ser Ala
290                 295                 300

Asp Tyr Ser Glu Glu Val Trp Met Glu Ile Arg Asp Lys Ala Ile Ser
305                 310                 315                 320

Val Leu Gln Thr Phe Phe Phe Asp Gly Val Ile Pro Lys Asn Ala Ile
                325                 330                 335

Ser Asp Thr Glu Gly Cys Glu Asn Glu Ile Asp Asp Glu Ile Glu Gln
            340                 345                 350

Tyr Asn Lys Leu Asp Lys Val Ser Thr Leu Glu Gly Ser Val Gly Gly
            355                 360                 365

Gln Leu Thr Asp Asp Ile Gln Val Ser Pro Glu Asp Ser Leu Lys Lys
        370                 375                 380

Gly Ile Ser Trp Ser Arg Asp Ser Pro Ser Gln Leu Gln Gly Ser Gly
385                 390                 395                 400

Phe Ser Gln Asn Ser Ala Asn Thr Lys Ser Asp Gly Arg Arg Ser Arg
                405                 410                 415

Ser Gly Lys Lys Ala Lys Lys Arg His Ala Arg Gln Lys Ser Leu Gln
            420                 425                 430

Lys Pro Asp Asp Pro Ser Ala Leu Glu Lys Glu Ser Thr Ser His Lys
        435                 440                 445

Glu Asp Asp Thr Ala Met Ser Gly Thr Asp Gln Ala Ser Ser Arg Cys
450                 455                 460

Ala Ser Pro Glu Glu Leu Arg Ser Arg Lys Thr Pro Ile Glu Ser Ile
465                 470                 475                 480

Gln Glu Ser Thr Ser Lys Lys Leu Ser Arg Ser Ser Lys Lys Leu Ser
                485                 490                 495

Glu Val Ser Gly Glu Thr Leu Lys Asp Gly Tyr Val Val Ala Leu Tyr
            500                 505                 510

Ala Arg Asp Arg Pro Ala Leu His Ile Ser Arg Gln Arg His Lys Gly
        515                 520                 525

Gly Gly Trp Ile Leu Glu Thr Met Ser Asn Val Thr Lys Arg Asp Pro
530                 535                 540

Ala Ala Gln Phe Leu Ile Cys Lys Ser Lys Asp Thr Ile Gly Leu Arg
545                 550                 555                 560
```

```
Ser Phe Thr Ala Gly Gly Lys Leu Leu Gln Ile Asn Arg Arg Met Glu
                565                 570                 575

Phe Val Phe Ala Ser His Ser Phe Asp Ala Trp Glu Ser Trp Ala Ile
            580                 585                 590

Glu Gly Pro Leu Glu Glu Cys Arg Leu Val Asn Cys Arg Asn Pro Leu
            595                 600                 605

Ala Phe Leu Asp Val Arg Ile Glu Ile Leu Ala Ala Val Gly Glu Asp
            610                 615                 620

Asp Gly Ile Thr Arg Trp Leu Asp
625                 630

<210> SEQ ID NO 18
<211> LENGTH: 617
<212> TYPE: PRT
<213> ORGANISM: Glycine max

<400> SEQUENCE: 18

Met Pro His Arg Asn Asn Pro Ala Pro Leu Pro Leu Val Val Thr Leu
1               5                   10                  15

Asn Cys Val Glu Asp Cys Ser Leu Glu Phe Glu Ser Leu Ala Gly Val
            20                  25                  30

Ala Thr Val Glu His Val Pro Leu Ser Arg Leu Ser Asp Gly Lys Ile
            35                  40                  45

Glu Ser Ala Ala Ala Val Leu Leu His Ser Leu Ala Tyr Leu Pro Arg
        50                  55                  60

Ala Ala Gln Arg Arg Leu Arg Ser Tyr His Leu Ile Leu Cys Leu Gly
65                  70                  75                  80

Ser Ala Asp Arg Ala Val Asp Ser Ala Leu Ala Ala Asp Leu Gly Leu
            85                  90                  95

Arg Leu Val His Val Asp Thr Ser Arg Ala Glu Glu Ile Ala Asp Thr
            100                 105                 110

Val Met Ala Leu Phe Leu Gly Leu Leu Arg Arg Thr His Leu Leu Ser
            115                 120                 125

Arg His Ala Leu Ser Ala Ser Gly Trp Leu Gly Ser Val Gln Pro Leu
            130                 135                 140

Cys Arg Gly Met Arg Arg Cys Arg Gly Leu Val Leu Gly Ile Val Gly
145                 150                 155                 160

Ile Ser Ser Ser Ala Arg Ser Leu Ala Thr Arg Ser Leu Ala Phe Lys
            165                 170                 175

Met Ser Val Leu Tyr Phe Asp Ala Arg Ala Glu Lys Gly Lys Val Lys
            180                 185                 190

Phe Pro Pro Ala Ala Arg Arg Met Asp Thr Leu Asn Asp Leu Leu Ala
            195                 200                 205

Ala Ser Asp Leu Ile Ser Leu His Cys Ala Leu Thr Asn Glu Thr Met
        210                 215                 220

Gln Ile Ile Asn Ala Glu Cys Leu Gln His Val Lys Pro Gly Ala Phe
225                 230                 235                 240

Ile Val Asn Thr Gly Ser Ser Gln Leu Leu Asp Asp Cys Ala Val Lys
            245                 250                 255

Gln Leu Leu Ile Asp Gly Thr Leu Ala Gly Cys Ala Leu Asp Gly Ala
            260                 265                 270

Glu Gly Pro Gln Trp Met Glu Ala Trp Val Lys Glu Met Pro Asn Val
            275                 280                 285

Leu Ile Leu Pro Arg Ser Ala Asp Tyr Ser Glu Glu Val Trp Met Glu
```

```
            290                 295                 300
Ile Arg Glu Lys Ala Ile Ser Ile Leu Gln Thr Phe Phe Ile Asp Gly
305                 310                 315                 320

Ile Ile Pro Lys Asn Ala Met Ser Asp Val Glu Glu Ser Glu Val
                325                 330                 335

Asp Asn Glu Ser Glu Gln Ser Asp Gln Gln Tyr Asn Gly Asn Ala Leu
                340                 345                 350

Gln Ile Ile Val Arg Glu Gln Thr Asp Asp Val His Val Ser Pro Asp
                355                 360                 365

Asn Ser Gln Lys Lys Ile Ser Thr Gln Met Lys Glu Ser Ser Ser Gln
370                 375                 380

His Gln Val Ser Ser Leu Ser Gln Ser Thr Ser Ala Arg Ser Glu Gly
385                 390                 395                 400

Arg Arg Ser Arg Ser Gly Lys Lys Ala Lys Arg His Thr Arg His
                405                 410                 415

Lys Ser Gln Gln Lys His Glu Asp Pro Ser Ala Leu Glu Lys Glu Gly
                420                 425                 430

Thr Ser Gln Arg Asp Asp Thr Ala Met Ser Gly Thr Asp Gln Ala Leu
                435                 440                 445

Ser Ser Ser Ser Glu Asp Ser Arg Asn Arg Lys Thr Pro Ile Glu Ser
    450                 455                 460

Met Gln Glu Pro Thr Gly Ala Gln Val Ile Lys Ser Ser Leu Arg Leu
465                 470                 475                 480

Ser Gly Asn Cys Thr Glu Leu Leu Lys Asp Gly Tyr Ile Ile Ala Leu
                485                 490                 495

Tyr Ala Arg Asp Cys Ser Ala Leu His Val Ser Arg Gln Arg Val Lys
                500                 505                 510

Gly Gly Gly Trp Ile Met Asp Ser Met Ser Asn Val Ser Lys Arg Asp
                515                 520                 525

Pro Ala Ala Gln Phe Leu Ile Ile Phe Arg Ser Lys Asp Thr Ile Gly
                530                 535                 540

Leu Arg Ser Leu Ala Ala Gly Gly Lys Leu Leu Gln Ile Asn Arg Arg
545                 550                 555                 560

Met Glu Phe Val Phe Ala Ser His Ser Phe Asp Val Trp Glu Asn Trp
                565                 570                 575

Thr Leu Glu Gly Ser Leu Gln Cys Arg Leu Val Asn Cys Arg Asn
                580                 585                 590

Pro Ser Ala Val Leu Asp Val Arg Val Glu Ile Leu Ala Thr Val Gly
                595                 600                 605

Glu Asp Gly Val Thr Arg Trp Leu Glu
                610                 615

<210> SEQ ID NO 19
<211> LENGTH: 631
<212> TYPE: PRT
<213> ORGANISM: Solanum tuberosum

<400> SEQUENCE: 19

Met Ala His His Asn Lys Thr Thr Ser Leu Ile Thr Gln Gln Val Pro
1               5                   10                  15

Leu Val Ile Thr Leu Asn Cys Ile Glu Asp Thr Thr Leu Glu Gln Glu
                20                  25                  30

Cys Leu Ser Gly Ile Ala Val Ile Glu His Val Pro Leu Ser Arg Leu
                35                  40                  45
```

-continued

```
Ala Glu Ala Arg Ile Glu Ser Ala Thr Ala Val Leu Leu His Ser Leu
 50                  55                  60

Ala Phe Leu Pro Arg Ala Ala Gln Arg Arg Leu Arg Ser Trp Gln Leu
 65                  70                  75                  80

Ile Leu Cys Leu Gly Ser Ser Asp Arg Ala Val Asp Ser Ala Leu Ala
                 85                  90                  95

Ser Asp Leu Gly Leu Ser Arg Leu Val His Val Asp Val Asn Arg Ala
                100                 105                 110

Glu Glu Val Ala Asp Thr Val Met Ala Leu Ile Leu Gly Leu Leu Arg
                115                 120                 125

Arg Thr His Leu Leu Ser Arg His Thr Leu Ser Ala Ser Gly Trp Leu
130                 135                 140

Gly Ser Val Gln Pro Leu Cys Arg Gly Met Arg Arg Cys Arg Gly Leu
145                 150                 155                 160

Val Leu Gly Ile Val Gly Arg Ser Ala Ser Ala Arg Ser Leu Ala Thr
                165                 170                 175

Arg Ser Leu Ala Phe Asn Met Ser Val Leu Tyr Phe Asp Val Glu Gly
                180                 185                 190

Asn Gly Lys Met Ser Arg His Ser Ile Arg Phe Pro Pro Ala Ala Arg
                195                 200                 205

Arg Met Asp Thr Leu Asn Asp Leu Leu Ala Ala Ser Asp Leu Ile Ser
210                 215                 220

Leu His Cys Ala Leu Thr Asn Glu Thr Val Gln Ile Ile Asn Ala Asp
225                 230                 235                 240

Cys Leu Gln His Val Lys Pro Gly Ala Phe Leu Val Asn Thr Gly Ser
                245                 250                 255

Cys Gln Leu Leu Asp Asp Cys Ala Val Lys Gln Leu Leu Ile Glu Gly
                260                 265                 270

Ser Ile Ala Gly Cys Ala Leu Asp Gly Ala Glu Gly Pro Gln Trp Met
                275                 280                 285

Glu Ala Trp Val Arg Glu Met Pro Asn Val Leu Ile Leu Pro Arg Ser
290                 295                 300

Ala Asp Tyr Ser Glu Glu Val Trp Met Glu Ile Arg Glu Lys Ala Ile
305                 310                 315                 320

Ser Met Leu Gln Ser Phe Phe Leu Asp Gly Val Ala Pro Lys Asp Ser
                325                 330                 335

Val Ser Asp Glu Glu Glu Ser Glu Ile Gly Tyr Asp Asn Glu Val
                340                 345                 350

His Gln Ile Gln Asp Val Glu Ser Ala Leu Gln Gly Ser Pro Ser Gln
                355                 360                 365

Gln Ala Ile Glu Asp Val Ala Glu Ser Ser Gln Lys Arg Leu Ala Ser
370                 375                 380

Val Ser Arg Glu Ser Pro Ser Gln Leu Gln Gly Ser Met Val Ser Gln
385                 390                 395                 400

Asn Ser Ser Gly Arg Ser Glu Val Lys Arg Ser Arg Ser Gly Lys Lys
                405                 410                 415

Ala Lys Lys Arg His Gly Arg Gln Lys Ser Gln His Lys Val Asp Asp
                420                 425                 430

His Leu Ala Phe Glu Lys Glu Ser Thr Ser His Glu Asp Gly Ala
                435                 440                 445

Thr Met Ser Gly Thr Asp Gln Gly Val Ser Ser Ser Arg Phe Ala
450                 455                 460

Ser Pro Glu Asp Leu Arg Gly Arg Lys Thr Ser Ile Glu Ser Ile Gln
```

```
            465                 470                 475                 480
Glu Ser Ser Val Glu Gln Leu Ser Lys Lys Gly Ile Asn Leu Ser Arg
                485                 490                 495

Lys Ser Ser Glu Leu Leu Lys Asp Gly Tyr Val Ile Ala Leu His Ala
                500                 505                 510

Arg His His Pro Ala Leu His Val Ser Arg Gln Arg Val Lys Gly Gly
                515                 520                 525

Gly Trp Phe Leu Asp Thr Met Ser Asp Val Thr Lys Arg Asp Pro Ala
                530                 535                 540

Ala Gln Phe Leu Val Val Ser Arg Ser Lys Asp Thr Ile Gly Leu Arg
545                 550                 555                 560

Ser Phe Thr Ala Gly Gly Lys Leu Leu Gln Ile Asn Arg Arg Met Glu
                565                 570                 575

Phe Val Phe Ala Ser His Ser Phe Asp Val Trp Glu Ser Trp Thr Phe
                580                 585                 590

Glu Gly Thr Met Glu Glu Cys Arg Leu Val Asn Cys Arg Asn Pro Leu
                595                 600                 605

Ala Val Leu Asp Val Arg Val Glu Val Leu Ala Ala Val Gly Glu Asp
                610                 615                 620

Gly Ile Thr Arg Trp Leu Asp
625                 630

<210> SEQ ID NO 20
<211> LENGTH: 642
<212> TYPE: PRT
<213> ORGANISM: Eucalyptus grandis

<400> SEQUENCE: 20

Met Ala Gly Ser Ser Leu Ala Val Val Pro Arg Gln Ala Asp Pro
1               5                   10                  15

Ser Ser Leu Pro Leu Val Val Ala Leu Asn Cys Ile Glu Asp Cys Ser
                20                  25                  30

Leu Glu Gln Asp Ser Leu Ala Gly Val Ala Ser Val Glu His Val Pro
                35                  40                  45

Leu Ser Arg Leu Ala Ser Asp Arg Thr Ile Asp Ser Ala Ser Ala
                50                  55                  60

Val Leu Leu His Ser Leu Ala Phe Leu Pro Arg Ala Ala Gln Arg Arg
65                  70                  75                  80

Leu Arg Pro Tyr Gln Leu Val Leu Cys Leu Gly Ser Ala Asp Arg Ser
                85                  90                  95

Val Asp Ser Ala Leu Ala Ala Glu Leu Gly Leu Arg Leu His Val
                100                 105                 110

Asp Thr Ser Arg Ala Glu Glu Ile Ala Asp Thr Val Met Ala Leu Val
                115                 120                 125

Leu Ser Leu Leu Arg Arg Thr His Leu Leu Ala Arg His Ala Leu Ser
130                 135                 140

Ala Ser Gly Trp Leu Gly Ser Val Gln Pro Leu Cys Arg Gly Met Arg
145                 150                 155                 160

Arg Cys Arg Gly Leu Val Leu Gly Ile Ile Gly Arg Ser Ser Ser Ala
                165                 170                 175

Lys Ser Leu Ala Thr Arg Gly Leu Ala Phe Lys Met Ser Val Leu Tyr
                180                 185                 190

Phe Asp Val Val Asp Ala Asn Gly Lys Val Ile Arg Pro Ser Ile Ser
                195                 200                 205
```

```
Phe Pro Pro Ser Ala Arg Arg Met Glu Thr Leu Asn Asp Leu Leu Ala
    210                 215                 220

Ala Ser Asp Ile Val Ser Leu His Cys Ala Leu Thr Asn Glu Thr Ile
225                 230                 235                 240

Gln Ile Leu Asn Ala Glu Cys Leu Gln His Ile Lys Pro Gly Ala Phe
                245                 250                 255

Leu Val Asn Thr Gly Ser Cys Gln Leu Leu Asp Asp Cys Val Val Lys
            260                 265                 270

Gln Met Leu Ile Asp Gly Ser Leu Ala Gly Cys Ala Leu Asp Gly Ala
        275                 280                 285

Glu Gly Pro Gln Trp Met Glu Ala Trp Val Arg Glu Met Pro Asn Val
290                 295                 300

Leu Ile Leu Pro Arg Ser Ala Asp Tyr Ser Glu Glu Val Trp Met Glu
305                 310                 315                 320

Ile Arg Glu Lys Ala Ile Ser Met Leu Gln Thr Tyr Phe Phe Asp Gly
                325                 330                 335

Ile Val Pro Lys Asp Thr Val Ser Asp Glu Glu Glu Glu Asn Glu
            340                 345                 350

Ile Ala Asp Glu Asn Gln Lys Phe Asp Ser Arg Asp Lys Glu Ser Val
        355                 360                 365

Pro Gln Val Ser Ser Val Ala Gln Val Thr Asp Ile Ile Gln Leu Ser
370                 375                 380

Arg Glu Ser Thr Gln Lys Val Gly Thr Ser Gln Leu Val Glu Ser Pro
385                 390                 395                 400

Asp His Asn Gln Gly Ser Gly Leu Ser Gln Asn Thr Val Ala Arg Pro
                405                 410                 415

Glu Ala Arg Arg Gly Arg Ala Gly Lys Lys Ala Lys Lys Arg His Gly
            420                 425                 430

Arg Gln Lys Leu Gly Gln Lys Phe Asp Asp Pro Ser Ser Leu Gly Lys
        435                 440                 445

Glu Ser Ala Ser Asn Arg Glu Asp Asp Thr Ala Met Ser Gly Thr Asp
450                 455                 460

Gln Val Leu Ser Ser Ser Arg Phe Ala Ser Pro Asp Asp Ser Arg
465                 470                 475                 480

Ser Arg Lys Met Pro Leu Asp Ser Met Gln Asp Ser Thr Pro Ser Gln
                485                 490                 495

Pro His Lys Ser Ile Arg Asn Leu Ser Gly Arg Pro Gly Asp Leu Leu
            500                 505                 510

Lys Asp Gly Tyr Val Val Ala Leu Tyr Ala Lys Asp His Pro Ala Leu
        515                 520                 525

His Val Ser Arg Gln Arg Val Lys Gly Gly Trp Phe Leu Asp Thr
530                 535                 540

Ile Ser Asn Val Thr Lys Arg Asp Pro Ala Ala Gln Phe Leu Val Val
545                 550                 555                 560

Leu Arg Gly Lys Glu Thr Ile Gly Leu Arg Ser Phe Ala Ala Gly Gly
                565                 570                 575

Lys Leu Leu Gln Ile Asn Arg Arg Met Glu Phe Val Phe Ala Ser His
            580                 585                 590

Ser Phe Asp Val Trp Glu Ser Trp Thr Leu Glu Gly Ser Leu Asp Glu
        595                 600                 605

Cys Lys Leu Val Asn Cys Arg Asn Ser Gln Ala Val Leu Glu Val Arg
610                 615                 620

Val Glu Ile Leu Ala Val Val Gly Asp Asp Gly Ile Thr Arg Trp
```

```
                625                 630                 635                 640

Ile Asp

<210> SEQ ID NO 21
<211> LENGTH: 650
<212> TYPE: PRT
<213> ORGANISM: Oryza sativa

<400> SEQUENCE: 21

Met Leu His Gly Pro Ala His Ser Pro Pro Ala Ala Ala Val
1               5                   10                  15

Ala Val Ala Gly Gly Gly Gly Glu Pro Leu Val Val Thr Leu Asn
            20                  25                  30

Cys Leu Glu Asp Pro Ser Met Glu Gln Glu Val Leu Ala Gly Ala Ala
            35                  40                  45

Ala Val Glu His Ala Pro Leu Ser Ala Leu Ser Ser Gly Arg Val Glu
50                  55                  60

Ala Ala Ala Ala Val Leu Leu Thr Ser Leu Ala Phe Leu Pro Arg Ala
65                  70                  75                  80

Ala Gln Arg Arg Leu Arg Pro Trp Gln Leu Ile Leu Cys Leu Gly Ser
                85                  90                  95

Pro Asp Arg Ala Ala Asp Ala Ala Val Ala Ala Glu Leu Gly Leu Arg
            100                 105                 110

Leu Val His Val Asp Ala Asn Arg Ala Glu Glu Val Ala Asp Thr Val
            115                 120                 125

Met Ala Leu Phe Leu Gly Leu Leu Arg Arg Thr His Leu Leu Ser Arg
130                 135                 140

His Ala Ser Ser Tyr Ser Ala Pro Pro Ala Gly Trp Leu Gly Ser Val
145                 150                 155                 160

Gln Pro Leu Cys Arg Gly Met Arg Arg Cys Arg Gly Leu Val Leu Gly
                165                 170                 175

Ile Val Gly Val Asn Ala Ala Ala Arg Cys Leu Ala Thr Arg Ser Leu
            180                 185                 190

Ala Phe Ser Met Ser Val Leu Tyr Phe Asp Pro Leu His Glu Ala Asn
            195                 200                 205

Gly Lys Thr Lys Arg Pro Ser Ile Leu Phe Pro Ser Ala Ala Arg Arg
210                 215                 220

Met Asp Thr Leu Asn Asp Leu Leu Thr Ala Ser Asp Leu Val Ser Leu
225                 230                 235                 240

His Cys Ala Leu Thr Asn Asp Thr Thr His Ile Leu Asn Ala Glu Arg
                245                 250                 255

Leu Gln His Ile Lys Pro Gly Ala Phe Ile Val Asn Thr Gly Ser Cys
            260                 265                 270

Gln Leu Ile Asp Asp Cys Ala Leu Lys Gln Leu Leu Ile Asp Gly Thr
            275                 280                 285

Ile Ala Gly Cys Ala Leu Asp Gly Ala Glu Gly Pro Gln Trp Met Glu
290                 295                 300

Ala Trp Val Arg Glu Met Pro Asn Val Leu Ile Leu Pro Arg Ser Ala
305                 310                 315                 320

Asp Tyr Ser Glu Glu Val Trp Ile Glu Ile Arg Glu Lys Ala Leu Ala
                325                 330                 335

Ile Leu Gln Ser Phe Phe Tyr Asp Gly Val Val Pro Asn Asn Ala Leu
            340                 345                 350

Ser Asp Asp Glu Glu Glu Ile Thr Glu Ala Gly Cys Glu Asp Asp Gln
```

```
                    355                 360                 365
Leu Ala Lys Gln Ala Lys Glu Gln Val Cys Asp Gly Gly Gln Gln Thr
    370                 375                 380

Asp Glu Ser Gln Leu Thr Leu Glu Cys Asp Lys Arg Arg Ala Ile Ser
385                 390                 395                 400

His Ser Glu Glu Pro Gln Ala Ser Gly Gln Ser Gln Asn Arg Glu Asn
                405                 410                 415

Val Val Pro Arg Ser Glu Gly Arg Arg Ser Arg Ser Gly Lys Lys Gly
            420                 425                 430

Lys Lys Arg Pro Ala Arg Arg Lys Ser Gln Gln Lys Arg Asp Glu Leu
        435                 440                 445

Leu Ser Thr Leu Glu Gly Gly Ser Asn Tyr Ser Ser Arg Met Asp Asp
    450                 455                 460

Asp Thr Val Thr Ser Gly Lys Asp Gln Val Leu Ser Ser Ser Ser Arg
465                 470                 475                 480

Phe Ala Ser Pro Glu Asp Cys Lys Thr Lys Leu Arg Ser Ser Ala Glu
                485                 490                 495

Phe Pro Met Glu Ile Ile Ser Glu Asn Lys Leu Thr Ala Gly Leu Ser
            500                 505                 510

Ile Lys Pro Leu Glu Arg Leu Lys Asp Gly Phe Val Ala Leu Arg
        515                 520                 525

Thr Arg Asp Asn Ser Gly Phe His Val Ala Arg Glu Arg Val Ala Gly
    530                 535                 540

Val Gly Trp Tyr Leu Asp Val Val Ser Lys Ala Thr Lys Arg Asp Pro
545                 550                 555                 560

Ala Ala Gln Phe Leu Ile Thr Phe Arg Asn Lys Asp Thr Met Gly Leu
                565                 570                 575

Arg Ser Phe Val Ala Gly Gly Lys Leu Leu Gln Val Asn Lys Thr Met
            580                 585                 590

Glu Leu Val Phe Ala Ser Tyr Ser Phe Asp Val Trp Glu Ser Trp Thr
        595                 600                 605

Leu Glu Gly Ser Leu Leu Asp Cys Cys Lys Leu Val Asn Arg Lys Ile
    610                 615                 620

Pro Ser Val Val Leu Glu Val Tyr Ile Glu Ile Leu Ala Ala Val Ser
625                 630                 635                 640

Glu Glu Asp Gly Val Thr Arg Trp Leu Asp
                645                 650

<210> SEQ ID NO 22
<211> LENGTH: 637
<212> TYPE: PRT
<213> ORGANISM: Sorghum bicolor

<400> SEQUENCE: 22

Met Leu His Gly Pro Ala His Ser Ala Ser Pro Ala Thr Ala Ala Ala
1               5                   10                  15

Gly Gly Gly Val Gln Pro Leu Val Val Ala Leu Asn Cys Leu Glu Asp
            20                  25                  30

Pro Ser Leu Glu Gln Glu Ala Leu Ser Gly Ala Ala Ala Val Glu His
        35                  40                  45

Ala Pro Leu Ser Ser Leu Ser Ala Gly Arg Val Glu Ala Ala Ala Ala
    50                  55                  60

Val Leu Leu Pro Ser Leu Ala Phe Leu Pro Arg Ala Ala Gln Arg Arg
65                  70                  75                  80
```

```
Leu Arg Pro Trp Gln Leu Leu Leu Cys Leu Gly Ser Pro Glu Arg Ala
                85                  90                  95

Ala Asp Ala Ala Ala Ala Glu Leu Gly Leu Arg Leu Val His Val
            100                 105                 110

Asp Ala Asn Arg Ala Glu Glu Val Ala Asp Thr Val Met Ala Leu Phe
            115                 120                 125

Leu Gly Leu Leu Arg Arg Thr His Leu Leu Ser Arg His Ala Ser Ser
        130                 135                 140

Ser Ser Pro Thr Ala Gly Trp Leu Gly Ser Val Gln Pro Leu Cys Arg
145                 150                 155                 160

Gly Met Arg Arg Cys Arg Gly Leu Val Leu Gly Ile Ile Gly Val Asn
                165                 170                 175

Ala Ala Ala Arg Cys Leu Ala Thr Arg Ser Leu Ala Phe Arg Met Ser
            180                 185                 190

Val Leu Tyr Phe Asp Pro Ile Tyr Glu Val Thr Gly Lys Val Lys Arg
        195                 200                 205

Pro Ser Ile Val Phe Pro Ser Ala Ala Arg Arg Met Asp Thr Leu Asn
    210                 215                 220

Asp Leu Leu Ala Ala Ser Asp Leu Val Ser Leu His Cys Ala Leu Thr
225                 230                 235                 240

Asn Asp Thr Thr His Ile Leu Asn Ala Glu Arg Leu Gln His Ile Lys
                245                 250                 255

Pro Gly Ala Phe Ile Val Asn Thr Gly Ser Cys Gln Leu Ile Asp Asp
            260                 265                 270

Cys Ala Leu Lys Gln Leu Leu Ile Asp Gly Thr Ile Ala Gly Cys Ala
        275                 280                 285

Leu Asp Gly Ala Glu Gly Pro Gln Trp Met Glu Ala Trp Val His Glu
    290                 295                 300

Met Pro Asn Val Leu Ile Leu Pro Arg Ser Ala Asp Tyr Ser Glu Glu
305                 310                 315                 320

Val Trp Met Glu Ile Arg Glu Lys Ala Ile Ala Ile Leu Gln Ser Phe
                325                 330                 335

Leu Tyr Asp Gly Val Val Pro Asn Asn Val Ile Ser Asp Glu Asp Glu
            340                 345                 350

Glu Ile Ser Glu Val Gly Cys Asp Asp Gln Leu Ala Lys Gln Glu
        355                 360                 365

Lys Glu His Ala Leu Gln Ile Cys Asp Gly Glu Gln Gln Thr Glu Glu
    370                 375                 380

Ser Gln Leu Thr Ala Glu Tyr Asp Lys Arg Arg Ala Ile Ser Gln Pro
385                 390                 395                 400

Glu Glu Pro Gln Ala Ser Ala Gln Ser His Thr Ile Gly Ser Arg Ser
                405                 410                 415

Glu Gly Arg Arg Ser Arg Ser Gly Lys Lys Gly Lys Lys Arg Pro Ala
            420                 425                 430

Arg Arg Arg Ser Gln Gln Lys Met Asp Glu Leu Ser Thr Val Glu Gly
        435                 440                 445

Gly Ser Asn Tyr Ser Ser Arg Arg Asp Asp Asn Gln Val Leu Ser
    450                 455                 460

Ser Ser Ser Arg Phe Ala Ser Pro Glu Asp Ser Lys Asn Lys His Lys
465                 470                 475                 480

Ser Ser Val Glu Ser Pro Met Glu Ile Ile Ser Glu Asn Lys Leu Pro
                485                 490                 495

Ala Gly Leu Gly Arg Lys Pro Pro Glu Lys Leu Lys Glu Gly Phe Val
```

```
            500                 505                 510
Ile Ala Leu Lys Thr Arg Asp Asn Ser Gly Phe Tyr Val Ser Arg Glu
            515                 520                 525

Arg Val Ala Gly Gly Gly Trp Tyr Leu Asp Val Ile Pro Asn Ala Thr
        530                 535                 540

Lys Arg Asp Pro Ala Ala Gln Phe Leu Val Thr Phe Arg Asn Lys Asp
545                 550                 555                 560

Thr Met Gly Leu Arg Ser Phe Val Ala Gly Gly Lys Leu Leu Gln Ala
                565                 570                 575

Asn Asn Lys Met Glu Phe Val Phe Thr Ser His Ser Phe Asp Val Cys
            580                 585                 590

Glu Ser Trp Met Leu Glu Gly Ser Leu Ser Glu Cys Cys Lys Leu Val
        595                 600                 605

Asn Arg Lys Asn Ser Leu Ala Val Leu Glu Val Tyr Ile Glu Val Leu
        610                 615                 620

Gly Ala Pro Ser Glu Asp Gly Val Val Arg Trp Leu Asp
625                 630                 635

<210> SEQ ID NO 23
<211> LENGTH: 646
<212> TYPE: PRT
<213> ORGANISM: Hodeum vulgare

<400> SEQUENCE: 23

Met Leu Arg Gly Pro Ala His Ser Val Pro Ala Thr Ala Val Ala Ala
1               5                   10                  15

Thr Ala Gly Gly Gly Gly Gln Pro Leu Val Val Thr Leu Asn Cys Leu
            20                  25                  30

Glu Asp Pro Ser Val Glu Arg Asp Ala Leu Ala Gly Ala Ala Ala Val
        35                  40                  45

Glu His Ala Pro Leu Ser Ala Leu Ala Ser Gly His Val Glu Ala Ala
    50                  55                  60

Val Ala Val Leu Leu Thr Ser Leu Ala Phe Leu Pro Arg Ala Ala Gln
65                  70                  75                  80

Arg Arg Leu Arg Pro Trp Gln Leu Leu Leu Cys Leu Gly Ser Pro Asp
                85                  90                  95

Arg Ala Ala Asp Ser Ala Ala Ala Ala Glu Leu Gly Leu Arg Leu Val
            100                 105                 110

His Val Asp Ala Asn Arg Ala Glu Glu Ile Ala Asp Thr Val Met Ala
        115                 120                 125

Leu Phe Leu Gly Leu Leu Arg Arg Thr His Leu Leu Ser Gly His Ala
    130                 135                 140

Ser Ser Ser Thr Pro Ser Ala Gly Trp Leu Gly Ser Val Gln Pro Leu
145                 150                 155                 160

Cys Arg Gly Met Arg Arg Cys Arg Gly Leu Val Leu Gly Ile Val Gly
                165                 170                 175

Val Asn Ala Ala Ala Arg Cys Leu Ala Thr Arg Ser Leu Ala Phe Arg
            180                 185                 190

Met Ser Val Leu Tyr Phe Asp Pro Leu Tyr Glu Gly Ala Gly Lys Thr
        195                 200                 205

Lys Arg Pro Ser Ile Val Phe Pro Ser Ser Ala Arg Arg Met Asp Thr
    210                 215                 220

Leu Asn Asp Leu Leu Ala Ala Ser Asp Leu Val Ser Leu His Cys Ala
225                 230                 235                 240
```

```
Leu Thr Asn Asp Thr Thr Asn Ile Ile Ser Ala Glu Arg Leu Gln His
            245                 250                 255

Ile Lys Pro Gly Ala Phe Ile Val Asn Thr Ser Ser Cys Gln Leu Ile
        260                 265                 270

Asp Asp Cys Ala Leu Lys Gln Leu Leu Leu Asp Gly Thr Ile Ala Gly
    275                 280                 285

Cys Ala Leu Asp Gly Ala Glu Gly Pro Gln Trp Met Glu Ala Trp Val
290                 295                 300

His Glu Met Pro Asn Val Leu Ile Leu Pro Arg Ser Ala Asp Tyr Ser
305                 310                 315                 320

Glu Glu Val Trp Met Glu Ile Arg Glu Lys Ala Ile Thr Ile Leu Gln
                325                 330                 335

Ser Phe Phe Phe Asp Gly Ile Val Pro Asn Asn Ala Ile Ser Asp Glu
                340                 345                 350

Asp Glu Ala Ile Ser Asp Val Gly Cys Glu Asp Asp Gln Leu Tyr Lys
                355                 360                 365

Gln Ala Asn Glu His Ser Leu Arg Val Cys Asp Ser Gln Gln Thr
    370                 375                 380

Asp Glu Ser Gln Leu Thr Leu Asp Cys Asp Lys Arg Arg Ala Ile Ser
385                 390                 395                 400

Lys Val Glu Val Pro Glu Ala Ser Gly Gln Ser Gln Ser Ile Gly Leu
                405                 410                 415

Arg Ser Glu Gly Arg Arg Ser Arg Ser Gly Lys Lys Gly Lys Lys Arg
                420                 425                 430

Pro Ala Arg Arg Arg Ser Gln Gln Lys Met Asp Glu Leu Ser Thr Val
            435                 440                 445

Glu Ser Gly Ser Asn Tyr Ser Ser Arg Arg Asp Asp Thr Val Met
450                 455                 460

Ser Gly Arg Asp Gln Val Leu Ser Ser Ser Arg Phe Ala Ser Pro
465                 470                 475             480

Glu Glu Ser Lys Asn Lys Leu Arg Ser Ser Ala Glu Ser Pro Met Glu
                485                 490                 495

Ile Ile Ser Glu His Lys Leu Pro Ala Gly Leu Gly Arg Lys Pro Pro
            500                 505                 510

Glu Arg Leu Lys Asp Gly Phe Val Val Ala Leu Arg Thr Arg Asp Asn
            515                 520                 525

Ser Gly Phe His Val Ser Arg Glu Arg Val Ala Gly Gly Trp Tyr
            530                 535                 540

Leu Asp Val Val Ser Asn Ala Thr Lys Arg Asp Pro Ala Ala Gln Phe
545                 550                 555                 560

Leu Ile Thr Phe Lys Asn Lys Asp Thr Met Gly Leu Arg Ser Phe Val
                565                 570                 575

Ala Gly Gly Lys Leu Leu Gln Val Asn Lys Lys Ala Glu Leu Val Phe
            580                 585                 590

Ala Asn His Ala Phe Asp Val Trp Glu Ser Trp Thr Leu Glu Gly Ser
            595                 600                 605

Leu Leu Glu Cys Cys Lys Leu Val Asn His Arg Asn Pro Leu Ala Val
    610                 615                 620

Leu Glu Val Tyr Ile Glu Ile Leu Ala Ala Val Ser Glu Glu Asp Gly
625                 630                 635                 640

Val Thr Arg Trp Leu Asp
                645
```

```
<210> SEQ ID NO 24
<211> LENGTH: 643
<212> TYPE: PRT
<213> ORGANISM: Zea mays

<400> SEQUENCE: 24
```

| | | | | | | | | | | | | | | | |
|---|---|---|---|---|---|---|---|---|---|---|---|---|---|---|---|
| Met | Ala | His | Ser | Pro | Ala | Pro | Ser | Gly | Gly | Gly | Gly | Gly | Pro | Leu | |
| 1 | | | | 5 | | | | | 10 | | | | | 15 | |
| Pro | Leu | Leu | Val | Ser | Leu | Asn | Cys | Leu | Asp | Asp | Leu | Ser | Leu | Glu | Gln |
| | | | 20 | | | | | 25 | | | | | 30 | | |
| Glu | Gly | Leu | Ala | Gly | Val | Ala | Ala | Val | Glu | His | Val | Pro | Leu | Ser | Ala |
| | | | | 35 | | | | | 40 | | | | | 45 | |
| Val | Ala | Cys | Gly | Arg | Ile | Glu | Ala | Ala | Ser | Ala | Val | Leu | Leu | Pro | Ser |
| | 50 | | | | | 55 | | | | | 60 | | | | |
| Leu | Ala | Phe | Leu | Pro | Arg | Ala | Ala | Gln | Arg | Arg | Leu | Arg | Pro | Trp | Gln |
| 65 | | | | | 70 | | | | | 75 | | | | | 80 |
| Leu | Leu | Leu | Cys | Leu | Gly | Ser | Ala | Asp | Arg | Ala | Ala | Asp | Ala | Ala | Ala |
| | | | | 85 | | | | | 90 | | | | | 95 | |
| Ala | Ala | Asp | Leu | Gly | Leu | Arg | Leu | Val | His | Val | Asp | Ala | Asn | Arg | Ala |
| | | | 100 | | | | | 105 | | | | | 110 | | |
| Glu | Glu | Val | Ala | Asp | Thr | Val | Met | Ala | Leu | Ile | Leu | Gly | Leu | Leu | Arg |
| | | | | 115 | | | | | 120 | | | | | 125 | |
| Arg | Thr | His | Leu | Leu | Ser | Cys | His | Ala | Ser | Ser | Val | Pro | Ala | Ala | Gly |
| | 130 | | | | | 135 | | | | | 140 | | | | |
| Trp | Leu | Gly | Ser | Val | Gln | Pro | Met | Cys | Arg | Gly | Met | Arg | Arg | Cys | Arg |
| 145 | | | | | 150 | | | | | 155 | | | | | 160 |
| Gly | Leu | Val | Leu | Gly | Ile | Ile | Gly | Arg | Ser | Ala | Ala | Arg | Cys | Leu | |
| | | | | 165 | | | | | 170 | | | | | 175 | |
| Ala | Thr | Arg | Ser | Leu | Ala | Phe | Arg | Met | Ser | Val | Leu | Tyr | Phe | Asp | Pro |
| | | | 180 | | | | | 185 | | | | | 190 | | |
| Arg | Tyr | Val | Ala | Ser | Gly | Lys | Thr | Lys | Arg | Pro | Ser | Ile | Val | Phe | Pro |
| | | | | 195 | | | | | 200 | | | | | 205 | |
| Ser | Ala | Ala | Arg | Arg | Met | Asp | Thr | Leu | Asn | Asp | Leu | Leu | Ala | Ala | Ser |
| | 210 | | | | | 215 | | | | | 220 | | | | |
| Asp | Leu | Ile | Ser | Leu | His | Cys | Gly | Leu | Thr | Asn | Glu | Thr | Met | His | Ile |
| 225 | | | | | 230 | | | | | 235 | | | | | 240 |
| Leu | Asn | Ala | Asp | Cys | Leu | Gln | His | Ile | Lys | Pro | Gly | Ala | Phe | Ile | Val |
| | | | | 245 | | | | | 250 | | | | | 255 | |
| Asn | Thr | Gly | Ser | Cys | Gln | Leu | Ile | Asp | Asp | Cys | Ala | Leu | Lys | Gln | Leu |
| | | | 260 | | | | | 265 | | | | | 270 | | |
| Leu | Ile | Asp | Gly | Thr | Ile | Ala | Gly | Cys | Ala | Leu | Asp | Gly | Ala | Glu | Gly |
| | | | | 275 | | | | | 280 | | | | | 285 | |
| Pro | Gln | Trp | Met | Glu | Ala | Trp | Val | Arg | Glu | Met | Pro | Asn | Val | Leu | Ile |
| | 290 | | | | | 295 | | | | | 300 | | | | |
| Leu | Pro | Arg | Ser | Ala | Asp | Tyr | Ser | Glu | Glu | Val | Trp | Met | Glu | Ile | Arg |
| 305 | | | | | 310 | | | | | 315 | | | | | 320 |
| Glu | Lys | Ala | Ile | Thr | Met | Leu | Gln | Ser | Phe | Phe | Asp | Gly | Val | Leu | |
| | | | | 325 | | | | | 330 | | | | | 335 | |
| Pro | Ser | Ser | Ala | Ile | Ser | Asp | Glu | Asp | Glu | Glu | Ile | Ser | Glu | Ala | Lys |
| | | | 340 | | | | | 345 | | | | | 350 | | |
| Asn | Glu | Asp | Asp | Tyr | Leu | Gly | Pro | Gln | Ala | Lys | Asp | Ser | Gln | Ser | Gln |
| | | | | 355 | | | | | 360 | | | | | 365 | |
| Ile | Phe | Asp | Thr | Glu | Ile | Asp | Glu | Ser | His | Ile | Thr | Leu | Glu | Ser | Glu |
| | 370 | | | | | 375 | | | | | 380 | | | | |

```
Lys Lys Arg Ala Ile Ser His His Lys Glu Pro Gln Ala Ser Gly Lys
385                 390                 395                 400

Ser Val Asn Ile Gly Ser Arg Ser Glu Gly Arg Arg Ser Arg Ser Gly
            405                 410                 415

Lys Lys Gly Lys Lys Arg Pro Ala His Arg Arg Pro Gln Gln Lys Pro
        420                 425                 430

Asp Asp Leu Ser Ala Val Glu Ser Asp Ser Asn Tyr Ser Ser Arg Arg
    435                 440                 445

Asp Asp Asp Thr Ala Met Ser Ser Arg Asp Gln Val Val Ser Ser Ser
450                 455                 460

Ser Arg Phe Ala Ser Pro Glu Asp Pro Lys Tyr Lys His Lys Ser Leu
465                 470                 475                 480

Ser Glu Ser Pro Met Glu Ile Thr Ser Glu Lys Lys Val Pro Val Leu
            485                 490                 495

Leu Ser Arg Lys Tyr Pro Asp Lys Leu Lys Asp Gly Phe Ile Val Ala
        500                 505                 510

Leu Arg Ala Arg Asp Asn Ser Gly Tyr His Val Ala Arg Gln Arg Val
    515                 520                 525

Val Gly Gly Gly Trp Ile Leu Asp Val Val Ser Asn Ala Thr Asn
530                 535                 540

Arg Asp Pro Ala Ala Gln Phe Leu Val Thr Phe Lys Asn Lys Asp Thr
545                 550                 555                 560

Met Gly Leu Arg Ser Phe Val Ala Gly Gly Lys Leu Leu Gln Ile Asn
            565                 570                 575

Arg Lys Met Glu Phe Val Phe Ala Ser His Ser Phe Asp Val Trp Glu
        580                 585                 590

Ser Trp Met Leu Asp Gly Ser Leu Leu Glu Gly Ser Lys Leu Ile Asn
    595                 600                 605

Cys Arg Asn Pro Ser Ala Val Leu Asp Ile Cys Ile Glu Ile Leu Ala
610                 615                 620

Ala Pro Ser Glu Glu Asp Gly Val Thr Arg Trp Leu Asp Ser Pro Arg
625                 630                 635                 640

Trp Gly Leu

<210> SEQ ID NO 25
<211> LENGTH: 383
<212> TYPE: PRT
<213> ORGANISM: Drosophila melanogaster

<400> SEQUENCE: 25

Met Asp Lys Asn Leu Met Met Pro Lys Arg Ser Arg Ile Asp Val Lys
1               5                   10                  15

Gly Asn Phe Ala Asn Gly Pro Leu Gln Ala Arg Pro Leu Val Ala Leu
            20                  25                  30

Leu Asp Gly Arg Asp Cys Ser Ile Glu Met Pro Ile Leu Lys Asp Val
        35                  40                  45

Ala Thr Val Ala Phe Cys Asp Ala Gln Ser Thr Ser Glu Ile His Glu
    50                  55                  60

Lys Val Leu Asn Glu Ala Val Gly Ala Leu Met Trp His Thr Ile Ile
65                  70                  75                  80

Leu Thr Lys Glu Asp Leu Glu Lys Phe Lys Ala Leu Arg Ile Ile Val
                85                  90                  95

Arg Ile Gly Ser Gly Thr Asp Asn Ile Asp Val Lys Ala Ala Gly Glu
            100                 105                 110
```

Leu Gly Ile Ala Val Cys Asn Val Pro Gly Tyr Val Glu Val
            115                 120                 125

Ala Asp Thr Thr Met Cys Leu Ile Leu Asn Leu Tyr Arg Arg Thr Tyr
130                 135                 140

Trp Leu Ala Asn Met Val Arg Glu Gly Lys Lys Phe Thr Gly Pro Glu
145                 150                 155                 160

Gln Val Arg Glu Ala His Gly Cys Ala Arg Ile Arg Gly Asp Thr
            165                 170                 175

Leu Gly Leu Val Gly Leu Gly Arg Ile Gly Ser Ala Val Ala Leu Arg
            180                 185                 190

Ala Lys Ala Phe Gly Phe Asn Val Ile Phe Tyr Asp Pro Tyr Leu Pro
            195                 200                 205

Asp Gly Ile Asp Lys Ser Leu Gly Leu Thr Arg Val Tyr Thr Leu Gln
            210                 215                 220

Asp Leu Leu Phe Gln Ser Asp Cys Val Ser Leu His Cys Thr Leu Asn
225                 230                 235                 240

Glu His Asn His His Leu Ile Asn Glu Phe Thr Ile Lys Gln Met Arg
            245                 250                 255

Pro Gly Ala Phe Leu Val Asn Thr Ala Arg Gly Gly Leu Val Asp Asp
            260                 265                 270

Glu Thr Leu Ala Leu Ala Leu Lys Gln Gly Arg Ile Arg Ala Ala Ala
            275                 280                 285

Leu Asp Val His Glu Asn Glu Pro Tyr Asn Gly Ala Leu Lys Asp Ala
            290                 295                 300

Pro Asn Leu Ile Cys Thr Pro His Ala Ala Phe Phe Ser Asp Ala Ser
305                 310                 315                 320

Ala Thr Glu Leu Arg Glu Met Ala Ala Thr Glu Ile Arg Arg Ala Ile
            325                 330                 335

Val Gly Asn Ile Pro Asp Val Leu Arg Asn Cys Val Asn Lys Glu Tyr
            340                 345                 350

Phe Met Arg Thr Pro Pro Ala Ala Ala Gly Val Ala Ala Ala
            355                 360                 365

Val Tyr Pro Glu Gly Lys Leu Gln Met Ile Ser Asn Gln Glu Lys
            370                 375                 380

<210> SEQ ID NO 26
<211> LENGTH: 440
<212> TYPE: PRT
<213> ORGANISM: Homo sapiens

<400> SEQUENCE: 26

Met Gly Ser Ser His Leu Leu Asn Lys Gly Leu Pro Leu Gly Val Arg
1               5                   10                  15

Pro Pro Ile Met Asn Gly Pro Leu His Pro Arg Pro Leu Val Ala Leu
            20                  25                  30

Leu Asp Gly Arg Asp Cys Thr Val Glu Met Pro Ile Leu Lys Asp Val
            35                  40                  45

Ala Thr Val Ala Phe Cys Asp Ala Gln Ser Thr Gln Glu Ile His Glu
50                  55                  60

Lys Val Leu Asn Glu Ala Val Gly Ala Leu Met Tyr His Thr Ile Thr
65                  70                  75                  80

Leu Thr Arg Glu Asp Leu Glu Lys Phe Lys Ala Leu Arg Ile Ile Val
            85                  90                  95

Arg Ile Gly Ser Gly Phe Asp Asn Ile Asp Ile Lys Ser Ala Gly Asp
            100                 105                 110

Leu Gly Ile Ala Val Cys Asn Val Pro Ala Ser Val Glu Glu Thr
            115                 120                 125

Ala Asp Ser Thr Leu Cys His Ile Leu Asn Leu Tyr Arg Arg Ala Thr
130                 135                 140

Trp Leu His Gln Ala Leu Arg Glu Gly Thr Arg Val Gln Ser Val Glu
145                 150                 155                 160

Gln Ile Arg Glu Val Ala Ser Gly Ala Ala Arg Ile Arg Gly Glu Thr
                165                 170                 175

Leu Gly Ile Ile Gly Leu Gly Arg Val Gly Gln Ala Val Ala Leu Arg
            180                 185                 190

Ala Lys Ala Phe Gly Phe Asn Val Leu Phe Tyr Asp Pro Tyr Leu Ser
        195                 200                 205

Asp Gly Val Glu Arg Ala Leu Gly Leu Gln Arg Val Ser Thr Leu Gln
    210                 215                 220

Asp Leu Leu Phe His Ser Asp Cys Val Thr Leu His Cys Gly Leu Asn
225                 230                 235                 240

Glu His Asn His His Leu Ile Asn Asp Phe Thr Val Lys Gln Met Arg
                245                 250                 255

Gln Gly Ala Phe Leu Val Asn Thr Ala Arg Gly Gly Leu Val Asp Glu
            260                 265                 270

Lys Ala Leu Ala Gln Ala Leu Lys Glu Gly Arg Ile Arg Gly Ala Ala
        275                 280                 285

Leu Asp Val His Glu Ser Glu Pro Phe Ser Phe Ser Gln Gly Pro Leu
    290                 295                 300

Lys Asp Ala Pro Asn Leu Ile Cys Thr Pro His Ala Ala Trp Tyr Ser
305                 310                 315                 320

Glu Gln Ala Ser Ile Glu Met Arg Glu Glu Ala Ala Arg Glu Ile Arg
                325                 330                 335

Arg Ala Ile Thr Gly Arg Ile Pro Asp Ser Leu Lys Asn Cys Val Asn
            340                 345                 350

Lys Asp His Leu Thr Ala Ala Thr His Trp Ala Ser Met Asp Pro Ala
        355                 360                 365

Val Val His Pro Glu Leu Asn Gly Ala Ala Tyr Arg Tyr Pro Pro Gly
    370                 375                 380

Val Val Gly Val Ala Pro Thr Gly Ile Pro Ala Ala Val Glu Gly Ile
385                 390                 395                 400

Val Pro Ser Ala Met Ser Leu Ser His Gly Leu Pro Pro Val Ala His
                405                 410                 415

Pro Pro His Ala Pro Ser Pro Gly Gln Thr Val Lys Pro Glu Ala Asp
            420                 425                 430

Arg Asp His Ala Ser Asp Gln Leu
        435                 440

<210> SEQ ID NO 27
<211> LENGTH: 440
<212> TYPE: PRT
<213> ORGANISM: Mus musculus

<400> SEQUENCE: 27

Met Gly Ser Ser His Leu Leu Asn Lys Gly Leu Pro Leu Gly Val Arg
1               5                   10                  15

Pro Pro Ile Met Asn Gly Pro Met His Pro Arg Pro Leu Val Ala Leu
            20                  25                  30

Leu Asp Gly Arg Asp Cys Thr Val Glu Met Pro Ile Leu Lys Asp Val

```
            35                  40                  45
Ala Thr Val Ala Phe Cys Asp Ala Gln Ser Thr Gln Glu Ile His Glu
 50                  55                  60

Lys Val Leu Asn Glu Ala Val Gly Ala Leu Met Tyr His Thr Ile Thr
 65                  70                  75                  80

Leu Thr Arg Glu Asp Leu Glu Lys Phe Lys Ala Leu Arg Ile Ile Val
                 85                  90                  95

Arg Ile Gly Ser Gly Phe Asp Asn Ile Asp Ile Lys Ser Ala Gly Asp
                100                 105                 110

Leu Gly Ile Ala Val Cys Asn Val Pro Ala Ala Ser Val Glu Glu Thr
            115                 120                 125

Ala Asp Ser Thr Leu Cys His Ile Leu Asn Leu Tyr Arg Arg Thr Thr
130                 135                 140

Trp Leu His Gln Ala Leu Arg Glu Gly Thr Arg Val Gln Ser Val Glu
145                 150                 155                 160

Gln Ile Arg Glu Val Ala Ser Gly Ala Ala Arg Ile Arg Gly Glu Thr
                165                 170                 175

Leu Gly Ile Ile Gly Leu Gly Arg Val Gly Gln Ala Val Ala Leu Arg
            180                 185                 190

Ala Lys Ala Phe Gly Phe Asn Val Leu Phe Tyr Asp Pro Tyr Leu Ser
        195                 200                 205

Asp Gly Ile Glu Arg Ala Leu Gly Leu Gln Arg Val Ser Thr Leu Gln
210                 215                 220

Asp Leu Leu Phe His Ser Asp Cys Val Thr Leu His Cys Gly Leu Asn
225                 230                 235                 240

Glu His Asn His His Leu Ile Asn Asp Phe Thr Val Lys Gln Met Arg
                245                 250                 255

Gln Gly Ala Phe Leu Val Asn Thr Ala Arg Gly Gly Leu Val Asp Glu
            260                 265                 270

Lys Ala Leu Ala Gln Ala Leu Lys Glu Gly Arg Ile Arg Gly Ala Ala
        275                 280                 285

Leu Asp Val His Glu Ser Glu Pro Phe Ser Phe Ser Gln Gly Pro Leu
290                 295                 300

Lys Asp Ala Pro Asn Leu Ile Cys Thr Pro His Ala Ala Trp Tyr Ser
305                 310                 315                 320

Glu Gln Ala Ser Ile Glu Met Arg Glu Glu Ala Ala Arg Glu Ile Arg
                325                 330                 335

Arg Ala Ile Thr Gly Arg Ile Pro Asp Ser Leu Lys Asn Cys Val Asn
            340                 345                 350

Lys Asp His Leu Thr Ala Ala Thr His Trp Ala Ser Met Asp Pro Ala
        355                 360                 365

Val Val His Pro Glu Leu Asn Gly Ala Ala Tyr Arg Tyr Pro Pro Gly
370                 375                 380

Val Val Ser Val Ala Pro Thr Gly Ile Pro Ala Ala Val Glu Gly Ile
385                 390                 395                 400

Val Pro Ser Ala Met Ser Leu Ser His Gly Leu Pro Val Ala His
                405                 410                 415

Pro Pro His Ala Pro Ser Pro Gly Gln Thr Val Lys Pro Glu Ala Asp
            420                 425                 430

Arg Asp His Thr Ser Asp Gln Leu
        435                 440

<210> SEQ ID NO 28
```

```
<211> LENGTH: 440
<212> TYPE: PRT
<213> ORGANISM: Xenopus laevis

<400> SEQUENCE: 28
```

| | | | | | | | | | | | | | | |
|---|---|---|---|---|---|---|---|---|---|---|---|---|---|---|
|Met|Gly|Ser|Ser|His|Leu|Leu|Asn|Lys|Gly|Leu|Pro|Leu|Gly|Ile|Arg|
|1| | | |5| | | | |10| | | | |15|

Pro Pro Ile Met Asn Gly Pro Met His Pro Arg Pro Leu Val Ala Leu
            20              25              30

Leu Asp Gly Arg Asp Cys Thr Val Glu Met Pro Ile Leu Lys Asp Val
            35              40              45

Ala Thr Val Ala Phe Cys Asp Ala Gln Ser Thr Gln Glu Ile His Glu
50              55              60

Lys Val Leu Asn Glu Ala Val Gly Ala Leu Met Tyr His Thr Ile Thr
65              70              75              80

Leu Thr Arg Glu Asp Leu Glu Lys Phe Lys Ala Leu Arg Ile Ile Val
            85              90              95

Arg Ile Gly Ser Gly Phe Asp Asn Ile Asp Ile Lys Ser Ala Gly Asp
            100             105             110

Leu Gly Ile Ala Val Cys Asn Val Pro Ala Ala Ser Val Glu Glu Thr
            115             120             125

Ala Asp Ser Thr Met Cys His Ile Leu Asn Leu Tyr Arg Arg Thr Thr
130             135             140

Trp Leu His Gln Ala Leu Arg Glu Gly Thr Arg Val Gln Ser Val Glu
145             150             155             160

Gln Ile Arg Glu Val Ala Ser Gly Ala Ala Arg Ile Arg Gly Glu Thr
            165             170             175

Leu Gly Ile Ile Gly Leu Gly Arg Val Gly Gln Ala Val Ala Leu Arg
            180             185             190

Ala Lys Thr Phe Gly Phe Asn Val Phe Phe Tyr Asp Pro Tyr Leu Ser
            195             200             205

Asp Gly Ile Glu Arg Ala Leu Gly Leu Gln Arg Val Ser Thr Leu Gln
            210             215             220

Asp Leu Leu Phe His Ser Asp Cys Val Thr Leu His Cys Gly Leu Asn
225             230             235             240

Glu His Asn His His Leu Ile Asn Asp Phe Thr Ile Lys Gln Met Arg
            245             250             255

Gln Gly Ala Phe Leu Val Asn Thr Ala Arg Gly Gly Leu Val Asp Glu
            260             265             270

Lys Ala Leu Ala Gln Ala Leu Lys Glu Gly Arg Ile Arg Gly Ala Ala
            275             280             285

Leu Asp Val His Glu Ser Glu Pro Phe Ser Phe Thr Gln Gly Pro Leu
            290             295             300

Lys Asp Ala Pro Asn Leu Ile Cys Thr Pro His Ala Ala Trp Tyr Ser
305             310             315             320

Glu Gln Ala Ser Ile Glu Met Arg Glu Ala Ala Arg Glu Ile Arg
            325             330             335

Arg Ala Ile Thr Gly Arg Ile Pro Asp Ser Leu Lys Asn Cys Val Asn
            340             345             350

Lys Asp His Leu Thr Ala Ala Thr His Trp Ala Ser Met Asp Pro Gly
            355             360             365

Val Val His Pro Glu Leu Asn Gly Gly Ala Tyr Arg Tyr Pro Gln Gly
            370             375             380

Val Val Ser Val Ala Pro Ala Gly Leu Pro Ala Ala Val Glu Gly Ile

Val Pro Ser Ala Met Ser Leu Ser His Ala His Pro Ala Val Ala His
385                 390                 395                 400
                405                 410                 415

Pro Pro His Ala Pro Ser Pro Gly Gln Thr Ile Lys Pro Glu Ala Asp
                420                 425                 430

Arg Asp His Pro Ser Asp Gln Leu
                435                 440

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
caccatgagc gccacgacta cc                                          22

<210> SEQ ID NO 30
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 30
ctaatctagc caacgagtaa cacc                                        24

<210> SEQ ID NO 31
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 31
actccacttg gtgctccgtt tgagg                                       25

<210> SEQ ID NO 32
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 32
agtctctgct ggtctggtgg gatacect                                    28

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
acgtcagcga tgcctcaggg                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
gctaccaacc gggaggggt                                                    20

<210> SEQ ID NO 35
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 35
gggtcgccaa aaccgaacac ca                                                22

<210> SEQ ID NO 36
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 36
tccaatttcc gaaggtttag cccca                                             25

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 37
gtcgcccttc ttcagtccag ca                                                22

<210> SEQ ID NO 38
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 38
acagtcctct ggtgggattc cct                                               23

<210> SEQ ID NO 39
<211> LENGTH: 666
<212> TYPE: PRT
<213> ORGANISM: Populus trichocarpa

<400> SEQUENCE: 39

Met Ser Ala Thr Thr Thr Arg Ser Leu Ala Thr Met Ser His Arg Arg
1               5                   10                  15

Asn Thr Asn Thr Pro Pro Pro Gln Gln Gln Gln Gln Gln Gln Gln Gln
                20                  25                  30

Gln Gln Gln Arg Leu Pro Leu Val Val Thr Leu Asn Cys Ile Glu Asp
            35                  40                  45

Phe Ala Ile Glu Gln Asp Ser Leu Ser Gly Val Ala Leu Ile Glu His
        50                  55                  60

Val Pro Leu Gly Arg Leu Ser Asp Gly Lys Ile Glu Ser Ala Ala Ala
65                  70                  75                  80

Val Leu Leu His Ser Leu Ala Tyr Leu Pro Arg Ala Ala Gln Arg Arg
                85                  90                  95

Leu Arg Pro Tyr Gln Leu Ile Leu Cys Leu Gly Ser Ala Asp Arg Ala

```
            100                 105                 110
Val Asp Ser Ala Leu Ala Ala Asp Leu Gly Leu Arg Leu Val His Val
            115                 120                 125

Asp Thr Ser Arg Ala Glu Glu Ile Ala Asp Thr Val Met Ala Leu Phe
            130                 135                 140

Leu Gly Leu Leu Arg Arg Thr His Leu Leu Ser Arg His Ala Leu Ser
145                 150                 155                 160

Ala Ser Gly Trp Leu Gly Ser Leu Gln Pro Leu Cys Arg Gly Met Arg
                165                 170                 175

Arg Cys Arg Gly Leu Val Leu Gly Ile Val Gly Arg Ser Ala Ser Ala
            180                 185                 190

Arg Ser Leu Ala Thr Arg Ser Leu Ala Phe Lys Met Ser Val Leu Tyr
            195                 200                 205

Phe Asp Val His Glu Gly Pro Gly Lys Leu Thr Arg Ser Ser Ile Thr
            210                 215                 220

Phe Pro Leu Ala Ala Arg Arg Met Asp Thr Leu Asn Asp Leu Leu Ala
225                 230                 235                 240

Ala Ser Asp Leu Ile Ser Leu His Cys Ala Leu Thr Asn Glu Thr Val
                245                 250                 255

Gln Ile Ile Asn Glu Glu Cys Leu Gln His Ile Lys Pro Gly Ile Leu
            260                 265                 270

Leu Ser Leu Leu Ile Leu Arg Arg Ala Phe Leu Val Asn Thr Gly Ser
            275                 280                 285

Ser Gln Leu Leu Asp Asp Cys Ala Leu Lys Gln Leu Leu Ile Asp Gly
            290                 295                 300

Thr Leu Ala Gly Cys Ala Leu Asp Gly Ala Glu Gly Pro Gln Trp Met
305                 310                 315                 320

Glu Ala Trp Val Lys Glu Met Pro Asn Val Leu Ile Leu Pro Arg Ser
                325                 330                 335

Ala Asp Tyr Ser Glu Glu Val Trp Met Glu Ile Arg Glu Lys Ala Ile
            340                 345                 350

Ser Ile Leu Gln Ser Phe Phe Phe Asp Gly Ile Val Pro Lys Asn Ala
            355                 360                 365

Val Ser Asp Glu Glu Gly Glu Glu Ser Glu Ile Gly Asp Glu Ser Glu
            370                 375                 380

Gln Phe His Arg Gln Asp Lys Glu Ser Thr Leu Gln Asp Ser Val Gly
385                 390                 395                 400

Glu Gln Leu Thr Asp Asp Ile Gln Leu Thr Pro Glu Thr Ser Arg Lys
                405                 410                 415

Lys Val Ser Gly Gln Ser Ile Glu Ser Thr Ser Gln Ala Gln Gly Ser
            420                 425                 430

Gly Met Ser Gln Asn Thr Thr Thr Arg Ser Asp Glu Arg Ser Arg Arg
            435                 440                 445

Ser Gly Lys Lys Ala Lys Lys Arg His Gly Arg Gln Lys Pro Arg Gln
            450                 455                 460

Lys Ser Asp Asn Pro Ser Gln Leu Glu Lys Glu Ser Thr Ser His Gln
465                 470                 475                 480

Glu Asp Asp Thr Ala Met Ser Gly Ser Asp Gln Val Ser Ser Ser Arg
                485                 490                 495

Phe Ala Ser Pro Glu Asp Ser Arg Ser Arg Lys Thr Pro Ile Glu Leu
            500                 505                 510

Met Gln Glu Ser Ser Ser Gly Gln Leu Ser Arg Ser Gly Lys Arg Leu
            515                 520                 525
```

-continued

```
Ser Gly Lys Ser Asp Glu Leu Leu Lys Asp Gly His Ile Ile Ala Leu
        530                 535                 540

Tyr Ala Arg Asp Arg Pro Ala Leu His Val Ser Arg Gln Arg Ala Lys
545                     550                 555                 560

Gly Gly Gly Trp Phe Leu Asp Ala Leu Ser Asn Val Thr Lys Arg Asp
                565                 570                 575

Pro Ala Ala Gln Phe Leu Val Val Phe Arg Asn Lys Asp Thr Ile Gly
            580                 585                 590

Leu Arg Ser Phe Ala Ala Gly Gly Lys Leu Leu Gln Ile Asn Arg Arg
        595                 600                 605

Met Glu Phe Val Phe Thr Ser His Ser Phe Asp Val Trp Glu Ser Trp
        610                 615                 620

Met Leu Glu Gly Ser Leu Asp Glu Cys Arg Leu Val Asn Cys Arg Asn
625                 630                 635                 640

Pro Leu Ala Ile Leu Asp Ala Arg Val Glu Ile Leu Ala Ala Ile Ala
                645                 650                 655

Glu Asp Asp Gly Val Thr Arg Trp Leu Asp
                660                 665
```

What is claimed is:

1. A method comprising:
   a. identifying a plant comprising an allelic variant of the POPTR_0014s08530 gene wherein said allelic variant encodes an increased number of glutamines relative to the sequence of SEQ ID NO:2, wherein said identifying comprises obtaining nucleic acids from a plant and detecting the presence of said allelic variant; and
   b. producing biofuel or cellulose-based products from said plant.

2. A method comprising:
   a. identifying a plant comprising an allelic variant of the POPTR_0014s08530 gene wherein said allelic variant encodes a decreased number of glutamines relative to the sequence of SEQ ID NO:2, wherein said identifying comprises obtaining nucleic acids from a plant and detecting the presence of said allelic variant; and
   b. producing lignin-based products from said plant.

3. The method of claim 1, wherein the allelic variant present in said plant encodes a polypeptide with at least 85% sequence identity to SEQ ID NO: 2.

4. The method of claim 1, wherein the allelic variant encodes SEQ ID NO: 4.

5. The method of claim 3, wherein the allelic variant encodes a polypeptide with at least 95% sequence identity to SEQ ID NO: 2.

6. The method of claim 1, wherein the detection in step (a) is by polymerase chain reaction or nucleic acid hybridization.

7. The method of claim 2, wherein the lignin-related product is a carbon fiber.

8. The method of claim 1, wherein the cellulose-related products are selected from the group consisting of cellulose, paper and pulp.

9. The method of claim 2, wherein the allelic variant present in said plant encodes a polypeptide with at least 85% sequence identity to SEQ ID NO:2.

10. The method of claim 2, wherein the allelic variant encodes a polypeptide with at least 95% sequence identity to SEQ ID NO:2.

11. The method of claim 2, wherein the detection in step (a) is by polymerase chain reaction or nucleic acid hybridization.

12. The method of claim 5, wherein the allelic variant encodes a polypeptide with at least 98% sequence identity to SEQ ID NO: 2.

13. The method of claim 2, wherein the allelic variant encodes a polypeptide with at least 98% sequence identity to SEQ ID NO: 2.

14. The method of claim 10, wherein the allelic variant differs from SEQ ID NO: 2 by having 11 glutamines.

* * * * *